US010557128B2

(12) United States Patent
Low et al.

(10) Patent No.: US 10,557,128 B2
(45) Date of Patent: Feb. 11, 2020

(54) PSMA BINDING LIGAND-LINKER CONJUGATES AND METHODS FOR USING

(71) Applicant: PURDUE RESEARCH FOUNDATION, West Lafayette, IN (US)

(72) Inventors: Philip Stewart Low, West Lafayette, IN (US); Venkatesh Chelvam, West Lafayette, IN (US); Youngsoon Kim, West Lafayette, IN (US); Sumith A. Kularatne, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/934,974

(22) Filed: Mar. 24, 2018

(65) Prior Publication Data
US 2019/0002861 A1 Jan. 3, 2019

Related U.S. Application Data

(63) Continuation of application No. 15/018,068, filed on Feb. 8, 2016, now Pat. No. 9,951,324, which is a continuation-in-part of application No. 13/580,436, filed as application No. PCT/US2011/026238 on Feb. 25, 2011, now abandoned.

(60) Provisional application No. 61/308,190, filed on Feb. 25, 2010.

(51) Int. Cl.
*C12N 9/48* (2006.01)
*A61K 31/454* (2006.01)
*A61K 31/4745* (2006.01)
*A61K 31/475* (2006.01)
*C12N 9/96* (2006.01)
*A61K 49/00* (2006.01)
*A61K 51/04* (2006.01)
*A61K 47/54* (2017.01)
*A61K 38/00* (2006.01)

(52) U.S. Cl.
CPC ............ *C12N 9/485* (2013.01); *A61K 31/454* (2013.01); *A61K 31/475* (2013.01); *A61K 31/4745* (2013.01); *A61K 47/542* (2017.08); *A61K 49/0032* (2013.01); *A61K 49/0052* (2013.01); *A61K 51/0402* (2013.01); *C12N 9/96* (2013.01); *A61K 38/00* (2013.01); *C12Y 304/17021* (2013.01)

(58) Field of Classification Search
CPC .............. A61K 31/454; A61K 31/4745; A61K 31/475; A61K 38/00; A61K 47/542; A61K 49/0032; A61K 49/0052; A61K 51/0402; C12N 9/485; C12N 9/96; C12Y 304/17021
See application file for complete search history.

(56) References Cited

U.S. PATENT DOCUMENTS

| | | |
|---|---|---|
| 4,691,024 A | 9/1987 | Shirahata et al. |
| 4,713,249 A | 12/1987 | Schroder |
| 5,103,018 A | 4/1992 | Motomichi et al. |
| 5,266,333 A | 11/1993 | Cady et al. |
| 5,418,982 A | 5/1995 | Kishi et al. |
| 5,627,165 A | 5/1997 | Glazier et al. |
| 5,795,877 A | 8/1998 | Jackson et al. |
| 5,863,536 A | 1/1999 | Jackson et al. |
| 5,866,679 A | 2/1999 | DeFeo-Jones et al. |
| 5,902,817 A | 5/1999 | Jackson et al. |
| 5,948,750 A | 9/1999 | Garsky et al. |
| 5,962,237 A | 10/1999 | Ts'o et al. |
| 5,962,521 A | 10/1999 | Jackson et al. |
| 5,968,915 A | 10/1999 | Jackson et al. |
| 5,998,362 A | 12/1999 | Feng et al. |
| 6,054,444 A | 4/2000 | Jackson et al. |
| 6,127,333 A | 10/2000 | Brady et al. |
| 6,174,858 B1 | 1/2001 | Brady et al. |
| 6,177,404 B1 | 1/2001 | DeFeo-Jones et al. |
| 6,232,287 B1 | 5/2001 | Ruoslahti et al. |
| 6,368,598 B1 | 4/2002 | D'Amico et al. |
| 6,391,305 B1 | 5/2002 | Feng et al. |
| 6,428,785 B1 | 8/2002 | Gokcen et al. |
| 6,479,470 B1 | 11/2002 | Kozikowski et al. |
| 6,528,499 B1 | 3/2003 | Kozikowski et al. |
| 6,692,724 B1 | 2/2004 | Yang et al. |
| 6,875,886 B2 | 4/2005 | Frangioni et al. |
| 6,946,133 B1 | 9/2005 | Schlom et al. |

(Continued)

FOREIGN PATENT DOCUMENTS

| | | |
|---|---|---|
| CA | 2606138 | 10/2005 |
| CN | 101863924 | 10/2010 |

(Continued)

OTHER PUBLICATIONS

The Chemistry of Oxygen and Sulfur, https://web.archive.org/web/20080625021202/http://chemed.chem.purdue.edu/genchem/topicreview/bp/ch10/group6.php#oxygen ( date Jun. 25, 2008) accessed online on May 31, 2019, 21 pages. (Year: 2008).*
Chinese Patent Application No. 201480071256, by Endocyte, Inc. et al.: Office Action, dated Apr. 20, 2017 (9 pages).
Eurasian Patent Application No. 201690862/28, by Endocyte, Inc. et al.: Office Action, dated May 22, 2017; English Translation (2 pages).
Liu M., et al., "Synthesis and Biological Evaluation of Diethylenetriamine Pentaacetic acid-Polyethylene Glycol Folate: A new Folate-Derived, [99m]Tc-Based Radiopharmaceutical," Bioconjugate Chem., 2005 vol. 16, p. 1126-1132.

(Continued)

*Primary Examiner* — Marcela M Cordero Garcia
(74) *Attorney, Agent, or Firm* — Barnes & Thornburg LLP

(57) ABSTRACT

Described herein are prostate specific membrane antigen (PSMA) binding conjugates that are useful for delivering therapeutic, diagnostic and imaging agents. Also described herein are pharmaceutical compositions containing them and methods of using the conjugates and compositions. Also described are processes for manufacture of the conjugates and the compositions containing them.

26 Claims, No Drawings

(56) References Cited

U.S. PATENT DOCUMENTS

| | | |
|---|---|---|
| 7,008,765 B1 | 3/2006 | Bussemakers et al. |
| 7,128,893 B2 | 10/2006 | Leamon et al. |
| 7,129,254 B2 | 10/2006 | Berger et al. |
| 7,147,837 B2 | 12/2006 | Lauffer et al. |
| 7,192,586 B2 | 3/2007 | Bander et al. |
| 7,232,805 B2 | 6/2007 | Weinshenker et al. |
| 7,361,338 B2 | 4/2008 | Jakobovits et al. |
| 7,381,745 B2 | 6/2008 | Kozikowski et al. |
| 7,399,460 B2 | 7/2008 | Wedeking et al. |
| 7,408,079 B2 | 8/2008 | Pomper et al. |
| 7,485,299 B2 | 2/2009 | Afar et al. |
| 7,514,078 B2 | 4/2009 | Bander et al. |
| 7,534,580 B2 | 5/2009 | Reeves et al. |
| 7,601,332 B2 | 10/2009 | Vlahov et al. |
| 7,635,682 B2 | 12/2009 | Denmeade et al. |
| 7,638,122 B2 | 12/2009 | Yu et al. |
| 7,659,395 B2 | 2/2010 | Pajouhesh et al. |
| 7,662,795 B2 | 2/2010 | Rodriguez et al. |
| 7,696,185 B2 | 4/2010 | Berkman |
| 7,713,944 B2 | 5/2010 | Kinberger et al. |
| 7,740,847 B2 | 6/2010 | Allan et al. |
| 7,767,202 B2 | 8/2010 | Pardoll et al. |
| 7,767,803 B2 | 8/2010 | Diener et al. |
| 7,794,929 B2 | 9/2010 | Baylin et al. |
| 7,862,798 B2 | 1/2011 | Leamon et al. |
| 7,872,235 B2 | 1/2011 | Rousso et al. |
| 7,875,586 B2 | 1/2011 | Kovbasnjuk et al. |
| 7,879,981 B2 | 2/2011 | Obata et al. |
| 7,910,594 B2 | 3/2011 | Vlahov et al. |
| RE42,275 E | 4/2011 | Berkman |
| 7,990,533 B2 | 8/2011 | Maier et al. |
| 8,000,773 B2 | 8/2011 | Rousso et al. |
| 8,101,369 B2 | 1/2012 | Nam et al. |
| 8,101,713 B2 | 1/2012 | Cuello et al. |
| 8,105,568 B2 | 1/2012 | Vlahov et al. |
| 8,153,595 B2 | 4/2012 | Chen et al. |
| 8,211,401 B2 | 7/2012 | Babich et al. |
| 8,211,402 B2 | 7/2012 | Babich et al. |
| 8,211,473 B2 | 7/2012 | Troiano et al. |
| 8,211,635 B2 | 7/2012 | Barton |
| 8,227,634 B2 | 7/2012 | Pomper et al. |
| 8,236,330 B2 | 8/2012 | Zale et al. |
| 8,246,968 B2 | 8/2012 | Zale et al. |
| 8,258,111 B2 | 9/2012 | Shen et al. |
| 8,273,363 B2 | 9/2012 | Zale et al. |
| 8,313,728 B2 | 11/2012 | Leamon et al. |
| 8,388,977 B2 | 3/2013 | Low et al. |
| 8,404,817 B2 | 3/2013 | Sherman et al. |
| 8,414,898 B2 | 4/2013 | Afar et al. |
| 8,445,851 B2 | 5/2013 | Rousso et al. |
| 8,450,290 B2 | 5/2013 | Worm et al. |
| 8,465,725 B2 | 6/2013 | Babich et al. |
| 8,487,128 B2 | 7/2013 | Weissbach et al. |
| 8,487,129 B2 | 7/2013 | Babich et al. |
| 8,507,434 B2 | 8/2013 | Popel et al. |
| 8,557,772 B2 | 10/2013 | Popel et al. |
| 8,562,945 B2 | 10/2013 | Babich et al. |
| 8,603,499 B2 | 12/2013 | Zale et al. |
| 8,603,500 B2 | 12/2013 | Zale et al. |
| 8,603,501 B2 | 12/2013 | Zale et al. |
| 8,606,349 B2 | 12/2013 | Rousso et al. |
| 8,644,910 B2 | 2/2014 | Rousso et al. |
| 8,685,891 B2 | 4/2014 | Muraca |
| 8,703,918 B2 | 4/2014 | Colombatti et al. |
| 8,709,483 B2 | 4/2014 | Farokhzad et al. |
| 8,772,226 B2 | 7/2014 | Denmeade et al. |
| 8,772,459 B2 | 7/2014 | Ho et al. |
| 8,778,305 B2 | 7/2014 | Pomper et al. |
| 8,802,153 B2 | 8/2014 | Cheng et al. |
| 8,816,095 B2 | 8/2014 | Brown et al. |
| 8,834,842 B2 | 9/2014 | Leamon et al. |
| 8,840,865 B2 | 9/2014 | Babich et al. |
| 8,852,630 B2 | 10/2014 | Spiegel et al. |
| 8,859,509 B2 | 10/2014 | Spiegel et al. |
| 8,865,126 B2 | 10/2014 | Leamon et al. |
| 8,877,970 B2 | 11/2014 | Zimmerman et al. |
| 8,901,294 B2 | 12/2014 | Kim et al. |
| 8,907,058 B2 | 12/2014 | Low et al. |
| 8,916,167 B2 | 12/2014 | Low et al. |
| 8,926,944 B2 | 1/2015 | Babich et al. |
| 8,926,945 B2 | 1/2015 | Port et al. |
| 8,940,871 B2 | 1/2015 | Wu et al. |
| 8,946,388 B2 | 2/2015 | Sahin et al. |
| 8,962,799 B2 | 2/2015 | Babich et al. |
| 8,987,319 B2 | 3/2015 | Miller et al. |
| 9,044,468 B2 | 6/2015 | Pomper et al. |
| 9,056,841 B2 | 6/2015 | Pomper et al. |
| 9,193,763 B2 | 11/2015 | Low et al. |
| 9,226,981 B2 | 1/2016 | Pomper et al. |
| 9,242,012 B2 | 1/2016 | Ma et al. |
| 9,278,067 B2 | 3/2016 | Boulikas et al. |
| 9,295,727 B2 | 3/2016 | Zale et al. |
| 9,309,193 B2 | 4/2016 | Babich et al. |
| 9,636,413 B2 | 5/2017 | Vlahov et al. |
| 9,687,572 B2 | 6/2017 | Babich et al. |
| 9,951,324 B2 * | 4/2018 | Low .............. A61K 31/454 |
| 10,406,240 B2 * | 9/2019 | Low .............. A61K 47/64 |
| 2001/0031252 A1 | 10/2001 | Low et al. |
| 2002/0001782 A1 | 1/2002 | Watanabe et al. |
| 2002/0055121 A1 | 5/2002 | Vielkind et al. |
| 2002/0103136 A1 | 8/2002 | Feng et al. |
| 2002/0115596 A1 | 8/2002 | Garsky et al. |
| 2002/0132983 A1 | 9/2002 | Junghans et al. |
| 2003/0035804 A1 | 2/2003 | D'Amico et al. |
| 2003/0086900 A1 | 5/2003 | Low et al. |
| 2003/0133927 A1 | 7/2003 | DeFeo-Jones et al. |
| 2003/0138432 A1 | 7/2003 | Glazier et al. |
| 2003/0207808 A1 | 11/2003 | Savitzky et al. |
| 2003/0215456 A1 | 11/2003 | Yao et al. |
| 2003/0220241 A1 | 11/2003 | DeFeo-Jones et al. |
| 2003/0232760 A1 | 12/2003 | Garsky et al. |
| 2004/0001846 A1 | 1/2004 | Israeli et al. |
| 2004/0002478 A1 | 1/2004 | Kozikowski et al. |
| 2004/0018203 A1 | 1/2004 | Pastan et al. |
| 2004/0029778 A1 | 2/2004 | Isaacs et al. |
| 2004/0033195 A1 | 2/2004 | Leamon et al. |
| 2004/0052727 A1 | 3/2004 | Dalton et al. |
| 2004/0054190 A1 | 3/2004 | Pomper et al. |
| 2004/0058857 A1 | 3/2004 | Yao |
| 2004/0110723 A1 | 6/2004 | Frangioni et al. |
| 2004/0146516 A1 | 7/2004 | Roben et al. |
| 2004/0213791 A1 | 10/2004 | Bander et al. |
| 2004/0229845 A1 | 11/2004 | Frangioni et al. |
| 2004/0242582 A1 | 12/2004 | Green et al. |
| 2005/0002942 A1 | 1/2005 | Vlahov et al. |
| 2005/0107325 A1 | 5/2005 | Manoharan et al. |
| 2005/0119166 A1 | 6/2005 | Brady et al. |
| 2005/0158780 A1 | 7/2005 | Lupold et al. |
| 2005/0234247 A1 | 10/2005 | Klar et al. |
| 2005/0239138 A1 | 10/2005 | Hess et al. |
| 2005/0239739 A1 | 10/2005 | Matulic-Adamic |
| 2005/0245486 A1 | 11/2005 | Frangioni et al. |
| 2006/0024317 A1 | 2/2006 | Boyd et al. |
| 2006/0052312 A1 | 3/2006 | Erhardt et al. |
| 2006/0062793 A1 | 3/2006 | Webb et al. |
| 2006/0105975 A1 | 5/2006 | Pendergrast et al. |
| 2006/0106047 A1 | 5/2006 | Jiang et al. |
| 2006/0140871 A1 | 6/2006 | Sillerud et al. |
| 2006/0148718 A1 | 7/2006 | Brady et al. |
| 2006/0155021 A1 | 7/2006 | Lenges et al. |
| 2006/0155146 A1 | 7/2006 | Lenges et al. |
| 2007/0010014 A1 | 1/2007 | Wood et al. |
| 2007/0020327 A1 | 1/2007 | Fikes et al. |
| 2007/0031326 A1 | 2/2007 | Shirvan et al. |
| 2007/0031438 A1 | 2/2007 | Junghans et al. |
| 2007/0041901 A1 | 2/2007 | Diener et al. |
| 2007/0117153 A1 | 5/2007 | Bieniarz et al. |
| 2007/0128670 A1 | 6/2007 | Klatzmann et al. |
| 2007/0134332 A1 | 6/2007 | Turnell et al. |
| 2007/0142296 A1 | 6/2007 | McBride et al. |
| 2007/0148662 A1 | 6/2007 | Israeli et al. |
| 2007/0160617 A1 | 7/2007 | Ma et al. |
| 2007/0172422 A1 | 7/2007 | Glazier et al. |
| 2007/0179100 A1 | 8/2007 | Manoharan et al. |

(56) References Cited

U.S. PATENT DOCUMENTS

| | | |
|---|---|---|
| 2007/0219165 A1 | 9/2007 | Berkman et al. |
| 2007/0225213 A1 | 9/2007 | Kosak et al. |
| 2007/0244055 A1 | 10/2007 | Brady et al. |
| 2007/0254316 A1 | 11/2007 | Rodriguez et al. |
| 2007/0254317 A1 | 11/2007 | Busseret-Michel et al. |
| 2008/0008649 A1 | 1/2008 | Cappelletti |
| 2008/0008719 A1 | 1/2008 | Bowdish et al. |
| 2008/0089869 A1 | 4/2008 | Denmeade et al. |
| 2008/0114153 A1 | 5/2008 | Steeves et al. |
| 2008/0175789 A1 | 7/2008 | Frangioni et al. |
| 2008/0176821 A1 | 7/2008 | Kozikowski et al. |
| 2008/0193381 A1 | 8/2008 | Babich et al. |
| 2008/0214436 A1 | 9/2008 | Yu et al. |
| 2008/0248052 A1 | 10/2008 | Vlahov et al. |
| 2008/0269105 A1 | 10/2008 | Taft et al. |
| 2008/0311037 A1 | 12/2008 | Heston et al. |
| 2009/0117042 A1 | 5/2009 | Pomper et al. |
| 2009/0123467 A1 | 5/2009 | Bedi et al. |
| 2009/0180951 A1 | 7/2009 | Zimmerman et al. |
| 2009/0214636 A1 | 8/2009 | Low et al. |
| 2009/0247614 A1 | 10/2009 | Manoharan et al. |
| 2009/0258002 A1 | 10/2009 | Barrett et al. |
| 2009/0274625 A1 | 11/2009 | Denmeade et al. |
| 2010/0048490 A1 | 2/2010 | Vlahov et al. |
| 2010/0092496 A1 | 4/2010 | Boyd et al. |
| 2010/0178246 A1 | 7/2010 | Babich et al. |
| 2010/0183509 A1 | 7/2010 | Babich et al. |
| 2010/0183517 A1 | 7/2010 | Berkman et al. |
| 2010/0209343 A1 | 8/2010 | Bander et al. |
| 2010/0240701 A1 | 9/2010 | Vlahov et al. |
| 2010/0324008 A1 | 12/2010 | Low et al. |
| 2011/0008253 A1 | 1/2011 | Babich et al. |
| 2011/0027180 A1 | 2/2011 | Magnani et al. |
| 2011/0027274 A1 | 2/2011 | Cheng et al. |
| 2011/0064657 A1 | 3/2011 | Pomper et al. |
| 2011/0142760 A1 | 6/2011 | Pomper et al. |
| 2011/0172254 A1 | 7/2011 | Leamon et al. |
| 2011/0176998 A1 | 7/2011 | Pomper et al. |
| 2011/0200677 A1 | 8/2011 | Chandran et al. |
| 2011/0288152 A1 | 11/2011 | Low et al. |
| 2012/0009121 A1 | 1/2012 | Pomper et al. |
| 2012/0276162 A1 | 11/2012 | Zale et al. |
| 2012/0322741 A1 | 12/2012 | Low et al. |
| 2013/0034494 A1 | 2/2013 | Babich et al. |
| 2013/0172406 A1 | 7/2013 | Zale et al. |
| 2013/0336888 A1 | 12/2013 | Babich et al. |
| 2014/0107316 A1 | 4/2014 | Vlahov et al. |
| 2014/0140925 A1 | 5/2014 | Leamon et al. |
| 2014/0154702 A1 | 6/2014 | Parker et al. |
| 2014/0187501 A1 | 7/2014 | Bilodeau et al. |
| 2014/0314864 A1 | 10/2014 | Cheng et al. |
| 2015/0023875 A1 | 1/2015 | Farokhzad et al. |
| 2015/0079001 A1 | 3/2015 | Pomper et al. |
| 2015/0104387 A1 | 4/2015 | Pomper et al. |
| 2015/0110715 A1 | 4/2015 | Eder et al. |
| 2015/0246144 A1 | 9/2015 | Pomper et al. |
| 2015/0297735 A1 | 10/2015 | Vlahov et al. |
| 2015/0315196 A1 | 11/2015 | Howard et al. |
| 2015/0366968 A1 | 12/2015 | Basilion et al. |
| 2016/0067341 A1 | 3/2016 | Low et al. |
| 2016/0074526 A1 | 3/2016 | Bilodeau et al. |
| 2016/0114060 A1 | 4/2016 | Pomper et al. |
| 2016/0151508 A1 | 6/2016 | Low et al. |
| 2016/0220694 A1 | 8/2016 | Vlahov et al. |
| 2016/0287731 A1 | 10/2016 | Vlahov et al. |
| 2016/0361376 A1 | 12/2016 | Vlahov et al. |
| 2016/0361432 A1 | 12/2016 | Vlahov et al. |
| 2016/0361433 A1 | 12/2016 | Vlahov et al. |

FOREIGN PATENT DOCUMENTS

| | | | | |
|---|---|---|---|---|
| EP | 0116208 | 8/1984 | | |
| EP | 1177200 | 6/2005 | | |
| EP | 1472541 | 9/2009 | | |
| EP | 2170075 | 4/2010 | | |
| EP | 2318366 | 5/2011 | | |
| EP | 2136788 | 10/2011 | | |
| EP | 2373621 | 10/2011 | | |
| EP | 2389361 | 11/2011 | | |
| EP | 2644192 | 10/2013 | | |
| EP | 2644594 | 10/2013 | | |
| EP | 2648766 | 10/2013 | | |
| EP | 2436376 | 7/2014 | | |
| EP | 2759535 | 7/2014 | | |
| EP | 2240171 | 8/2014 | | |
| EP | 2823826 | 1/2015 | | |
| EP | 2097111 | 7/2015 | | |
| EP | 2921482 | 9/2015 | | |
| EP | 2938364 | 11/2015 | | |
| EP | 2942065 | 11/2015 | | |
| EP | 2958596 | 12/2015 | | |
| EP | 2993171 | 3/2016 | | |
| EP | 2706057 | 4/2016 | | |
| EP | 3038996 | 7/2016 | | |
| EP | 2408755 | 5/2017 | | |
| JP | 2002-506204 | 2/2002 | | |
| JP | 2004-536034 | 12/2004 | | |
| JP | 2005-274569 | 10/2005 | | |
| JP | 2006-501149 | 1/2006 | | |
| JP | 2006514961 | 5/2006 | | |
| JP | 2006-518712 | 8/2006 | | |
| JP | 2007-521803 | 8/2007 | | |
| JP | 2009-519209 A | 5/2009 | | |
| JP | 2010-515732 A | 5/2010 | | |
| JP | 2010-518112 A | 5/2010 | | |
| JP | 2011-132258 | 7/2011 | | |
| WO | WO 1988/001622 | 3/1988 | | |
| WO | WO 1991007418 | 5/1991 | | |
| WO | 1995033766 | 12/1995 | | |
| WO | WO 99/45374 | 9/1999 | | |
| WO | WO 2000/064911 | 11/2000 | | |
| WO | WO2000/066091 | 11/2000 | | |
| WO | WO 2002/043773 | 6/2002 | | |
| WO | WO 2002/062398 | 8/2002 | | |
| WO | WO 2002098885 | 12/2002 | | |
| WO | 2003/000201 | 1/2003 | | |
| WO | WO 2003060523 | 7/2003 | | |
| WO | WO 2003/092742 | 11/2003 | | |
| WO | WO 2003097647 | 11/2003 | | |
| WO | WO 2004/010957 | 2/2004 | | |
| WO | 2004069285 | 8/2004 | | |
| WO | WO 2004/069159 | 8/2004 | | |
| WO | WO 2005/082023 | 9/2005 | | |
| WO | WO 2006012527 | 2/2006 | | |
| WO | WO 2006/096754 | 9/2006 | | |
| WO | WO 2006093991 | 9/2006 | | |
| WO | WO 2006/136564 | 12/2006 | | |
| WO | 2007/006041 | 1/2007 | | |
| WO | WO 2007/022494 | 2/2007 | | |
| WO | WO 2007/042504 | 4/2007 | | |
| WO | WO 2007/106869 | 9/2007 | | |
| WO | WO 2008/058192 | 5/2008 | | |
| WO | WO 2008057437 | 5/2008 | | |
| WO | 2008/088648 | 7/2008 | | |
| WO | 2008/098112 | 8/2008 | | |
| WO | 2008/101231 | 8/2008 | | |
| WO | WO2009/026177 | 8/2008 | * | ........... A61K 39/395 |
| WO | WO 2008/121949 | 10/2008 | | |
| WO | WO 2009/002529 | 12/2008 | | |
| WO | WO 2009/026177 | 2/2009 | | |
| WO | WO 2009/070302 | 6/2009 | | |
| WO | 2009089383 | 7/2009 | | |
| WO | WO 2009082606 | 7/2009 | | |
| WO | WO 2009002993 | 12/2009 | | |
| WO | WO 2010/014933 | 2/2010 | | |
| WO | WO 2010/065899 | 6/2010 | | |
| WO | WO 2010/065902 | 6/2010 | | |
| WO | WO 2010/065906 | 6/2010 | | |
| WO | WO 2010/108125 | 9/2010 | | |
| WO | WO 2011/014821 | 2/2011 | | |
| WO | WO 2011/106639 | 9/2011 | | |
| WO | WO 2012/078534 | 6/2012 | | |
| WO | WO 2012/166923 | 12/2012 | | |
| WO | WO 2013/028664 | 2/2013 | | |

(56) References Cited

FOREIGN PATENT DOCUMENTS

| WO | WO 2013022797 | 2/2013 |
|---|---|---|
| WO | WO2013/130776 | 9/2013 |
| WO | 2014/062697 | 4/2014 |
| WO | WO 2014078484 | 5/2014 |
| WO | WO 2014/106208 | 7/2014 |
| WO | WO 2014/127365 | 8/2014 |
| WO | WO 2014/134543 | 9/2014 |
| WO | WO 2015/055318 | 4/2015 |
| WO | WO 2015/057250 | 4/2015 |
| WO | WO 2015/171792 | 11/2015 |
| WO | WO 2016/030329 | 3/2016 |
| WO | WO 2016/040179 | 3/2016 |

OTHER PUBLICATIONS

Muller C., et al. "Synthesis and in Vitro/in Vivo Evaluation of Novel $^{99m}$Tc(CO)$_3$-Folates," Bioconjugate Chem., 2006 vol. 17, p. 797-806.

Viola-Villegas N., et al. "Targeting Gallium to Cancer Cells through the Folate Receptor," Drug Target Insights, 2008 vol. 3, p. 13-25.

Viola-Villegas N., et al. "Targeting the Folate Receptor (FR): Imaging and Cytotoxicity of Re$^I$ Conjugates in FR-Overexpressing Cancer Cells," ChemMedChem, 2008 vol. 3, p. 1387-1394.

Zhou J., "In vivo evaluation of medical device-associated inflammation using macrophage-specific position emission tomography (PET) imaging," Bioorganic and Medicinal Chemistry Letters, 2013 vol. 23, p. 2044-2047.

Kularatne SA., et al. "Comparative Analysis of Folate Derived PET Imaging Agents with [$^{18}$F]-2-Fluoro-2-deoxy-D-glucose Using Rodent Inflammatory Paw Model," Molecular Pharmaceutics, 2013 vol. 10, p. 3103-3111.

Kothari et al., "$^{18}$F-labeled small molecule inhibitors of prostate specific membrane antigen (PSMA) for PET imaging of prostate cancer," J Nucl Med May 2012 vol. 53 No. supplement 1 1721.

Hillier et al., "[$^{131}$I] MIP-1466, a small molecule prostate-specific membrane antigen (PSMA) inhibitor for targeted radiotherapy of prostate cancer (PCa)," J Nucl Med May 2012 vol. 53 No. supplement 1 170.

Armor et al., "A comparison of 2D and 3D regions within the same patient to derive organ and tissue kinetics," J Nucl Med May 2012 vol. 53 No. supplement 1 13.

Afshar-Oromieh et al., "[$^{68}$Ga]Gallium-labelled PSMA ligand as superior PET tracer for the diagnosis of prostate cancer: comparison with $^{18}$F-FECH," Eur J Nucl Med Mol Imaging (2012) 39:1085-1086.

Afshar-Oromieh et al., "Comparison of PET/CT and PET/MRI hybrid systems using a $^{68}$Ga-labelled PSMA ligand for the diagnosis of recurrent prostate cancer: initial experience," Eur J Nucl Med Mol Imaging (2014) 41:887-897.

Afshar-Oromieh et al., "Comparison of PET imaging with a $^{68}$Ga-labelled PSMA ligand and $^{18}$F-choline-based PET/CT for the diagnosis of recurrent prostate cancer," Eur J Nucl Med Mol Imaging (2014) 41:11-20.

Afshar-Oromieh et al., "PET/MRI with a $^{68}$Ga-PSMA ligand for the detection of prostate cancer," Eur J Nucl Med Mol Imaging (2013) 40:1629-1630.

Afshar-Oromieh et al., "PET imaging with a [$^{68}$Ga]gallium-labelled PSMA ligand for the diagnosis of prostate cancer: biodistribution in humans and first evaluation of tumour lesions," Eur J Nucl Med Mol Imaging (2013) 40:486-495.

Afshar-Oromieh et al., "The diagnostic value of PET/CT imaging with the 68Ga-labelled PSMA ligand HBED-CC in the diagnosis of recurrent prostate cancer," Eur J Nucl Med Mol Imaging (2015) 42:197-209.

Aggarwal et al., "A Dimeric Peptide That Binds Selectively to Prostate-Specific Membrane Antigen and Inhibits its Enzymatic Activity," Cancer Res 2006; 66: 9171-9177, Sep. 15, 2006.

Alt et al., "High-Resolution Animal PET Imaging of Prostate Cancer Xenografts with Three Different $^{64}$Cu-Labeled Antibodies against Native Cell-Adherent PSMA," The Prostate 70:1413-1421 (2010).

Ananias et al., "Expression of the Gastrin-Releasing Peptide Receptor, the Prostate Stem Cell Antigen and the Prostate-Specific Membrane Antigen in Lymph Node and Bone Metastases of Prostate Cancer," The Prostate 69:1101-1108 (2009).

Anderson et al., "Substrate specificity of prostate-specific membrane antigen," Bioorganic & Medicinal Chemistry 15 (2007) 6678-6686.

Antunes et al., "PGC and PSMA in prostate cancer diagnosis: tissue analysis from biopsy samples," Int Braz J Urol. 2013; 39: 649-56.

Bacich et al., "Cloning, expression, genomic localization, and enzymatic activities of the mouse homolog of prostate-specific membrane antigen/NAALADase/folate hydrolase," Mammalian Genome 12, 117-123 (2001).

Baiz et al., "Synthesis and Characterization of a Novel Prostate Cancer-Targeted Phosphatidylinositol-3-kinase Inhibitor Prodrug," J. Med. Chem. 2012, 55, 8038-8046.

Banerjee et al., "$^{64}$Cu-Labeled Inhibitors of Prostate-Specific Membrane Antigen for PET Imaging of Prostate Cancer," J. Med. Chem. 2014, 57, 2657-2669.

Banerjee et al., "$^{68}$Ga-Labeled Inhibitors of Prostate-Specific Membrane Antigen (PSMA) for Imaging Prostate Cancer," J. Med. Chem. 2010, 53, 5333-5341.

Banerjee et al., "A Modular Strategy to Prepare Multivalent Inhibitors of Prostate-Specific Membrane Antigen (PSMA)," Oncotarget 2011; vol. 2, No. 12, 1244-1253.

Banerjee et al., "Effect of Chelators on the Pharmacokinetics of $^{99m}$Tc-Labeled Imaging Agents for the Prostate-Specific Membrane Antigen (PSMA)," J. Med. Chem. 2013, 56, 6108-6121.

Barinka et al., "A high-resolution structure of ligand-free human glutamate carboxypeptidase II," Acta Cryst. (2007). F63, 150-153.

Barinka et al., "Interactions between Human Glutamate Carboxypeptidase II and Urea-Based Inhibitors: Structural Characterization," J. Med. Chem. 2008, 51, 7737-7743.

Barinka et al., "Structural Insight into the Pharmacophore Pocket of Human Glutamate Carboxypeptidase II," J. Med. Chem. 2007, 50, 3267-3273.

Barrett et al., "First-in-Man Evaluation of 2 High-Affinity PSMA-Avid Small Molecules for Imaging Prostate Cancer," J Nucl Med. 2013;54:380-387.

Beheshti et al., "Prostate Cancer: Role of SPECT and PET in Imaging Bone Metastases," Semin Nucl Med 39:396-407.

Belloli et al., "Characterization of preclinical models of prostate cancer using PET-based molecular imaging," Eur J Nucl Med Mol Imaging (2009) 36:1245-1255.

Bostwick et al., "Prostate Specific Membrane Antigen Expression in Prostatic Intraepithelial Neoplasia and Adenocarcinoma," Cancer 1998;82:2256-61.

Bouchelouche et al., "'Image and treat': an individualized approach to urological tumors," Curr Opin Oncol 22:274-280.

Bouchelouche et al., "Imaging Prostate Cancer: An Update on Positron Emission Tomography and Magnetic Resonance Imaging," Curr Urol Rep (2010) 11:180-190.

Bouchelouche et al., "PET/CT Imaging and Radioimmunotherapy of Prostate Cancer," Semin Nucl Med 41:29-44.

Bouchelouche et al., "Positron emission tomography/computed tomography and radioimmunotherapy of prostate cancer," Curr Opin Oncol 21:469-474.

Bouchelouche et al., "Prostate Specific Membrane Antigen—A Target for Imaging and Therapy with Radionuclides," Discov Med. Jan. 2010 ; 9(44): 55-61.

Bzdega et al., "The cloning and characterization of a second brain enzyme with NAAG peptidase activity," Journal of Neurochemistry, 2004, 89, 627-635.

Ceci et al., "$^{11}$C-Choline PET/CT in patients with hormone-resistant prostate cancer showing biochemical relapse after radical prostatectomy," Eur J Nucl Med Mol Imaging (2013) 40:149-155.

Chandran et al., "Characterization of a targeted nanoparticle functionalized with a urea-based inhibitor of prostate-specific membrane antigen (PSMA)," Cancer Biology & Therapy, 7:6, 974-982.

(56) References Cited

OTHER PUBLICATIONS

Chang et al., "Five Different Anti-Prostate-specific Membrane Antigen (PSMA) Antibodies Confirm PSMA Expression in Tumor-associated Neovasculature," Cancer Research 59,3192-3198, Jul. 1, 1999.
Chang et al., "The clinical role of prostate-specific membrane antigen (PSMA)," Urologic Oncology 7 (2002) 7-12.
Chen et al., "2-(3-{1-Carboxy-5-[(6-[18F]Fluoro-Pyridine-3-Carbonyl)-Amino]-Pentyl}-Ureido)-Pentanedioic Acid, [18F]DCFPyL, a PSMA-Based PET Imaging Agent for Prostate Cancer," Clin Cancer Res; 17(24); 7645-53.
Chen et al., "A low molecular weight PSMA-based fluorescent imaging agent for cancer," Biochemical and Biophysical Research Communications 390 (2009) 624-629.
Chen et al., "PSMA-Targeted Theranostic Nanoplex for Prostate Cancer Therapy," ACS Nano 2012, vol. 6, No. 9, 7752-7762.
Chen et al., "Synthesis and Biological Evaluation of Low Molecular Weight Fluorescent Imaging Agents for the Prostate-Specific Membrane Antigen," Bioconjugate Chem. 2012, 23, 2377-2385.
Chopra A., "$^{68}$Ga-Labeled 2-[3-(1-carboxy-5-{7- [5-carboxy-5-(3-phenyl-2-{3-phenyl-2-[2-(4,7,10-tris-carboxymethyl-1,4,7,10-tetraazacyclododec-1-1)acetylamino]propionylamino}propionylamino)pentylcarbamoyl]heptanoylamino}pentyl)ureido]pentanedioic acid," Sep. 27, 2010 [Updated Dec. 28, 2010]. In: Molecular Imaging and Contrast Agent Database (MICAD) [Internet]. Bethesda (MD): National Center for Biotechnology Information (US); 2004-2013.
Chopra A, "$^{68}$Ga-Labeled 2-{3-[5-(7-{1-benzyloxycarbonyl-5-[2-(4,7,10-triscarboxymethyl-1,4,7,10-tetraazacyclododec-1-1)acetylamino]pentylcarbamoyl}-heptanoylamino)-1-carboxypentyl]ureido}pentanedioic acid," Sep. 28, 2010 [Updated Dec. 28, 2010]. In: Molecular Imaging and Contrast Agent Database (MICAD) [Internet]. Bethesda (MD): National Center for Biotechnology Information (US); 2004-2013.
Chuu et al., "Androgen suppresses proliferation of castrationresistant LNCaP 104-R2 prostate cancer cells through androgen receptor, Skp2, and c-Myc," Cancer Sci 2011; 102: 2022-2028.
Cimitan et al., "[18F]fluorocholine PET/CT imaging for the detection of recurrent prostate cancer at PSA relapse: experience in 100 consecutive patients," Eur J Nucl Med Mol Imaging (2006) 33:1387-1398.
ClinicalTrials.gov, "Pilot Study of 99mTc-MIP-1404 SPECT/CT Imaging in Men With Prostate Cancer Undergoing Prostatectomy and/or Pelvic Lymph Node Dissection," ClinicalTrials.gov Identifier: NCT01572701, available online at: https://clinicaltrials.gov/ct2/show/NCT01572701.
ClinicalTrials.gov, "A Phase 1 Pilot Study of 99mTc-MIP-1404 SPECT/CT Imaging to Histology in Men With Prostate Cancer," ClinicalTrials.gov Identifier: NCT01615406, available online at: https://clinicaltrials.gov/ct2/show/NCT01615406.
ClinicalTrials.gov, "99mTc-MIP-1404 for Imaging Prostate Cancer: Phase I Clinical Study to Assess the Image Quality of a Simplified Kit Formulation Compared to a Multi-step Preparation of 99mTc-MIP-1404," ClinicalTrials.gov Identifier: NCT01654874, available online at: https://clinicaltrials.gov/ct2/show/NCT01654874.
ClinicalTrials.gov, "A Phase 2 Study With MIP-1404 in Men With High-Risk PC Scheduled for RP and EPLND Compared to Histopathology," ClinicalTrials.gov Identifier: NCT01667536, available online at: https://clinicaltrials.gov/ct2/show/NCT01667536?id=NCT01667536.
Colabufo et al., "PB183, a sigma receptor ligand, as a potential PET probe for the imaging of prostate adenocarcinoma," Bioorganic & Medicinal Chemistry Letters 18 (2008) 1990-1993.
Cunha et al., "Tissue-specificity of prostate specific antigens: Comparative analysis of transcript levels in prostate and non-prostatic tissues," Cancer Letters 236 (2006) 229-238.
Dahl et al., "Sarcosine induces increase in HER2/neu expression in androgen-dependent prostate cancer cells," Mol Biol Rep (2011) 38:4237-4243.

DeGrado et al., "Synthesis and Evaluation of 18F-Labeled Choline Analogs as Oncologic PET Tracers," J Nucl Med 2001; 42:1805-1814.
DeGrado et al., "Synthesis and Evaluation of 18F-labeled Choline as an Oncologic Tracer for Positron Emission Tomography: Initial Findings in Prostate Cancer," Cancer Research 61,110-117, Jan. 1, 2000.
De Santis et al., "Rolle der Chemotherapie beim kastrationsresistenten Prostatakarzinom," Urologe 2012 • 51:39-43.
Dimitrakopoulou-Strauss et al., "PET Imaging of Prostate Cancer with $^{11}$C-Acetate," Nucl Med. 2003;44:556-558.
Dumas et al., "Molecular Expression of PSMA mRNA and Protein in Primary Renal Tumors," Int. J. Cancer: 80, 799-803 (1999).
Eder et al., "Pharmacokinetic Properties of Peptidic Radiopharmaceuticals: Reduced Uptake of (EH)3-Conjugates in Important Organs," Nucl Med 2013; 54:1-4.
Eder et al., "Novel Preclinical and Radiopharmaceutical Aspects of [68Ga]GA-PSMA-HBED-CC: A New PET Tracer for Imaging of Prostate Cancer," Pharmaceuticals 2014, 7, 779-796.
Eder et al., "Preclinical Evaluation of a Bispecific Low-Molecular HeterodimerTargeting Both PSMA and GRPR for Improved PET Imaging and Therapy of Prostate Cancer," The Prostate 74:659-668 (2014).
Eder et al., "PSMA as a target for radiolabelled small molecules," Eur J Nucl Med Mol Imaging (2013) 40:819-823.
Eiber et al., "$^{68}$Ga-PSMA PET/MR with multimodality image analysis for primary prostate cancer," Abdom Imaging (2015) 40:1769-1771.
Elsasser-Beile et al., "PET Imaging of Prostate Cancer Xenografts with a Highly Specific Antibody against the Prostate-Specific Membrane Antigen," J Nucl Med 2009; 50:606-611.
Elsasser-Beile et al., "Targeted Therapies for Prostate Cancer Against the Prostate Specific Membrane Antigen," Current Drug Targets, 2009, 10, 118-125.
Elsasser-Beile et al., "A New Generation of Monoclonal and Recombinant Antibodies Against Cell-Adherent Prostate Specific Membrane Antigen for Diagnostic and Therapeutic Targeting of Prostate Cancer," The Prostate 66:1359-1370 (2006).
El-Zaria et al., "Preparation and evaluation of carborane-derived inhibitors of prostate specific membrane antigen (PSMA)," Dalton Trans., 2014, 43, 4950-4961.
Emonds et al., "Do androgens control the uptake of $^{18}$F-FDG, $^{11}$C-choline and $^{11}$C-acetate in human prostate cancer cell lines?," Eur J Nucl Med Mol Imaging (2011) 38:1842-1853.
Eur J Nucl Med Mol Imaging (2012) 39 (Suppl 2):S304-S353. ISTARD Posters.
Evans et al., "Noninvasive measurement of androgen receptor signaling with a positron-emitting radiopharmaceutical that targets prostate-specific membrane antigen," PNAS, vol. 108, No. 23, 9578-9582, Jun. 7, 2011.
Fair et al., "Prostate-Specific Membrane Antigen," The Prostate 32:140-148 (1997).
Fall et al., "Prostate-Specific Antigen Levels as a Predictor of Lethal Prostate Cancer," J Natl Cancer Inst 2007;99: 526-32.
Fortmuller et al., "Effective Targeting of Prostate Cancer by Lymphocytes Redirected by a PSMA x CD3 Bispecific Single-Chain Diabody," The Prostate 71:588-596 (2011).
Fortuin et al., "Value of PET/CT and MR Lymphography in Treatment of Prostate Cancer Patients With Lymph Node Metastases," Int J Radiation Oncol Biol Phys, vol. 84, No. 3, pp. 712e718, 2012.
Foss et al., "GCPII Imaging and Cancer," Current Medicinal Chemistry, 2012, 19, 1346-1359.
Franc et al., "Detection and localization of carcinoma within the prostate using high resolution transrectal gamma imaging (TRGI) of monoclonal antibody directed at prostate specific membrane antigen (PSMA)—Proof of concept and initial imaging results," European Journal of Radiology 82 (2013) 1877-1884.
Frigerio et al., "A single-chain fragment against prostate specific membrane antigen as a tool to build theranostic reagents for prostate cancer," European Journal of Cancer (2013) 49, 2223-2232.

(56) References Cited

OTHER PUBLICATIONS

Ghosh et al., "Tumor Target Prostate Specific Membrane Antigen (PSMA) and its Regulation in Prostate Cancer," Journal of Cellular Biochemistry 91:528-539 (2004).
Giovacchini et al., "Predictive factors of [$^{11}$C]choline PET/CT in patients with biochemical failure after radical prostatectomy," Eur J Nucl Med Mol Imaging (2010) 37:301-309.
Goodman Jr. et al., "Interaction of prostate specific membrane antigen with clathrin and the adaptor protein complex-2," International Journal of Oncology 31: 1199-1203, 2007.
Graham et al., "Radiofluorinated Derivatives of 2-(Phosphonomethyl)pentanedioic Acid as Inhibitors of Prostate Specific Membrane Antigen (PSMA) for the Imaging of Prostate Cancer," J. Med. Chem. 2012, 55, 9510-9520.
Grant et al., "Prostate Specific Membrane Antigen (PSMA) Regulates Angiogenesis Independently of VEGF during Ocular Neovascularization," PLoS One 7(7): e41285.
Gregor et al., "Induction of autoantibodies to syngeneic prostate-specific membrane antigen by xenogeneic vaccination," Int. J. Cancer: 116, 415-421 (2005).
Haberkorn et al., "Mechanistic and high-throughput approaches for the design of molecular imaging probes and targeted therapeutics," Clin Transl Imaging (2014) 2:33-41.
Haffner et al., "Prostate-specific membrane antigen expression in the neovasculature of gastric and colorectal cancers," Human Pathology (2009) 40, 1754-1761.
Hain et al., "Positron emission tomography for urological tumours," BJU International, 92,159-164.
Hara, Toshihiko, "$^{11}$C-Choline and 2-Deoxy-2[$^{18}$F]Fluoro-D-Glucose in Tumor Imaging with Positron Emission Tomography," Molecular Imaging and Biology, 2002, vol. 4, No. 4, 267-273.
Harada et al., "Preparation of Asymmetric Urea Derivatives that Target Prostate-Specific Membrane Antigen for SPECT Imaging," J. Med. Chem. 2013, 56, 7890-7901.
Heidenreich, A., "Immuntherapie beim metastasierten Prostatakarzinom—brauchen wir diene wirklich?," Urologe 2012 • 51:32-38.
Henry et al., "A Prostate-Specific Membrane Antigen-Targeted Monoclonal Antibody—Chemotherapeutic Conjugate Designed for the Treatment of Prostate Cancer," Cancer Research 64, 7995-8001, November.
Hillier et al., "123I-MIP-1072, a Small-Molecule Inhibitor of Prostate-Specific Membrane Antigen, Is Effective at Monitoring Tumor Response to Taxane Therapy," 2011; 52:1087-1093.
Hillier et al., "99mTc-Labeled Small-Molecule Inhibitors of Prostate-Specific Membrane Antigen for Molecular Imaging of Prostate Cancer," J Nucl Med 2013; 1369-1376.
Hlouchova et al., "Biochemical characterization of human glutamate carboxypeptidase III," Journal of Neurochemistry, 2007, 101, 682-696.
Hlouchova et al., "GCPII Variants, Paralogs and Orthologs," Current Medicinal Chemistry, 2012, 19, 1316-1322.
Hlouchova et al., "Structural insight into the evolutionary and pharmacologic homology of glutamate carboxypeptidases II and III," FEBS Journal 276 (2009) 4448-4462.
Ho et al., "Molecular Imaging, Pharmacokinetics, and Dosimetry of $^{111}$In-AMBA in Human Prostate Tumor-Bearing Mice," Journal of Biomedicine and Biotechnology vol. 2011, Article ID 101497, 8 pages.
Holland et al., "$^{89}$Zr-DFO-J591 for ImmunoPET of Prostate-Specific Membrane Antigen Expression In Vivo," J Nucl Med 2010; 51:1293-1300.
Hong et al., "Positron emission tomography imaging of prostate cancer," Amino Acids (2010) 39:11-27.
Hospers et al., "PET Imaging of Steroid Receptor Expression in Breast and Prostate Cancer," Current Pharmaceutical Design, 2008, 14, 3020-3032.
Huang et al., "Improving the Biodistribution of PSMA-Targeting Tracers With Highly Negatively Charged Linker," The Prostate 74:702-713 (2014).
Huang et al., "PSMA-Targeted Stably Linked 'Dendrimer-Glutamate Urea-Methotrexate' as a Prostate Cancer Therapeutic," Biomacromolecules 2014, 15, 915-923.
Humblet et al., "High-affinity Near-infrared Fluorescent Small-molecule Contrast Agents for In Vivo Imaging of Prostate-specific Membrane Antigen," Molecular Imaging . vol. 4, No. 4, Oct. 2005, pp. 448-462.
Humblet et al., "Multivalent Scaffolds for Affinity Maturation of Small Molecule Cell Surface Binders and Their Application to Prostate Tumor Targeting," J. Med. Chem. 2009, 52, 544-550.
Husarik et al., "Evaluation of [$^{18}$F]-choline PET/CT for staging and restaging of prostate cancer," Eur J Nucl Med Mol Imaging (2008) 35:253-263.
Hwang et al., "Imaging Prostate Derived Tumors with PET and N-(3-[$^{18}$F]Fluoropropyl)putrescine," Nucl. Med. Biol. vol. 17, No. 6, pp. 525-532, 1990.
Hwang et al., "N-3-[$^{18}$F]Fluoropropylputrescine as Potential PET Imaging Agent for Prostate and Prostate Derived Tumors," J Nucl Med 30:1205-1210, 1989.
Igerc et al., "The value of $^{18}$F-Choline PET/CT in patients with elevated PSA-level and negative prostate needle biopsy for localisation of prostate cancer," Eur J Nucl Med Mol Imaging (2008) 35:976-983.
Jackson et al., "Design, Synthesis, and Biological Activity of a Potent Inhibitor of the Neuropeptidase N-Acetylated α-Linked Acidic Dipeptidase," J. Med. Chem. 1996, 39, 619-622.
Jadvar et al., "Glucose Metabolism of Human Prostate Cancer Mouse Xenografts," Molecular Imaging, vol. 4, No. 2, Apr. 2005, pp. 91-97.
Jadvar et al., "Imaging evaluation of prostate cancer with $^{18}$F-fluorodeoxyglucose PET/CT: utility and limitations," Eur J Nucl Med Mol Imaging (2013) 40 (Suppl 1):S5-S10.
Jadvar et al., "Molecular Imaging of Prostate Cancer: PET Radiotracers," AJR 2012; 199:278-291.
Jadvar et al., "Molecular imaging of prostate cancer with $^{18}$F-fluorodeoxyglucose PET," Nat. Rev. Urol. 6, 317-323 (2009).
Jambor et al., "Functional Imaging of Localized Prostate Cancer Aggressiveness Using $^{11}$C-Acetate PET/CT and $^1$H-MR Spectroscopy," J Nucl Med 2010; 51:1676-1683.
Jemaa et al., "A Comparison of the Biological Features of Prostate Cancer with (PSA+, PSMA+) Profile according to RKIP," BioMed Research International vol. 2013, Article ID 409179, 7 pages.
Jemaa et al., "A novel regulation of PSMA and PSA expression by Q640X AR in 22Rv1 and LNCaP prostate cancer cells," Cell Biol Int 37 (2013) 464-470.
Jemaa et al., "Cellular distribution and heterogeneity of PSA and PSMA expression in normal, hyperplasia and human prostate cancer," La Tunisie Medicale—2013 ; vol. 91 (n°07) : 458-463.
Kahn et al., "$^{111}$Indium-Capromab Pendetide in the Evaluation of Patients with Residual or Recurrent Prostate Cancer After Radical Prostatectomy," The Journal of Urology vol. 159, 2041-2047, Jun. 1998.
Kasperzyk et al., "Prostate-Specific Membrane Antigen Protein Expression in Tumor Tissue and Risk of Lethal Prostate Cancer," Cancer Epidemiol Biomarkers Prev; 22(12); 2354-63.
Kasten et al., "Targeting prostate cancer cells with PSMA inhibitor-guided gold nanoparticles," Bioorganic & Medicinal Chemistry Letters 23 (2013) 565-568.
Kim et al., "Tribody: Robust Self-Assembled Trimeric Targeting Ligands with High Stability and Significantly Improved Target-Binding Strength," Biochemistry 2013, 52, 7283-7294.
Kinoshita et al., "Expression of Prostate-Specific Membrane Antigen in Normal and Malignant Human Tissues," World J Surg (2006) 30: 628-636.
Klotz, Laurence, "Cancer overdiagnosis and overtreatment," Curr Opin Urol 2012, 22:203-209.
Klusak et al., "Reaction Mechanism of Glutamate Carboxypeptidase II Revealed by Mutagenesis, X-ray Crystallography, and Computational Methods," Biochemistry 2009, 48, 4126-4138.
Kosuri et al., "Review of Salvage Therapy for Biochemically Recurrent Prostate Cancer: The Role of Imaging and Rationale for

(56) References Cited

OTHER PUBLICATIONS

Systemic Salvage Targeted Anti-Prostate-SpecificMembrane Antigen Radioimmunotherapy," Advances in Urology vol. 2012, Article ID 921674, 8 pages.
Kotzerke et al., "PET for Prostate Cancer Imaging: Still a Quandary or the Ultimate Solution?," The Journal of Nuclear Medicine, vol. 43, No. 2, Feb. 2002.
Kovar et al., "Pharmacokinetic and Biodistribution Assessment of a Near Infrared-Labeled PSMA-Specific Small Molecule in Tumor-Bearing Mice," Prostate Cancer vol. 2014, Article ID 104248, 10 pages.
Krohn et al., "[$^{68}$Ga]PSMA-HBED uptake mimicking lymph node metastasis in coeliac ganglia: an important pitfall in clinical practice," Eur J Nucl Med Mol Imaging (2015) 42:210-214.
Kularatne et al., "Design, Synthesis, and Preclinical Evaluation of Prostate-Specific Membrane Antigen Targeted $^{99m}$Tc-Radioimaging Agents," Molecular Pharmaceutics vol. 6, No. 3, 790-800.
Kuru et al., "MRT-navigierte stereotaktische Prostatabiopsie," Urologe 2012 • 51:50-56.
Kwee et al., "$^{18}$F-choline PET/CT imaging of RECIST measurable lesions in hormone refractory prostate cancer," Ann Nucl Med (2009) 23:541-548.
Lambert et al., "Molecular Evolution of the Transferrin Receptor/ Glutamate Carboxypeptidase II Family," J Mol Evol (2007) 64:113-128.
Lapi et al., "Assessment of an 18F-Labeled Phosphoramidate Peptidomimetic as a New Prostate-Specific Membrane Antigen-Targeted Imaging Agent for Prostate Cancer," J Nucl Med 2009; 50:2042-2048.
Leek et al., "Prostate-specific membrane antigen: evidence for the existence of a second related human gene," British Journal of Cancer (1995) 72, 583-588.
Lees et al., "Active surveillance in prostate cancer: patient selection and triggers for intervention," Curr Opin Urol 2012, 22:210-215.
Lesche et al., "Preclinical evaluation of BAY 1075553, a novel $^{18}$F-labelled inhibitor of prostate-specific membrane antigen for PET imaging of prostate cancer," Eur J Nucl Med Mol Imaging (2014) 41:89-101.
Liu et al., "C-11 Choline PET/CT Imaging for Differentiating Malignant From Benign Prostate Lesions," Clin Nucl Med 2008;33: 671-676.
Liu et al., "Constitutive and Antibody-induced Internalization of Prostate-specific Membrane Antigen," Cancer Research 58, 4055-4060, Sep. 15, 1998.
Liu et al., "Functional prostate-specific membrane antigen is enriched in exosomes from prostate cancer cells," International Journal of Oncology 44: 918-922, 2014.
Liu et al., "Prolonged androgen deprivation leads to downregulation of androgen receptor and prostate-specific membrane antigen in prostate cancer cells," International Journal of Oncology 41: 2087-2092, 2012.
Liu et al., "Pseudoirreversible Inhibition of Prostate-Specific Membrane Antigen by Phosphoramidate Peptidomimetics," Biochemistry 2008, 47, 12658-12660.
Liu et al., "Targeting prostate cancer cells with a multivalent PSMA inhibitor-guided streptavidin conjugate," Bioorganic & Medicinal Chemistry Letters 22 (2012) 3931-3934.
Lord et al., "$^{18}$F-Fluorocholine integrated PET/MRI for the initial staging of prostate cancer," Eur J Nucl Med Mol Imaging (2011) 38:2288.
Liu et al., "A targeted low molecular weight near-infrared fluorescent probe for prostate cancer," Bioorganic & Medicinal Chemistry Letters 20 (2010) 7124-7126.
Luboldt et al., "Prostate Carcinoma: Diffusion-weighted Imaging as Potential Alternative to Conventional MR and $^{11}$C-Choline PET/CT for Detection of Bone Metastases," Radiology: vol. 249: No. 3—Dec. 2008.
Lutje et al., "Dual-Modality Image-Guided Surgery of Prostate Cancer with a Radiolabeled Fluorescent Anti-PSMA Monoclonal Antibody," J Nucl Med 2014; 55:995-1001.
Lutje et al., "Prospects in Radionuclide Imaging of Prostate Cancer," The Prostate 72:1262-1272 (2012).
Malik et al., "One pot radiofluorination of a new potential PSMA ligand [Al$^{18}$F]NOTA-DUPA-Pep," J. Label Compd. Radiopharm 2012, 55 320-325.
Malik et al., "Radiosynthesis of a new PSMA targeting ligand ([$^{18}$F]FPy-DUPA-Pep)," Applied Radiation and Isotopes 69 (2011) 1014-1018.
Mannweiler et al., "Heterogeneity of Prostate-Specific Membrane Antigen (PSMA) Expression in Prostate Carcinoma with Distant Metastasis," Pathol. Oncol. Res. (2009) 15:167-172.
Maresca et al., "Influence of functionalized chelators on affinity and pharmacokinetics of $^{99m}$Tc(CO)$_3$-labeled small molecules targeting prostate specific membrane antigen (PSMA)," J Nucl Med May 2010 vol. 51 No. supplement 2 250.
Matthies et al., "Imaging of prostate cancer metastases with $^{18}$F-fluoroacetate using PET/CT," Eur J Nucl Med Mol Imaging (2004) 31:797.
Mease et al., "PET Imaging in Prostate Cancer: Focus on Prostate-Specific Membrane Antigen," Current Topics in Medicinal Chemistry, 2013, 13, 951-962.
Meighan et al., "Recombinant Glutamate Carboxypeptidase II (Prostate Specific Membrane Antigen—PSMA)—Cellular Localization and Bioactivity Analyses," Journal of Protein Chemistry, vol. 22, No. 4, May 2003.
Meinhardt et al., "Laparoscopic Sentinel Lymph Node Biopsy for Prostate Cancer: The Relevance of Locations Outside the Extended Dissection Area," Prostate Cancer vol. 2012, Article ID 751753, 4 pages.
Mertens et al., "PET with $^{18}$F-labelled choline-based tracers for tumour imaging: a review of the literature," Eur J Nucl Med Mol Imaging (2010) 37:2188-2193.
Mhawech-Fauceglia et al., "Prostate-specific membrane antigen (PSMA) protein expression in normal and neoplastic tissues and its sensitivity and specificity in prostate adenocarcinoma: an immunohistochemical study using mutiple tumour tissue microarray technique," Histopathology 2007, 50, 472-483.
Milowsky et al., "Phase I Trial of Yttrium-90-Labeled Anti-Prostate-Specific Membrane Antigen Monoclonal Antibody J591 for Androgen-Independent Prostate Cancer," J Clin Oncol 22:2522-2531.
Minner et al., "High Level PSMA Expression Is Associated With Early PSA Recurrence in Surgically Treated Prostate Cancer," The Prostate 71:281-288 (2011).
Mlcochova et al., "Mapping of the active site of glutamate carboxypeptidase II by site-directed mutagenesis," FEBS Journal 274 (2007) 4731-4741.
Moltzahn et al., "Die ossäre Metastasierung des Prostatakarzinoms," Urologe 2012 • 51:20-26.
Morris et al., "$^{11}$C-acetate PET imaging in prostate cancer," Eur J Nucl Med Mol Imaging (2007) 34:181-184.
Murphy et al., "Current Evaluation of the Tissue Localization and Diagnostic Utility of Prostate Specific Membrane Antigen," Cancer 1998;83:2259-69.
Nedrow-Byers et al., "A Phosphoramidate-Based Prostate-Specific Membrane Antigen-Targeted SPECT Agent," The Prostate 72:904-912 (2012).
Office Action (English translation) in Chinese Patent Application No. 201610184873, dated Jul. 24, 2018 (6 pages).
Oehr et al., "Imaging of prostate cancer," Curr Opin Oncol 19:259-264.
O'Keefe et al., "Comparative Analysis of Prostate-Specific Membrane Antigen (PSMA) Versus a Prostate-Specific Membrane Antigen-Like Gene," The Prostate 58:200-210 (2004).
Omlin et al., "Androgen- und Östrogen-biosynthesehemmer beim kastrationsresistenten Prostatakarzinom," Urologe 2012 • 51:8-14.
Osborne et al., "A Prospective Pilot Study of 89Zr-J591/Prostate Specific Membrane Antigen Positron Emission Tomography in Men with Localized Prostate Cancer Undergoing Radical Prostatectomy," The J Urol, 2014.
Oyama et al., "$^{11}$C-Acetate PET Imaging of Prostate Cancer," J Nucl Med 2002; 43:181-186.

(56) References Cited

OTHER PUBLICATIONS

Oyama et al., "$^{11}$C-Acetate PET Imaging of Prostate Cancer: Detection of Recurrent Disease at PSA Relapse," J Nucl Med 2003; 44:549-555.
Oyama et al., "PET Imaging in Prostate Cancer," Hinyokika Kiyo 52: 503-505, 2006.
Office Action in European Patent Application No. 2014002808, dated Sep. 7, 2018 (3 pages).
Parker et al., "Design, production, and characterization of a single-chain variable fragment (ScFv) derived from the prostate specific membrane antigen (PSMA) monoclonal antibody J591," Protein Expression and Purification 89 (2013) 136-145.
Pavlicek et al., "Glutamate Carboxypeptidase II: An Overview of Structural Studies and Their Importance for Structure-Based Drug Design and Deciphering the Reaction Mechanism of the Enzyme," Current Medicinal Chemistry, 2012,19,1300-1309.
Pavlicek et al., "Structural characterization of PI'-diversified urea-based inhibitors of glutamate carboxypeptidase II," Bioorganic & Medicinal Chemistry Letters 24 (2014) 2340-2345.
Perner et al., "Prostate-specific membrane antigen expression as a predictor of prostate cancer progression," Human Pathology (2007) 38,696-701.
Pillarsetty et al., "2-$^{18}$F-Fluoropropionic Acid as a PET Imaging Agent for Prostate Cancer," J Nucl Med 2009; 50:1709-1714.
Pinto et al., "Imaging in Prostate Cancer Staging: Present Role and Future Perspectives," Urol Int 2012;88: 125-136.
Ponde et al., "$^{18}$F-Fluoroacetate: A Potential Acetate Analog for Prostate Tumor Imaging—In Vivo Evaluation of $^{18}$F-Fluoroacetate Versus $^{11}$C-Acetate," J Nucl Med 2007; 48:420-428.
Poster. James, Shelly, "Urea based rhenium tricarbonyl dipeptide compounds as potential radiopharmaceuticals for PSMA imaging." INOR258.
Poulsen et al., "[$^{18}$F]-fluorocholine positron-emission/computed tomography for lymph node staging of patients with prostate cancer: preliminary results of a prospective study," BJU International, 106, 639-644.
Poulsen et al., "[$^{18}$F] fluoromethylcholine (FCH) positron emission tomography/computed tomography (PET/CT) for lymph node staging of prostate cancer: a prospective study of 210 patients," BJU International, 110, 1666-1671.
Preusser et al., "Kastrationsresistentes Prostatakarzinom," Urologe 2012 • 51:27-31.
Rais et al., "Bioanalytical method for evaluating the pharmacokinetics of the GCP-II inhibitor 2-phosphonomethylpentanedioicacid (2-PMPA)," Journal of Pharmaceutical and Biomedical Analysis 88 (2014) 162-169.
Rajasekaran et al., "A Novel Cytoplasmic Tail MXXXL Motif Mediates the Internalization of Prostate-specific Membrane Antigen," Molecular Biology of the Cell, vol. 14, 4835-4845, Dec. 2003.
Reske et al., "[$^{11}$C]choline PET/CT imaging in occult local relapse of prostate cancer after radical prostatectomy," Eur J Nucl Med Mol Imaging (2008) 35:9-17.
Reske et al., "[$^{11}$C]Choline uptake with PET/CT for the initial diagnosis of prostate cancer: relation to PSA levels, tumour stage and anti-androgenic therapy," Eur J Nucl Med Mol Imaging (2008) 35:1740-1741.
Reske et al., "Weiterentwicklung der PET und des PET/CT beim Prostatakarzinom," Urologe 2006 • 45:707-714.
Reske et al., "Nuklearmedizinische Diagnostik beim Prostatakarzinom," Urologe 2007 • 46:1485-1499.
Reske et al., "PET und PET/CT in der Rezidivdiagnostik des Prostatakarzinoms," Urologe 2006 • 45:1240-1250.
Rinnab et al., "[$^{11}$C]Choline PET/CT for Targeted Salvage Lymph Node Dissection in Patients with Biochemical Recurrence after Primary Curative Therapy for Prostate Cancer," Urol Int 2008;81:191-197.
Rinnab et al., "[$^{11}$C]choline PET/CT in prostate cancer patients with biochemical recurrence after radical prostatectomy," World J Urol (2009) 27:619-625.
Rioja et al., "Role of positron emission tomography in urological oncology," BJU International, 106, 1578-1594.
Ristau et al., "The prostate-specific membrane antigen: Lessons and current clinical implications from 20 years of research," Urologic Oncology: Seminars and Original Investigations 32 (2014) 272-279.
Roethke et al., "Hyrbid Positron Emission Tomography-Magnetic Resonance Imaging with Gallium 68 Prostate-specific Membrane Antigen Tracer: A Next Step for Imaging of Recurrent Prostate Cancer—Preliminary Results," European Urology 64 (2013) 862-864.
Rybalov et al., "Impact of total PSA, PSA doubling time and PSA velocity on detection rates of $^{11}$C-Choline positron emission tomography in recurrent prostate cancer," World J Urol (2013) 31:319-323.
Sacha et al., "Expression of Glutamate Carboxypeptidase II in Human Brain," Neuroscience 144 (2007) 1361-1372.
Scattoni et al., "Detection of Lymph-Node Metastases with Integrated [11C]Choline PET/CT in Patients with PSA Failure after Radical Retropubic Prostatectomy: Results Confirmed by Open Pelvic-Retroperitoneal Lymphadenectomy," European Urology 52 (2007) 423-429.
Scheffel et al., "PET Imaging of GRP Receptor Expression in Prostate Cancer," The Journal of Nuclear Medicine, vol. 45, No. 8, Aug. 2004.
Scher et al., "PET/CT imaging of recurrent prostate cancer," Eur J Nucl Med Mol Imaging (2008) 35:5-8.
Shvarts et al., "Positron Emission Tomography in Urologic Oncology," Cancer Control, Jul./Aug. 2002, vol. 9, No. 4, 335-342.
Silver et al., "Prostate-specific Membrane Antigen Expression in Normal and Malignant Human Tissues," Clinical Cancer Research, vol. 3, 81-85, Jan. 1997.
Simone et al., "What's in a Label? Radioimmunotherapy for Metastatic Prostate Cancer," Clin Cancer Res; 19(18); 4908-10.
Slusher et al., "Immunocytochemical Localization of the N-Acetyl-Aspartyl-Glutamate (NAAG) Hydrolyzing Enzyme N-Acetylated α-Linked Acidic Dipeptidase (NAALADase)," The Journal of Comparative Neurology 315:217-229 (1992).
Slusher et al., "Selective inhibition of NAALADase, which converts NAAG to glutamate, reduces ischemic brain injury," Nature Medicine, vol. 5, No. 12, Dec. 1999.
Soloviev et al., "PET imaging with 11C-acetate in prostate cancer: a biochemical, radiochemical and clinical perspective," Eur J Nucl Med Mol Imaging (2008) 35:942-949.
Spahn et al., "Wie soll die Hormontherapie beim kastrationsresistenten Prostatakarzinom fortgeführt werden?," Urologe 2012 • 51:15-19.
Sweat et al., "Prostate-Specific Membrane Antigen Expression Is Greatest in Prostate Adenocarcinoma and Lymph Node Metastases," Urology 52: 637-640, 1998.
Tang et al., "Prostate targeting ligands based on N-acetylated α-linked acidic dipeptidase," Biochemical and Biophysical Research Communications 307 (2003) 8-14.
Tang et al., "Updated Application of Prostate-Specific Membrane Antigen to the Diagnosis and Treatment of Prostate Cancer," National Journal of Anthology, vol. 14, No. 1, Jan. 2008.
Taylor et al., "Prostate Cancer Targeting Motifs: Expression of anb3, Neurotensin Receptor 1,Prostate Specific Membrane Antigen, and Prostate Stem Cell Antigen in Human Prostate Cancer Cell Lines and Xenografts," The Prostate 72:523-532 (2012).
Testa et al., "Prostate Cancer: Sextant Localization with MR Imaging, MR Spectroscopy, and $^{11}$C-Choline PET/CT," Radiology: vol. 244: No. 3—Sep. 2007.
Thalmann, G., "Fortgeschrittenes Prostatakarzinom," Urologe 2012 • 51:7.
Tykvart et al., "Rational design of urea-based glutamate carboxypeptidase II (GCPII) inhibitors as versatile tools for specific drug targeting and delivery," Bioorganic & Medicinal Chemistry 22 (2014) 4099-4108.
Uprimny et al., "$^{68}$Ga-PSMA ligand PET versus 18F-NaF PET: evaluation of response to 223Ra therapy in a prostate cancer patient," Eur J Nucl Med Mol Imaging (2015) 42:362-363.

(56) References Cited

OTHER PUBLICATIONS

Vallabhajosula et al., "Radioimmunotherapy of Prostate Cancer in Human Xenografts Using Monoclonal Antibodies Specific to Prostate Specific Membrane Antigen (PSMA): Studies in Nude Mice," The Prostate 58:145-155 (2004).
Vavere et al., "1-11C-Acetate as a PET Radiopharmaceutical for Imaging Fatty Acid Synthase Expression in Prostate Cancer," J Nucl Med 2008; 49:327-334.
Wang et al., "Bioisosterism of urea-based GCPII inhibitors: Synthesis and structure-activity relationship studies," Bioorganic & Medicinal Chemistry Letters 20 (2010) 392-397.
Wang et al., "Development of Targeted Near-Infrared Imaging Agents for Prostate Cancer," Mol Cancer Ther; 13(11); 2595-606.
Weineisen et al., "Synthesis and preclinical evaluation of DOTAGA-conjugated PSMA ligands for functional imaging and endoradiotherapy of prostate cancer," EJNMMI Research 2014, 4:63.
Weissbach, L. "Welche Inhalte sollte eine „living guideline besetzen?," Urologe 2012 • 51:57-59.
Whitaker et al., "N-acetyl-L-aspartyl-L-glutamate peptidase-like 2 is overexpressed in cancer and promotes a pro-migratory and pro-metastatic phenotype," Oncogene (2014) 33, 5274-5287.
Wiehr et al., "Pharmacokinetics and PET Imaging Properties of Two Recombinant Anti-PSMA Antibody Fragments in Comparison to their Parental Antibody," The Prostate 74:743-755 (2014).
Wright et al., "Expression of Prostate-Specific Membrane Antigen in Normal, Benign, and Malignant Prostate Tissues," Urol Oncol 1995;1:18-28.
Wu et al., "The molecular pruning of a phosphoramidate peptidomimetic inhibitor of prostate-specific membrane antigen," Bioorganic & Medicinal Chemistry 15 (2007) 7434-7443.
Yamaguchi et al., "Prostate cancer: a comparative study of $^{11}$C-choline PET and MR imaging combined with proton MR spectroscopy," Eur J Nucl Med Mol Imaging (2005) 32:742-748.
Zaheer et al., "New Agents and Techniques for Imaging Prostate Cancer," J Nucl Med 2009; 50:1387-1390.
Zechmann et al., "Radiation dosimetry and first therapy results with a 124I/131 I-labeled small molecule (MIP-1095) targeting PSMA for prostate cancer therapy," Eur J Nucl Med Mol Imaging (2014) 41:1280-1292.
Zhang et al., "A Remote Arene-Binding Site on Prostate Specific Membrane Antigen Revealed by Antibody-Recruiting Small Molecules," J. Am. Chem. Soc. 2010, 132, 12711-12716.
Zhang et al., "Prostate Specific Membrane Antigen (PSMA): A Novel Modulator of p38 for Proliferation, Migration, and Survival in Prostate Cancer Cells," The Prostate 73:835-841 (2013).
Hara et al., "Development of $^{18}$F-Fluoroethylcholine for Cancer Imaging with PET: Synthesis, Biochemistry, and Prostate Cancer Imaging," J Nucl Med 2002; 43:187-199.
Hara et al., "PET Imaging of Prostate Cancer Using Carbon-11-Choline," J Nucl Med 1998;39:990-995.
Examination report No. 1 for Australian Patent Application 2018200419, dated Oct. 24, 2018.
Office action in JP 2017-210775, dated Oct. 26, 2018.
Office action in Eurasian Patent Application 201690495/28, dated Dec. 20, 2018.
De Santis et al., "Role of Chemotherapy in Castration Resistant Prostate Cancer," English translation. Urologe 2012 • 51:39-43.
Heidenreich, A., "Immunotherapy for Metastatic Prostate Cancer—Do We Really Need This?," English translation. Urologe 2012 • 51:32-38.
Kuru et al., "MRI Navigated Stereotactic Prostate Biopsy," English Translation. Urologe 2012 • 51:50-56.
Moltzahn et al., "Bone Metastasis in Prostate Cancer," English translation. Urologe 2012 • 51:20-26.
Omlin et al., "Inhibitors of Androgen and Estrogen Biosynthesis in Castration-Resistant Prostate Cancer," English translation. Urologe 2012 • 51:8-14.
Preusser et al., "Castration-Resistant Prostate Cancer," English translation. Urologe 2012 • 51:27-31.
Reske et al., "Advancement of PET and PET/CT in Prostate Carcinoma," English translation. Urologe 2006 • 45:707-714.
Reske et al., "Nuclear Imaging of Prostate Cancer," English translation. Urologe 2007 • 46:1485-1499.
Reske et al., "PET and PET/CT in Relapsing Prostate Carcinoma," English translation. Urologe 2006 • 45:1240-1250.
Spahn et al., "How Shold Hormone Therapy for Castration-Resistant Prostate Cancer be Continued?," English translation. Urologe 2012 • 51:15-19.
Reske et al., "PET und PET/CT in Relapsing Prostate Carcinoma," English translation. Urologe 2006 • 45:1240-1250.
Thalmann, G., "Advanced Prostate Cancer," English translation. Urologe 2012 • 51:7.
Weissbach, L. "Which Components Should 'Living Guidelines' Contain?," English translation. Urologe 2012 • 51:57-59.
Office Action in CA 2924360 dated Jan. 11, 2018.
Office Action in CL 201600883 dated Apr. 12, 2018.
Office Action in CN 201480056250.5 dated Aug. 15, 2018.
Office Action in EA 201690495/28 dated Feb. 10, 2017.
Office Action in GE 2014014132 dated Feb. 2017.
Office Action in GE 2014014132 dated Mar. 2017.
Office Action in KR 10-2016-7012314 dated Mar. 6, 2017.
Office Action in KR 10-2016-7012314 dated Oct. 14, 2017.
Office Action in KR 10-2016-7012314 dated May 2, 2018.
Saudi Arabia First Examination Report.
Office Action in CL 201600883 dated Jan. 16, 2019.
Divyya et al., "GCPII modulates oxidative stress and prostate cancer susceptibility through changes in methylation of RASSF1, BNIP3, GSTP1 and Ec-SOD", Mol Biol Rep (2013) 40:5541-5550.
DNA Interactive Agents, Chapter 6, pp. 386-485.
Drug Discovery General References pp. 98-184.
Drug Metabolism Chapters 7-8, pp. 486-592.
Enzymes, Chapter 4, pp. 186-285.
Enzyme Inhibition, Chapter 5, pp. 286-385.
Office Action in GA AP2014014132 dated Jan. 11, 2019.
Office Action in ID P00201603202 dated Jan. 28, 2019.
Office Action in IL 245113 dated Jan. 10, 2019.
International Search Report and Written Opinion for PCT/US08/73375 dated Nov. 17, 2008.
International Search Report and Written Opinion for PCT/US11/26238 dated Apr. 27, 2011.
International Search Report and Written Opinion for PCT/US13/70007 dated Mar. 5, 2014.
International Search Report and Written Opinion for PCT/US16/12653 dated Mar. 11, 2016.
International Search Report and Written Opinion for PCT/US09/61049 dated Mar. 24, 2010.
International Search Report and Written Opinion for PCT/US09/61067 dated Jun. 17, 2010.
International Search Report and Written Opinion for PCT/US14/65467 dated Apr. 15, 2015.
Meienhofer et al., "Solid-Phase Synthesis with Attachment of Peptide to Resin through an Amino Acid Side Chain: [8-Lysine]-Vasopressin", Proc Nat. Acad. Sci. USA, vol. 68, No. 5, pp. 1006-1009, May 1971.
Nedrow-Byers et al., "PSMA-argeted SPECT Agents: Mode of Binding Effect on In Vitro Performance", The Prostate 73: 355-362 (2013).
Rong et al., "Molecular Modeling of the Interaction of Glutamate Carboxypeptidase II with Its Potent NAAG-Based Inhibitors", J. Med. Chem. 2002, 45, 4140-4152.
Wu et al., "A mild deprotection procedure for tert-butyl esters and tert-butyl ethers using $ZnBr_2$ in methylene chloride", Tetrahedron Letters 41 (2000) 2847-2849.
European Search Report in EP 18175078.7 dated Sep. 14, 2018.
Dusich et al., "General Approach for the Preparation of Fluorescent PSMA/GCPII Inhibitors", Abstract. Abstract ID: 470, Poster board space: 29. Jul. 2006.
Foss et al., "Synthesis and Validation of a Novel Small-Molecule Fluorescent Probe for PSMA Expression in Human Tumor Ncovasculature" Abstract. Abstract ID: 362. Jul. 2005.
PCT International Search Report/Written Opinion for PCT/US2009/061067, completed May 28, 2010.

(56) References Cited

OTHER PUBLICATIONS

PCT International Search Report for PCT/US2008/073375 dated Oct. 26, 2008.
PCT International Search Report for PCT/US2016/012653 dated Mar. 11, 2016.
Davis, Mindy I., et al., "Crystal Structure of Prostate-Specific Membrane Antigen, A Tumor Marker and Peptidase", Apr. 26, 2005, PNAS, vol. 102, No. 17, pp. 5981-5986.
Jackson, Paul F., et al., "Design of NAALADase Inhibitors: A Novel Neuroprotective Strategy", 2001, Current Medicinal Chemistry, vol. 8, No. 8, pp. 949-957.
Kozikowski, Alan P., et al., "Design of Remarkably Simple, Yet Potent Urea-Based Inhibitors of Glutamate Carbozypeptidase II (NAALADase)" 2, 2001, Journal of Medicinal Chemistry, vol. 44, No. 3, pp. 298-301.
Kozikowski, Alan P., et al., "Synthesis of Urea-Based Inhibitors as Active Site Probes of Glutamate Carboxypeptodase II: Efficacy as Analgesic Agents", 2004, Journal of Medicinal Chemistry, vol. 47, No. 7, pp. 1729-1738.
Majer, Pavel., et al., "Synthesis and Biological Evaluation of Thiol-Based Inhibitors of Glutamate Carboxypeptodase II: Discovery of an Orally Active GCP II Inhibitor", 2003, Journal of Medicinal Chemistry, vol. 46, No. 10, pp. 1989-1996.
Mesters, et al., et al., "Structure of Glutamate Carboxypeptidase II, a Drug Target in Neuronal Damage and Prostate Cancer" 2, 2006, The EMBO Journal, vol. 25, No. 6, pp. 1375-1384.
Ranasinghe, M. G., et al., "Facile Synthesis of Unsymmetrical Thiolsulfonates via Sulfonylation of Mercaptans", 1988, Synthetic Communications, vol. 18, No. 3, pp. 227-232.
Olsnes, S., et al., Immunology Today, 10, pp. 291-295 (1989).
Melby, et at., Cancer Research 53(8), pp. 1755-1760 (1993).
Truffert, et al., Tetrahedron, 52:3005 (1996).
Martin, et al., Helv. Chim. Acta, 78, 486-504 (1995) and Abstract.
Lupold, et al., "Identification and characterization of nuclease-stabilized RNA molecules that bind human prostate cancer cells via the prostate-specific membrane antigen." Cancer Res. 2002; 62:4029-4033.
Farokhzad, et al., "Nanoparticle-Aptamer Bioconjugates: A New Approach for Targeting Prostate Cancer Cells," Cancer Research 64, pp. 7668-7672 (2004).
PCT International Search Report/Written Opinion for PCT/US2009/061049, completed Mar. 15, 2010.
Jayaprakash, Sarva, et al. "Design and synthesis of a PSMA inhibitor—doxorubicin conjugate for targeted prostate cancer therapy." ChemMedChem 1.3 (2006): 299-302.
PCT International Search Report and Written Opinion for PCT/US2011/026238, dated Apr. 27, 2011.
Foss, Catherine A., et al. "Radiolabeled small-molecule ligands for prostate-specific membrane antigen: in vivo imaging in experimental models of prostate cancer." *Clinical cancer research* 11.11 (2005): 4022-4028.
McNamara et al, Cell type specific delivery of siRNAs with aptamer-siRNA chimeras, Nature Biotechnolgy, 2006; 24: 1005-1015.
Gomez-Hens et al., "Long wavelength fluorophores: new trends in their analytical use," *Trends in Analytical Chemistry*, 2004; 23:127-136.
Definition of ligand, Random House Kernerman Webster's College Dictionary, downloaded on Jan. 25, 2014 from http://www.thefreedictionary.com/ligand, 1 page.
Eder et al., 68Ga-complex lipophilicity and the targeting property of a urea-based PSMA inhibitor for PET imaging, *Bioconjugate Chemistry*, 2012; 23:688-697.
Pubchem, Compound summary for: CID 58099954, Aug. 19, 2012.
Peltier et al., "The Total Synthesis of Tubulysin D," J. Am. Chem. Soc. 128:16018-19 (2006).
Pathak et al., Enzymic protecting group techniques in organic synthesis, Stereosel. Biocatal. 775-797 (2000).
Silverman, "The Organic Chemistry of Drug Design and Drug Action," Elsevier Academic Press (2nd Ed. 2003).
Larock, "Comprehensive Organic Transformations, a guide to functional group preparations," VCH Publishers, Inc. New York (1989).
Theodora E. Greene & Peter G.M. Wuts, "Protective Groups ion Organic Synthesis," 2d edition, John Wiley & Sons, Inc. New York (1991).
Vlahov, et al., "Design and regioselective synthesis of a new generation of targeted chemotherapeutics. Part 1: EC145, a folic acid conjugate of desacetylvinblastine monohydrazide," ScienceDirect, Bioorganic & Medical Chemistry Letters 16 (2006) 5093-5096.
Paranjpe, et al., "Tumor-targeted bioconjugate based delivery of camptothecin: design, synthesis and in vitro evaluation," ScienceDirect Journal of Controlled Release 100 (2004) 275-292.
Yang, et al., "Characterization of the pH of Folate Receptor-Containing Endosomes and the Rate of Hydrolysis of Internalized Acid-Labile Folate-Drug Conjugates," JPET 321: 462-468, 2007.
Henne, et al., "Synthesis and activity of a folate peptide camptothecin prodrug," ScienceDirect, Bioorganic & Medical Chemistry Letters 16 (2006) 5350-5355.
Roy, et al., "DUPA Conjugation of a Cytotoxic Indenoisoquinoline Topoisomerase I Inhibitor for Selective Prostate Cancer Cell Targeting," J. Med. Chem. 58 (2015) 3094-3103.
Kularatne, S., "Synthesis and Biological Analysis of Prostate-Specific Membrane Antigen-Targeted Anticancer Prodrugs," J. Med. Chem, 2010, 53(21), 7767-7777.
PCT International Search Report and Written Opinion for PCT/US2013/070007, dated Mar. 5, 2014.
Banerjee, S. et al., "Sequential SPECT and Optical Imaging of Experimental Models of Prostate Cancer with a Dual Modality Inhibitor of the Prostate-Specific Membrane Antigen," Angewandte Chemie International Edition, 2011, 50, 9167-9170.
Lu, G. et al., "Synthesis and SAR of $^{99m}$Tc/Re-labeled small molecule prostate specific membrane antigen inhibitors with novel polar chelates," Bioorganic and Medicinal Chemistry Letters, 2013, 23, 1557-1563.
Kaur, G. et al., "Biological evaluation of tubulysin A: a potential anticancer and antiangiogenic natural product," Biochem. J., 2006, 396, 235-242.
Bennett, V.J., "Analysis of fluorescently labeled substance P analogs: binding, imaging and receptor activation," BMC Chemical Biology, 2001, 1:1. doi:10.1186/1472-6769-1-1.
Banerjee, S.R. et al. "Synthesis and Evaluation of Technetium-99m- and Rhenium-Labeled Inhibitors of the Prostate-Specific Membrane Antigen (PSMA)," J Med Chem. Aug. 14, 2008; 51(15): 4504-4517.
Chen, Ying, et al., "Radiohalogenated Prostate-Specific Membrane Antigen (PSMA)-Based Ureas as Imaging Agents for Prostate Cancer," J. Med. Chem., 2008, 51 (24), pp. 7933-7943.
Hillier, Shawn M., et al., "Preclinical Evaluation of Novel Glutamate-Urea-Lysine Analogues That Target Prostate-Specific Membrane Antigen as Molecular Imaging Pharmaceuticals for Prostate Cancer," Cancer Res. Sep. 1, 2009;69(17):6932-40.
Maresca, K. P., "A Series of Halogenated Heterodimeric Inhibitors of Prostate Specific Membrane Antigen (PSMA) as Radiolabeled Probes for Targeting Prostate Cancer," J. Med. Chem., 2009, 52 (2), pp. 347-357.
Maresca, K., et al., "Molecular targeting of prostate cancer with small molecule inhibitors of prostate specific membrane antigen (PSMA)," J. Nucl. Med. 2007, 48 (Supplement 2):25P.
Kularatne et al., "Prostate-specific membrane antigen targeted imaging and therapy of prostate cancer using a PSMA inhibitor as a homing ligand," *Molecular Pharmaceutics*, 6(3): 780-789 (2009).
Reddy et al., "PSMA-specific anti-tumor activity of the targeted-tubulysin conjugate, EC1169," *American Association for Cancer Research Annual Meeting* (Apr. 8, 2013) Poster.
Reddy et al., "PSMA-specific anti-tumor activity of the targeted-tubulysin conjugate, EC1169," *American Association for Cancer Research Annual Meeting* (Apr. 8, 2013) Presentation Abstract.
Wang et al., "Prostate-Specific Membrane Antigen Targeted Tubulysin Conjugates for Cancer Therapy," *246th ACS National Meeting and Exposition* (Sep. 8, 2013) Poster.
Cole et al., "Cancer theranostics: the rise of targeted magnetic nanoparticles," Trends in Biotechnology, 2011, 29, 323-332.

(56) References Cited

OTHER PUBLICATIONS

Radioisotopes in Medicine, from http://www.word-nuclear.org/information-library/non-power-nuclear applications/radioisotopes-research/radioisotopes-in-medicine.aspx, Dec. 28, 2016, pp. 1-20.
J.M. Silvola et al., "Al$^{18}$F-NOTA-Folate Accumulates in Atherosclerotic Plaques and Can be Detected by PET/CT", Poster presented Nov. 7, 2015 in Orlando, FL at the 2015 American Heart Association, ReSuscitation Science Symposium (http://newsroom_heart.org/events/scientific-sessions-2015-newsroom- 2942760).
J.M. Silvola et al., "Al$^{18}$F-NOTA-Folate Accumulates in Atherosclerotic Plaques and Can be Detected by PET/CT", Published reference of poster, Nov. 10, 2015, at http://circ.ahajournals.org/content/132/Suppl_3/A18873?cited-by=&legid=circulationaha;132/Suppl_3/A18873; Circulation, 2015, 132:A18873.
PCT Search Report & Written Opinion issued in App. No. PCT/US2014/065467.
Benesova, M. et al., "Linker Modifications of DOTA-conjugated Inhibitors of the Prostate-Specific Association Membrane Antigen (PSMA)," poster, presented at the European Association of Nuclear Medicine Conference on Oct. 21, 2013.
Benesova, M. et al., "Linker Modifications of DOTA-conjugated Inhibitors of the Prostate-Specific Membrane Antigen (PSMA)," abstract, Eur. J. Nucl. Med. Mol. Imaging, available Oct. 16, 2013, 40, Suppl. 2, S193.
Rinnab, L.; et al., "Evaluation of [$^{11}$C]-choline positron-emission/computed tomography in patients with increasing prostate-specific antigen levels after primary treatment for prostate cancer," *BJU Int*, 2007, 100, 786,793.
Reske, S.N.; et al., "Imaging Prostate Cancer with $^{11}$C-Choline PET/CT," J Nucl Med, 2006, 47, 1249-1254.
Zophel, K.; Kotzerke, J, "Is $^{11}$C-choline the most appropriate tracer for prostate cancer?" *Eur J Nucl Med Mol Imaging*, 2004, 31, 756-759.
Vees, H.; et al., "$^{18}$F-choline and/or $^{11}$C-acetate positron emission tomography: detection of residual or progressive subclinical disease at very low prostate-specific antigen values (<1 ng/mL) after radical prostatectomy," *BJU Int*, 2007, 99, 1415-1420.
Larson, S. M.; et al., "Tumor Localization of 16β-$^{18}$F-Fluoro-5α-Dihydrotestosterone Versus $^{18}$F -FDG in Patients with Progressive, Metastatic Prostate Cancer," *J Nucl Med*, 2004, 45, 366-373.
Schuster, D.M.; et al., "Initial Experience with the Radiotracer Anti-1-Amino-3-$^{18}$F-Fluorocyclobutane-1-Carboxylic Acid with PET/CT in Prostate Carcinoma," *J Nucl Med*, 2007, 48, 56-63.
Tehrani, O.S.; et al., "Tumor Imaging Using 1-(2'-deoxy-2'-$^{18}$F-Fluoro-β-D-Arabinofuranosyl)Thymine and PET," *J Nuc/ Med*, 2007, 48, 1436-1441.
Mease RC. et al., "N-[N-[(S)-1,3-Dicarboxypropyl]Carbamoyl]-4-[$^{18}$F]Fluorobenzyl-LCysteine, [$^{18}$F]DCFBC: A New Imaging Probe for Prostate Cancer," Clin Cancer Res., 2008, 14, 3036-3043.
Zhou, J.; et al., "NAAG Peptidase Inhibitors and Their Potential for Diagnosis and Therapy," *Nat Rev Drug Discovery*, 2005, 4, 1015-1026.
Schulke, N.; et al., "The homodimer of prostate-specific membrane antigen is a functional target for cancer therapy," Proc Natl Acad Sci U S A, 2003, 100, 12590-12595.
Nan, F.; et al., "Dual Function Glutamate-Related Ligands: Discovery of a Novel, Potent Inhibitor of Glutamate Carboxypeptidase II Possessing mGluR3 Agonist Activity," J Med Chem, 2000, 43, 772-774.
Lange, P.H., "ProstaScint scan for staging prostate cancer," *Urology*, 2001, 57, 402-406.
Haseman, M.K.; et al., "Capromab Pendetide Imaging of Prostate Cancer," Cancer Biother Radiopharm, 2000, 15, 131-140.
Mier W., et al., "Conjugation of DOTA Using Isolated Phenolic Active Esters: the Labeling and Biodistribution of Albumin as Blood Pool Marker," *Bioconjugate Chem.*, 2005, 16: 237-240.
Schafer et al., "A dimerized urea-based inhibitor of the prostate-specific membrane antigen for $^{68}$Ga-PET imaging of prostate cancer," EJNMMI Research, 2012, 2, 23, 11 pages.
Humblet, V. et al., "An HPLC/mass spectrometry platform for the development of multimodality contrast agents and targeted therapeutics: prostate-specific membrane antigen small molecule derivatives," Contrast Med. Mol. Imaging, 2006, 1, 196-211.
Pomper, M.G.; et al., "$^{11}$C-MCG: synthesis, uptake selectivity, and primate PET of a probe for glutamate carboxypeptidase II (NAALADase)," Mol Imaging, 2002, 1, 96-101.
Scher, B.; et al., "Value of 11C-choline PET and PET/CT in patients with suspected prostate cancer," Eur. J. Nucl. Med. Mol. Imaging., 2007, 34, 45-53.
Tasch, J.; et al., "A Unique Folate Hydrolase, Prostage-Specific Membrane Antingen (PSMA): A Target for Immunotherapy?" Crit. Rev. Immunol., 2001, 21, 249-261.
Rosenthal, S.A.; et al., "Utility of Capromab Pendetide (ProstaScint) Imaging in the Management of Prostate Cancer," Tech Urol, 2001, 7, 27-37.
Wiberg et al. A comparison of some properties of C═O and C═S bonds. ARKIVOC, 2011, pp. 45-56 (2011).
European Patent Application No. EP 14861854, by Endocyte, Inc. et al.: Partial Supplementary Search Report with Opinion; dated May 19, 2017 (15 pages).
European search report in EP 18175078, completed Sep. 6, 2018.

* cited by examiner

PSMA BINDING LIGAND-LINKER CONJUGATES AND METHODS FOR USING

CROSS-REFERENCE TO RELATED APPLICATIONS

This application is a continuation of U.S. application Ser. No. 15/018,068, filed Feb. 8, 2016, which is a continuation-in part of U.S. application Ser. No. 13/580,436, filed Aug. 22, 2012, which is a U.S. national application under 35 U.S.C. § 371(b) of International Application Serial No. PCT/US2011/026238 filed Feb. 25, 2011, and claims priority under 35 USC § 119(e) to U.S. Provisional Application Ser. No. 61/308,190, filed on Feb. 25, 2010, the entire disclosures of each of which are incorporated herein by reference.

STATEMENT REGARDING PRIOR DISCLOSURES BY THE INVENTOR OR A JOINT INVENTOR

International Publication Number WO2009/026177, published on Feb. 26, 2009, was made by the inventor or joint inventor.

TECHNICAL FIELD

The invention described herein pertains to compounds and methods for treating diseases of the prostate, such as prostate cancer and related diseases. More specifically, embodiments of the invention described herein pertain to conjugates of biologically active agents conjugated to PSMA binding ligands.

BACKGROUND AND SUMMARY OF THE INVENTION

The prostate is one of the male reproductive organs found in the pelvis below the urinary bladder. It functions to produce and store seminal fluid which provides nutrients and fluids that are vital for the survival of sperm introduced into the vagina during reproduction. Like many other tissues, the prostate glands are also prone to develop either malignant (cancerous) or benign (non-cancerous) tumors. The American Cancer Society predicted that over 230,000 men would be diagnosed with prostrate cancer and over 30,000 men would die from the disease in year 2005. In fact, prostate cancer is one of the most common male cancers in western societies, and is the second leading form of malignancy among American men. Current treatment methods for prostrate cancer include hormonal therapy, radiation therapy, surgery, chemotherapy, photodynamic therapy, and combination therapy. The selection of a treatment generally varies depending on the stage of the cancer. However, many of these treatments affect the quality of life of the patient, especially those men who are diagnosed with prostrate cancer over age 50. For example, the use of hormonal drugs is often accompanied by side effects such as osteoporosis and liver damage. Such side effects might be mitigated by the use of treatments that are more selective or specific to the tissue being responsible for the disease state, and avoid non-target tissues like the bones or the liver. As described herein, prostate specific membrane antigen (PSMA) represents a target for such selective or specific treatments.

PSMA is named largely due to its higher level of expression on prostate cancer cells; however, its particular function on prostate cancer cells remains unresolved. PSMA is over-expressed in the malignant prostate tissues when compared to other organs in the human body such as kidney, proximal small intestine, and salivary glands. Though PSMA is expressed in brain, that expression is minimal, and most ligands of PSMA are polar and are not capable of penetrating the blood brain barrier. PSMA is a type II cell surface membrane-bound glycoprotein with ~110 kD molecular weight, including an intracellular segment (amino acids 1-18), a transmembrane domain (amino acids 19-43), and an extensive extracellular domain (amino acids 44-750). While the functions of the intracellular segment and the transmembrane domains are currently believed to be insignificant, the extracellular domain is involved in several distinct activities. PSMA plays a role in central nervous system, where it metabolizes N-acetyl-aspartyl glutamate (NAAG) into glutamic and N-acetyl aspartic acid. Accordingly, it is also sometimes referred to as an N-acetyl alpha linked acidic dipeptidase (NAALADase). PSMA is also sometimes referred to as a folate hydrolase I (FOLH I) or glutamate carboxypeptidase (GCP II) due to its role in the proximal small intestine where it removes γ-linked glutamate from poly-γ-glutamated folate and α-linked glutamate from peptides and small molecules.

PSMA also shares similarities with human transferrin receptor (TfR), because both PSMA and TfR are type II glycoproteins. More specifically, PSMA shows 54% and 60% homology to TfR1 and TfR2, respectively. However, though TfR exists only in dimeric form due to the formation of inter-strand sulfhydryl linkages, PSMA can exist in either dimeric or monomeric form.

Unlike many other membrane-bound proteins, PSMA undergoes rapid internalization into the cell in a similar fashion to cell surface bound receptors like vitamin receptors. PSMA is internalized through clathrin-coated pits and subsequently can either recycle to the cell surface or go to lysosomes. It has been suggested that the dimer and monomer form of PSMA are inter-convertible, though direct evidence of the interconversion is being debated. Even so, only the dimer of PSMA possesses enzymatic activity, and the monomer does not.

Though the activity of the PSMA on the cell surface of the prostate cells remains under investigation, it has been recognized by the inventors herein that PSMA represents a viable target for the selective and/or specific delivery of biologically active agents, including diagnostic agents, imaging agents, and therapeutic agents to such prostate cells.

It has been discovered that biologically active compounds that are conjugated to ligands capable of binding to prostate specific membrane antigen (PSMA) via a linker may be useful in the imaging, diagnosis, and/or treatment of prostate cancer, and related diseases that involve pathogenic cell populations expressing or over-expressing PSMA. PSMA is a cell surface protein that is internalized in a process analogous to endocytosis observed with cell surface receptors, such as vitamin receptors. Accordingly, it has been discovered that certain conjugates that include a linker having a predetermined length, and/or a predetermined diameter, and/or preselected functional groups along its length may be used to treat, image, and/or diagnose such diseases.

In one illustrative embodiment of the invention, conjugates having the formula

B-L-D are described wherein B is a prostate specific membrane antigen (PSMA) binding or targeting ligand, L is a linker, and D is a drug. As used herein, the term drug D collectively includes therapeutic agents, cytotoxic agents, imaging agents, diagnostic agents, and the like, unless otherwise indicated or by the context. For example, in one illustrative configuration, the conjugate described herein is used to eliminate a pathogenic population of cells and therefore the drug D is a therapeutic agent, a cytotoxic agent, and the like. In another illustrative configuration, the conjugate described herein is used to image and/or diagnose a disease or disease state, and therefore the drug D is an imaging agent, a diagnostic agent, and the like. Other configurations are also contemplated and described herein. It is to be understood that analogs and derivatives of each of the foregoing B, L, and D are also contemplated and described herein, and that when used herein, the terms B, L, and D collectively refer to such analogs and derivatives.

In one illustrative embodiment, the linker L may be a releasable or non-releasable linker. In one aspect, the linker L is at least about 7 atoms in length. In one variation, the linker L is at least about 10 atoms in length. In one variation, the linker L is at least about 14 atoms in length. In another variation, the linker L is between about 7 and about 31, between about 7 and about 24, or between about 7 and about 20 atoms in length. In another variation, the linker L is between about 14 and about 31, between about 14 and about 24, or between about 14 and about 20 atoms in length.

In an alternative aspect, the linker L is at least about 10 angstroms (Å) in length. In one variation, the linker L is at least about 15 Å in length. In another variation, the linker L is at least about 20 Å in length. In another variation, the linker L is in the range from about 10 Å to about 30 Å in length.

In an alternative aspect, at least a portion of the length of the linker L is about 5 Å in diameter or less at the end connected to the binding ligand B. In one variation, at least a portion of the length of the linker L is about 4 Å or less, or about 3 Å or less in diameter at the end connected to the binding ligand B. It is appreciated that the illustrative embodiments that include a diameter requirement of about 5 Å or less, about 4 Å or less, or about 3 Å or less may include that requirement for a predetermined length of the linker, thereby defining a cylindrical-like portion of the linker. Illustratively, in another variation, the linker includes a cylindrical portion at the end connected to the binding ligand that is at least about 7 Å in length and about 5 Å or less, about 4 Å or less, or about 3 Å or less in diameter.

In another embodiment, the linker L includes one or more hydrophilic linkers capable of interacting with one or more residues of PSMA, including amino acids that have hydrophilic side chains, such as Ser, Thr, Cys, Arg, Orn, Lys, Asp, Glu, Gln, and like residues. In another embodiment, the linker L includes one or more hydrophobic linkers capable of interacting with one or more residues of PSMA, including amino acids that have hydrophobic side chains, such as Val, Leu, Ile, Phe, Tyr, Met, and like residues. It is to be understood that the foregoing embodiments and aspects may be included in the linker L either alone or in combination with each other. For example, linkers L that are at least about 7 atoms in length and about 5 Å, about 4 Å or less, or about 3 Å or less in diameter or less are contemplated and described herein, and also include one or more hydrophilic linkers capable of interacting with one or more residues of PSMA, including Val, Leu, Ile, Phe, Tyr, Met, and like residues are contemplated and described herein.

In another embodiment, one end of the linker is not branched and comprises a chain of carbon, oxygen, nitrogen, and sulfur atoms. In one embodiment, the linear chain of carbon, oxygen, nitrogen, and sulfur atoms is at least 5 atoms in length. In one variation, the linear chain is at least 7 atoms, or at least 10 atoms in length. In another embodiment, the chain of carbon, oxygen, nitrogen, and sulfur atoms are not substituted. In one variation, a portion of the chain of carbon, oxygen, nitrogen, and sulfur atoms is cyclized with a divalent fragment. For example, a linker (L) comprising the dipeptide Phe-Phe may include a piperazin-1,4-diyl structure by cyclizing two nitrogens with an ethylene fragment, or substituted variation thereof.

In another embodiment, pharmaceutical compositions are described herein, where the pharmaceutical composition includes the conjugates described herein in amounts effective to treat diseases and disease states, diagnose diseases or disease states, and/or image tissues and/or cells that are associated with pathogenic populations of cells expressing or over expressing PSMA. Illustratively, the pharmaceutical compositions also include one or more carriers, diluents, and/or excipients.

In another embodiment, methods for treating diseases and disease states, diagnosing diseases or disease states, and/or imaging tissues and/or cells that are associated with pathogenic populations of cells expressing or over expressing PSMA are described herein. Such methods include the step of administering the conjugates described herein, and/or pharmaceutical compositions containing the conjugates described herein, in amounts effective to treat diseases and disease states, diagnose diseases or disease states, and/or image tissues and/or cells that are associated with pathogenic populations of cells expressing or over expressing PSMA.

DETAILED DESCRIPTION

Drug delivery conjugates are described herein where a PSMA binding ligand is attached to a releasable or non-releasable linker which is attached to a drug, therapeutic agent, diagnostic agent, or imaging agent.

Illustratively, the bivalent linkers described herein may be included in linkers used to prepare PSMA-binding drug conjugates, PSMA-binding imaging agent conjugates, and PSMA-binding diagnostic agent conjugates of the following formulae:

B-L-TA

B-L-IA

B-L-DA where B is a PSMA-binding moiety, including analogs or derivatives thereof, L is a linker, TA is a therapeutic agent or cytotoxic agent, including analogs or derivatives thereof, IA is an imaging agent, including analogs or derivatives thereof, and DA is a diagnostic agent, including analogs or derivatives thereof. The linker L can comprise multiple bivalent linkers, including the bivalent linkers described herein. It is also to be understood that as used herein, TA collectively refers to therapeutic agents, and analogs and derivatives thereof, IA collectively refers to imaging agents, and analogs and derivatives thereof, and DA collectively refers to diagnostic agents, and analogs and derivatives thereof.

The linker may also include one or more spacer linkers and optionally additional releasable linkers. The spacer and releasable linkers may be attached to each other in any order or combination. Similarly, the PSMA binding ligand may be attached to a spacer linker or to a releasable linker. Similarly, the drug, therapeutic agent, diagnostic agent, or imaging agent may be attached to a spacer linker or to a releasable linker. Each of these components of the conjugates may be connected through existing or additional heteroatoms on the targeting ligand, drug, therapeutic agent, diagnostic agent, imaging agent, releasable or spacer linker. Illustrative heteroatoms include nitrogen, oxygen, sulfur, and the formulae —(NHR$^1$NHR$^2$)—, —SO—, —(SO$_2$)—, and —N(R$^3$)O—, wherein R$^1$, R$^2$, and R$^3$ are each independently selected from hydrogen, alkyl, heteroalkyl, heterocyclyl, aryl, heteroaryl, arylalkyl, heteroarylalkyl, and the like, each of which may be optionally substituted.

In one illustrative embodiment, compounds are described herein that include linkers having predetermined length and diameter dimensions. In one aspect, linkers are described herein that satisfy one or more minimum length requirements, or a length requirement falling within a predetermined range. In another aspect, satisfaction of a minimum length requirement may be understood to be determined by computer modeling of the extended conformations of linkers. In another aspect, satisfaction of a minimum length requirement may be understood to be determined by having a certain number of atoms, whether or not substituted, forming a backbone chain of atoms connecting the binding ligand (B) with the drug (D). In another embodiment, the backbone chain of atoms is cyclized with another divalent fragment. In another aspect, linkers are described herein that satisfy one or more maximum or minimum diameter requirements. In another aspect, satisfaction of a maximum or minimum diameter requirement may be understood to be determined by computer modeling of various conformations of linkers modeled as the space-filling, CPK, or like configurations. In another aspect, satisfaction of a maximum or minimum diameter requirement may be understood to be apply to one or more selected portions of the linker, for example the portion of the linker proximal to the binding ligand (B), or the portion of the linker proximal to the drug (D), and the like. In another aspect, linkers are described herein that satisfy one or more chemical composition requirements, such as linkers that include one or more polar groups that may positively interact with the one or more Arg or Lys side-chain nitrogens and/or Asp or Glu side chain oxygens found in the funnel portion of PSMA. In one variation, linkers are described herein that satisfy one or more chemical composition requirements, such as linkers that include one or more non-polar groups that may positively interact with the one or more Tyr or Phe side-chain carbons found in the funnel portion of PSMA.

In one embodiment, the atom-length of the linker is defined by the number of atoms separating the binding or targeting ligand B, or analog or derivative thereof, and the drug D, or analog or derivative thereof. Accordingly, in configurations where the binding ligand B, or analog or derivative thereof, is attached directly to the drug D, or analog or derivative thereof, the attachment is also termed herein as a "0-atom" linker. It is understood that such 0-atom linkers include the configuration wherein B and D are directly attached by removing a hydrogen atom from each attachment point on B and D, respectively. It is also understood that such 0-atom linkers include the configuration wherein B and D are attached through an overlapping heteroatom by removing a hydrogen atom from one of B or D, and a heteroatom functional group, such as OH, SH, NH$_2$, and the like from the other of B or D. It is also understood that such 0-atom linkers include the configuration wherein B and D are attached through a double bond, which may be formed by removing two hydrogen atoms from each attachment point on B and D, respectively, or whereby B and D are attached through one or more overlapping heteroatoms by removing two hydrogen atoms, one hydrogen and one heteroatom functional group, or two heteroatom functional groups, such as OH, SH, NH$_2$, and the like, from each of B or D. In addition, B and D may be attached through a double bond formed by removing a double bonded heteroatom functional group, such as O, S, NH, and the like, from one or both of B or D. It is also to be understood that such heteroatom functional groups include those attached to saturated carbon atoms, unsaturated carbon atoms (including carbonyl groups), and other heteroatoms. Similarly, the length of linkers that are greater than 0 atoms are defined in an analogous manner.

Accordingly, in another illustrative embodiment, linkers (L) are described having a chain length of at least 7 atoms. In one variation, linkers (L) are described having a chain length of at least 14 atoms. In another variation, linkers (L) are described having a chain length in the range from about 7 atoms to about 20 atoms. In another variation, linkers (L) are described having a chain length in the range from about 14 atoms to about 24 atoms.

In another embodiment, the length of the linker (L) is defined by measuring the length of an extended conformation of the linker. Such extended conformations may be measured in art-recognized computer modeling programs, such as PC Model 7 (MMX). Accordingly, in another illustrative embodiment, linkers are described having a chain length of at least 15 Å, at least 20 Å, or at least 25 Å.

In another embodiment, linkers are described having at least one hydrophobic side chain group, such as an alkyl, cycloalkyl, aryl, arylalkyl, or like group, each of which is optionally substituted. In one aspect, the hydrophobic group is included in the linker by incorporating one or more Phe or Tyr groups, including substituted variants thereof, and analogs and derivatives thereof, in the linker chain. It is appreciated that such Phe and/or Tyr side chain groups may form positive pi-pi (π-π) interactions with Tyr and Phe residues found in the funnel of PSMA. In addition, it is appreciated that the presence of large side chain branches, such as the arylalkyl groups found on Phe and Tyr may provide a level of conformational rigidity to the linker, thus limiting the degrees of freedom, and reducing coiling and promoting extended conformations of the linker. Without being bound by theory, it is appreciated that such entropy restrictions may increase the overall binding energy of the bound conjugates described herein. In addition, it is appreciated that the rigidity increases that may be provided by sterically hindered side chains, such as Phe and Tyr described herein, may reduce or prevent coiling and interactions between the ligand and the imaging agent.

It has been discovered herein that the funnel shaped tunnel leading to the catalytic site or active site of PSMA imposes length, shape, and/or chemical composition requirements on the linker portion of conjugates of PSMA binding ligands and therapeutic, diagnostic, and imaging agents that positively and negatively affect the interactions between PSMA and those conjugates. Described herein are illustrative embodiments of those conjugates that include such length, shape, and/or chemical composition requirements on the linker. Such length, shape, and/or chemical composition requirements were assessed using molecular modeling. For example, the space filling and surface model of the PSMA complex with (S)-2-(4-iodobenzensylphosphonomethyl)-pentanedioic [2-PMPA derivative] PDB ID code 2C6P were generated using PROTEIN EXPLORER. The PROTEIN EXPLORER model verified the 20 Å deep funnel, and also showed diameter features at various locations along the funnel that may be used to define linkers having favorable structural features. In addition, the model showed that close to the active site of PSMA, there are a higher number of hydrophobic residues that may provide additional binding interactions when the corresponding functional groups are included in the linker. Finally, the model showed the presence of three hydrophobic pockets that may provide additional binding interactions when the corresponding functional groups are included in the linker.

In another illustrative embodiment, following molecular models are created for the conjugates described herein. The models are created using PC Model 7 (MMX) with energy minimization, and using the following bond length parameters: C—C(sp$^3$-sp$^3$)=1.53 Å, C—C (sp$^3$-sp$^2$)=1.51 Å, C—N(sp$^3$-N)=1.47 Å, C—N(sp$^2$-N)=1.38 Å. Such models may be used to calculate the length of the linker connecting the binding ligand (B) and the drug (D). In addition, such models may be modified to create extended conformations, and subsequently used to calculate the length of the linker connecting the binding ligand (B) and the drug (D).

The first human PSMA gene was cloned from LNCaP cells and is reported to be located in chromosome 11p11-12. In addition, there is a PSMA-like gene located at the loci 11q14.3. The crystal structure of PSMA has been reported by two different groups at different resolutions, and each shows that the active site contains two zinc atoms, confirming that PSMA is also considered a zinc metalloprotease. Davis et al, PNAS, 102:5981-86, (2005) reported the crystal structure at low resolution (3.5 Å), while Mesters et al, The EMBO Journal, 1-10 (2006) reported the crystal structure at higher resolution (2-2.2 Å), the disclosures of which are incorporated herein by reference. The crystal structures show that PSMA is a homodimer that contains a protease domain, an apical domain, a helical domain and a CPG2 dimerization domain. The protease domain of PSMA contains a binuclear zinc site, catalytic residues and a substrate binding region including three arginine residues (also referred to as a substrate binding arginine patch). In the crystal structure, the two zinc ions in the active site are each ligated to an oxygen of phosphate, or to the phosphinate moiety of the inhibitor GPI 18431 for the co-crystal structure. In the high resolution crystal structures of the extracellular domain, PSMA was co-crystallized with both potent inhibitors, weak inhibitors, and glutamate at 2.0, 2.4, and 2.2 Å, respectively. The high resolution crystal structure shows a 20 Å deep funnel shaped tunnel leads to the catalytic site or active site of PSMA. The funnel is lined with the side chains of a number of Arg and Lys residues, Asp and Glu residues, and Tyr and Phe residues.

In another embodiment, the linker (L) is a chain of atoms selected from C, N, O, S, Si, and P. The linker may have a wide variety of lengths, such as in the range from about 7 to about 100. The atoms used in forming the linker may be combined in all chemically relevant ways, such as chains of carbon atoms forming alkylene groups, chains of carbon and oxygen atoms forming polyoxyalkylene groups, chains of carbon and nitrogen atoms forming polyamines, and others. In addition, it is to be understood that the bonds connecting atoms in the chain may be either saturated or unsaturated, such that for example, alkanes, alkenes, alkynes, cycloalkanes, arylenes, imides, and the like may be divalent radicals that are included in the linker. In addition, it is to be understood that the atoms forming the linker may also be cyclized upon each other to form divalent cyclic radicals in the linker. In each of the foregoing and other linkers described herein the chain forming the linker may be substituted with a wide variety of groups.

In another embodiment, linkers (L) are described that include at least one releasable linker. In one variation, linkers (L) are described that include at least two releasable linkers. In another variation, linkers (L) are described that include at least one self-immolative linker. In another variation, linkers (L) are described that include at least one releasable linker that is not a disulfide. In another embodiment, linkers (L) are described that do not include a releasable linker.

It is appreciated that releasable linkers may be used when the drug to be delivered is advantageously liberated from the binding ligand-linker conjugate so that the free drug will have the same or nearly the same effect at the target as it would when administered without the targeting provided by the conjugates described herein. In another embodiment, the linker L is a non-releasable linker. It is appreciated that non-releasable linkers may be used when the drug is advantageously retained by the binding ligand-linker conjugate, such as in imaging, diagnosing, uses of the conjugates described herein. It is to be understood that the choice of a releasable linker or a non-releasable linker may be made independently for each application or configuration of the conjugates, without limiting the invention described herein. It is to be further understood that the linkers L described herein comprise various atoms, chains of atoms, functional groups, and combinations of functional groups. Where appropriate in the present disclosure, the linker L may be referred to by the presence of spacer linkers, releasable linkers, and heteroatoms. However, such references are not to be construed as limiting the definition of the linkers L described herein.

The linker (L) comprising spacer and/or releasable linkers (i.e., cleavable linkers) can be any biocompatible linker. The releasable or cleavable linker can be, for example, a linker susceptible to cleavage under the reducing or oxidizing conditions present in or on cells, a pH-sensitive linker that may be an acid-labile or base-labile linker, or a linker that is cleavable by biochemical or metabolic processes, such as an enzyme-labile linker. In one embodiment, the spacer and/or releasable linker comprises about 1 to about 30 atoms, or about 2 to about 20 atoms. Lower molecular weight linkers (i.e., those having an approximate molecular weight of about 30 to about 300) are also described. Precursors to such linkers may be selected to have either nucleophilic or electrophilic functional groups, or both, optionally in a protected form with a readily cleavable protecting group to facilitate their use in synthesis of the intermediate species.

The term "releasable linker" as used herein refers to a linker that includes at least one bond that can be broken under physiological conditions (e.g., a pH-labile, acid-labile, oxidatively-labile, or enzyme-labile bond). The cleavable bond or bonds may be present in the interior of a cleavable linker and/or at one or both ends of a cleavable linker. It should be appreciated that such physiological conditions resulting in bond breaking include standard chemical hydrolysis reactions that occur, for example, at physiological pH, or as a result of compartmentalization into a cellular organelle such as an endosome having a lower pH than cytosolic pH. Illustratively, the bivalent linkers described herein may undergo cleavage under other physiological or metabolic conditions, such as by the action of a glutathione mediated mechanism. It is appreciated that the lability of the cleavable bond may be adjusted by including functional groups or fragments within the bivalent linker L that are able to assist or facilitate such bond breakage, also termed anchimeric assistance. The lability of the cleavable bond can also be adjusted by, for example, substitutional changes at or near the cleavable bond, such as including alpha branching adjacent to a cleavable disulfide bond, increasing the hydrophobicity of substituents on silicon in a moiety having a silicon-oxygen bond that may be hydrolyzed, homologating alkoxy groups that form part of a ketal or acetal that may be hydrolyzed, and the like. In addition, it is appreciated that additional functional groups or fragments may be included within the bivalent linker L that are able to assist or facilitate additional fragmentation of the PSMA binding drug linker conjugates after bond breaking of the releasable linker.

In another embodiment, the linker includes radicals that form one or more spacer linkers and/or releasable linkers that are taken together to form the linkers described herein having certain length, diameter, and/or functional group requirements.

Another illustrative embodiment of the linkers described herein, include releasable linkers that cleave under the conditions described herein by a chemical mechanism involving beta elimination. In one aspect, such releasable linkers include beta-thio, beta-hydroxy, and beta-amino substituted carboxylic acids and derivatives thereof, such as esters, amides, carbonates, carbamates, and ureas. In another aspect, such releasable linkers include 2- and 4-thioarylesters, carbamates, and carbonates.

It is to be understood that releasable linkers may also be referred to by the functional groups they contain, illustratively such as disulfide groups, ketal groups, and the like, as described herein. Accordingly, it is understood that a cleavable bond can connect two adjacent atoms within the releasable linker and/or connect other linkers, or the binding ligand B, or the therapeutic, diagnostic, or imaging agent D, as described herein, at either or both ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as an additional heteroatom, a spacer linker, another releasable linker, the drug D, or analog or derivative thereof, or the binding ligand B, or analog or derivative thereof, following breakage of the bond, the releasable linker is separated from the other moiety.

In another embodiment, the releasable and spacer linkers may be arranged in such a way that subsequent to the cleavage of a bond in the bivalent linker, released functional groups anchimerically assist the breakage or cleavage of additional bonds, as described above. An illustrative embodiment of such a bivalent linker or portion thereof includes compounds having the formula:

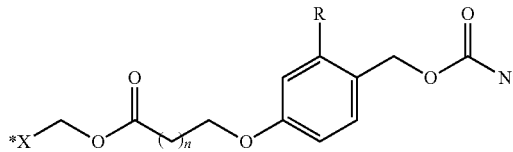

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and the symbol (*) indicates points of attachment for additional spacer or releasable linkers, or heteroatoms, forming the bivalent linker, or alternatively for attachment of the drug, or analog or derivative thereof, or the PSMA binding ligand, or analog or derivative thereof. It is appreciated that other substituents may be present on the aryl ring, the benzyl carbon, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically assisted mechanism.

In this embodiment, the hydroxyalkanoic acid, which may cyclize, facilitates cleavage of the methylene bridge, by for example an oxonium ion, and facilitates bond cleavage or subsequent fragmentation after bond cleavage of the releasable linker. Alternatively, acid catalyzed oxonium ion-assisted cleavage of the methylene bridge may begin a cascade of fragmentation of this illustrative bivalent linker, or fragment thereof. Alternatively, acid-catalyzed hydrolysis of the carbamate may facilitate the beta elimination of the hydroxyalkanoic acid, which may cyclize, and facilitate cleavage of methylene bridge, by for example an oxonium ion. It is appreciated that other chemical mechanisms of bond breakage or cleavage under the metabolic, physiological, or cellular conditions described herein may initiate such a cascade of fragmentation. It is appreciated that other chemical mechanisms of bond breakage or cleavage under the metabolic, physiological, or cellular conditions described herein may initiate such a cascade of fragmentation.

Illustrative mechanisms for cleavage of the bivalent linkers described herein include the following 1,4 and 1,6 fragmentation mechanisms

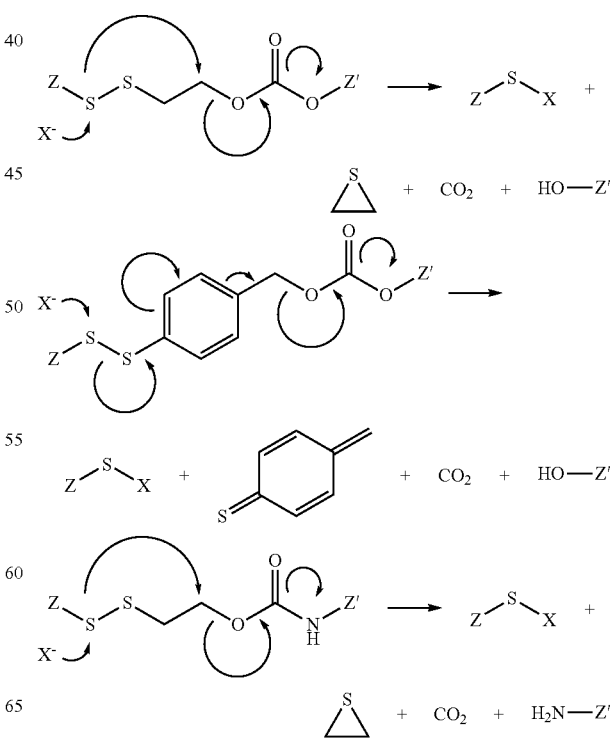

-continued

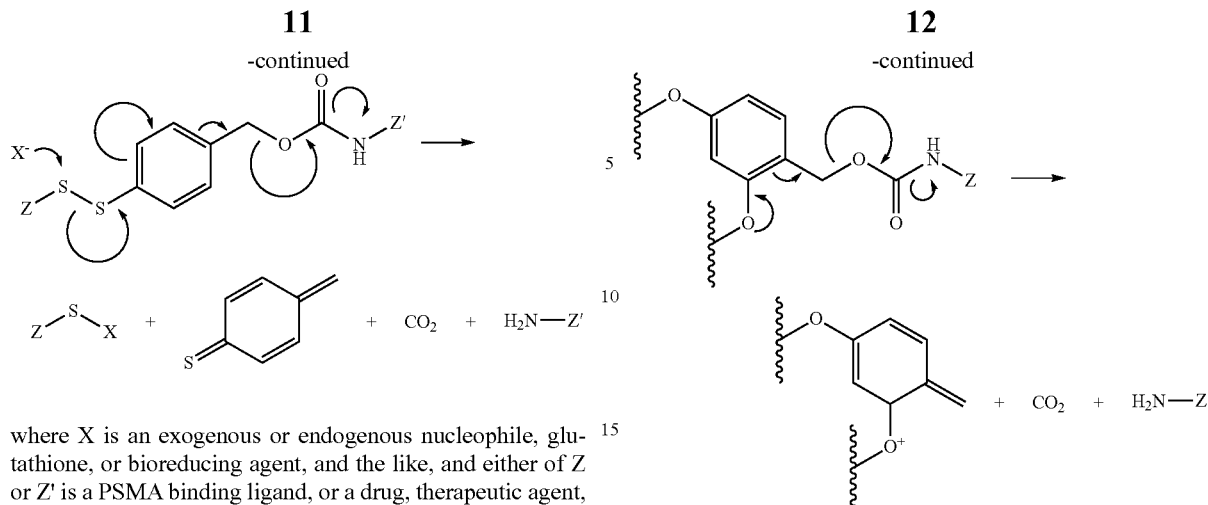

where X is an exogenous or endogenous nucleophile, glutathione, or bioreducing agent, and the like, and either of Z or Z' is a PSMA binding ligand, or a drug, therapeutic agent, diagnostic agent, or imaging agent, or either of Z or Z' is a PSMA binding ligand, or a drug, therapeutic agent, diagnostic agent, or imaging agent connected through other portions of the bivalent linker. It is to be understood that although the above fragmentation mechanisms are depicted as concerted mechanisms, any number of discrete steps may take place to effect the ultimate fragmentation of the bivalent linker to the final products shown. For example, it is appreciated that the bond cleavage may also occur by acid catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In the case of the benzyl-containing bivalent linkers, following an illustrative breaking of the disulfide bond, the resulting phenyl thiolate may further fragment to release a carbonic acid or carbamic acid moiety by forming a resonance stabilized intermediate. In any of these cases, the releaseable nature of the illustrative bivalent linkers described herein may be realized by whatever mechanism may be relevant to the chemical, metabolic, physiological, or biological conditions present.

Other illustrative mechanisms for bond cleavage of the releasable linker include oxonium-assisted cleavage as follows:

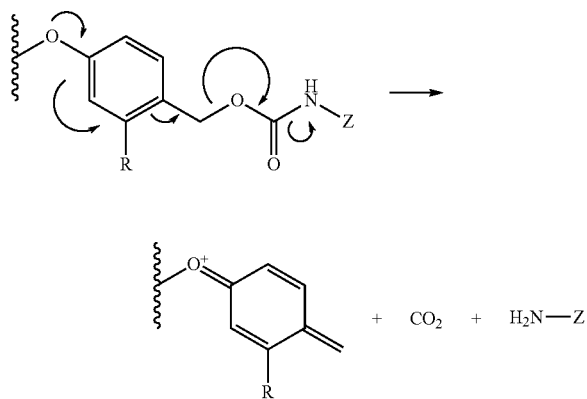

where Z is the PSMA binding ligand, or analog or derivative thereof, or the drug, or analog or derivative thereof, or each is a PSMA binding ligand or drug moiety in conjunction with other portions of the polyvalent linker, such as a drug or PSMA binding ligand moiety including one or more spacer linkers and/or other releasable linkers. In this embodiment, acid-catalyzed elimination of the carbamate leads to the release of $CO_2$ and the nitrogen-containing moiety attached to Z, and the formation of a benzyl cation, which may be trapped by water, or any other Lewis base.

In one embodiment, the releasable linker includes a disulfide.

In another embodiment, the releasable linker may be a divalent radical comprising alkyleneaziridin-1-yl, alkylenecarbonylaziridin-1-yl, carbonylalkylaziridin-1-yl, alkylenesulfoxylaziridin-1-yl, sulfoxylalkylaziridin-1-yl, sulfonylalkylaziridin-1-yl, or alkylenesulfonylaziridin-1-yl, wherein each of the releasable linkers is optionally substituted with a substituent $X^2$, as defined below.

Additional illustrative releasable linkers include methylene, 1-alkoxyalkylene, 1-alkoxycycloalkylene, 1-alkoxyalkylenecarbonyl, 1-alkoxycycloalkylenecarbonyl, carbonylarylcarbonyl, carbonyl(carboxyaryl)carbonyl, carbonyl(biscarboxyaryl)carbonyl, haloalkylenecarbonyl, alkylene(dialkylsilyl), alkylene(alkylarylsilyl), alkylene(diarylsilyl), (dialkylsilyl)aryl, (alkylarylsilyl)aryl, (diarylsilyl)aryl, oxycarbonyloxy, oxycarbonyloxyalkyl, sulfonyloxy, oxysulfonylalkyl, iminoalkylidenyl, carbonylalkylideniminyl, iminocycloalkylidenyl, carbonylcycloalkylideniminyl, alkylenethio, alkylenearylthio, and carbonylalkylthio, wherein each of the releasable linkers is optionally substituted with a substituent $X^2$, as defined below.

In the preceding embodiment, the releasable linker may include oxygen, and the releasable linkers can be methylene, 1-alkoxyalkylene, 1-alkoxycycloalkylene, 1-alkoxyalkylenecarbonyl, and 1-alkoxycycloalkylenecarbonyl, wherein each of the releasable linkers is optionally substituted with a substituent $X^2$, as defined below, and the releasable linker is bonded to the oxygen to form an acetal or ketal. Alternatively, the releasable linker may include oxygen, and the releasable linker can be methylene, wherein the methylene is substituted with an optionally-substituted aryl, and the releasable linker is bonded to the oxygen to form an acetal or ketal. Further, the releasable linker may include oxygen, and the releasable linker can be sulfonylalkyl, and the releasable linker is bonded to the oxygen to form an alkylsulfonate.

In another embodiment of the above releasable linker embodiment, the releasable linker may include nitrogen, and the releasable linkers can be iminoalkylidenyl, carbonylalkylideniminyl, iminocycloalkylidenyl, and carbonylcycloalkylideniminyl, wherein each of the releasable linkers is optionally substituted with a substituent $X^2$, as defined below, and the releasable linker is bonded to the nitrogen to form an hydrazone. In an alternate configuration, the hydrazone may be acylated with a carboxylic acid derivative, an orthoformate derivative, or a carbamoyl derivative to form various acylhydrazone releasable linkers.

Alternatively, the releasable linker may include oxygen, and the releasable linkers can be alkylene(dialkylsilyl), alkylene(alkylarylsilyl), alkylene(diarylsilyl), (dialkylsilyl)aryl, (alkylarylsilyl)aryl, and (diarylsilyl)aryl, wherein each of the releasable linkers is optionally substituted with a substituent $X^2$, as defined below, and the releasable linker is bonded to the oxygen to form a silanol.

In the above releasable linker embodiment, the drug can include a nitrogen atom, the releasable linker may include nitrogen, and the releasable linkers can be carbonylarylcarbonyl, carbonyl(carboxyaryl)carbonyl, carbonyl(biscarboxyaryl)carbonyl, and the releasable linker can be bonded to the heteroatom nitrogen to form an amide, and also bonded to the drug nitrogen to form an amide.

In the above releasable linker embodiment, the drug can include an oxygen atom, the releasable linker may include nitrogen, and the releasable linkers can be carbonylarylcarbonyl, carbonyl(carboxyaryl)carbonyl, carbonyl(biscarboxyaryl)carbonyl, and the releasable linker can form an amide, and also bonded to the drug oxygen to form an ester.

The substituents $X^2$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the releasable linker can include nitrogen, and the substituent $X^2$ and the releasable linker can form an heterocycle.

The heterocycles can be pyrrolidines, piperidines, oxazolidines, isoxazolidines, thiazolidines, isothiazolidines, pyrrolidinones, piperidinones, oxazolidinones, isoxazolidinones, thiazolidinones, isothiazolidinones, and succinimides.

In one embodiment, the polyvalent linkers described herein are or include compounds of the following formulae:

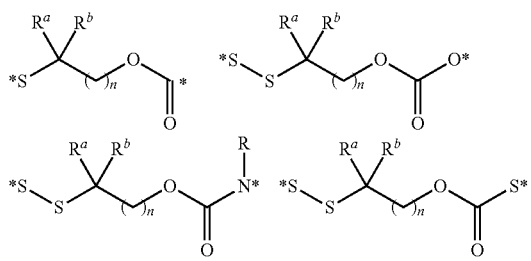

where n is an integer selected from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

In another embodiment, the polyvalent linkers described herein are or include compounds of the following formulae

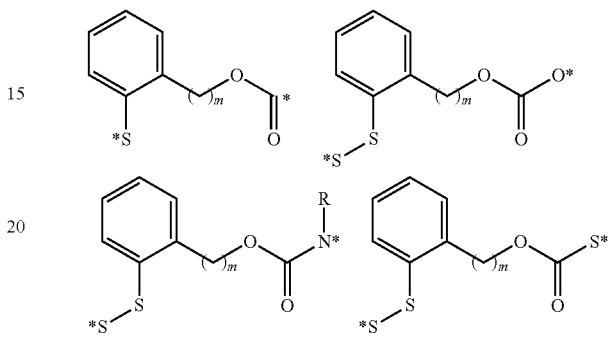

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

In another embodiment, the polyvalent linkers described herein are or include compounds of the following formulae

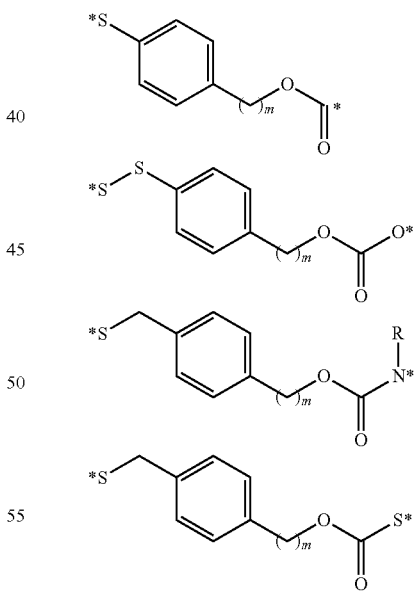

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

In another embodiment, the linker L includes one or more spacer linkers. Such spacer linkers can be 1-alkylenesuccinimid-3-yl, optionally substituted with a substituent X¹, as defined below, and the releasable linkers can be methylene, 1-alkoxyalkylene, 1-alkoxycycloalkylene, 1-alkoxyalkylenecarbonyl, 1-alkoxycycloalkylenecarbonyl, wherein each of the releasable linkers is optionally substituted with a substituent X², as defined above, and wherein the spacer linker and the releasable linker are each bonded to the spacer linker to form a succinimid-1-ylalkyl acetal or ketal.

The spacer linkers can be carbonyl, thionocarbonyl, alkylene, cycloalkylene, alkylenecycloalkyl, alkylenecarbonyl, cycloalkylenecarbonyl, carbonylalkylcarbonyl, 1-alkylenesuccinimid-3-yl, 1-(carbonylalkyl)succinimid-3-yl, alkylenesulfoxyl, sulfonylalkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl)succinimid-3-yl, and 1-(carbonyltetrahydrofuranyl)succinimid-3-yl, wherein each of the spacer linkers is optionally substituted with a substituent X¹, as defined below. In this embodiment, the spacer linker may include an additional nitrogen, and the spacer linkers can be alkylenecarbonyl, cycloalkylenecarbonyl, carbonylalkylcarbonyl, 1-(carbonylalkyl)succinimid-3-yl, wherein each of the spacer linkers is optionally substituted with a substituent X¹, as defined below, and the spacer linker is bonded to the nitrogen to form an amide. Alternatively, the spacer linker may include an additional sulfur, and the spacer linkers can be alkylene and cycloalkylene, wherein each of the spacer linkers is optionally substituted with carboxy, and the spacer linker is bonded to the sulfur to form a thiol. In another embodiment, the spacer linker can include sulfur, and the spacer linkers can be 1-alkylenesuccinimid-3-yl and 1-(carbonylalkyl)succinimid-3-yl, and the spacer linker is bonded to the sulfur to form a succinimid-3-ylthiol.

In an alternative to the above-described embodiments, the spacer linker can include nitrogen, and the releasable linker can be a divalent radical comprising alkyleneaziridin-1-yl, carbonylalkylaziridin-1-yl, sulfoxylalkylaziridin-1-yl, or sulfonylalkylaziridin-1-yl, wherein each of the releasable linkers is optionally substituted with a substituent X², as defined above. In this alternative embodiment, the spacer linkers can be carbonyl, thionocarbonyl, alkylenecarbonyl, cycloalkylenecarbonyl, carbonylalkylcarbonyl, 1-(carbonylalkyl)succinimid-3-yl, wherein each of the spacer linkers is optionally substituted with a substituent X¹, as defined below, and wherein the spacer linker is bonded to the releasable linker to form an aziridine amide.

The substituents X¹ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, R⁴-carbonyl, R⁵-carbonylalkyl, R⁶-acylamino, and R⁷-acylaminoalkyl, wherein R⁴ and R⁵ are each independently selected from amino acids, amino acid derivatives, and peptides, and wherein R⁶ and R⁷ are each independently selected from amino acids, amino acid derivatives, and peptides. In this embodiment the spacer linker can include nitrogen, and the substituent X¹ and the spacer linker to which they are bound to form an heterocycle.

Additional illustrative spacer linkers include alkylene-amino-alkylenecarbonyl, alkylene-thio-(carbonylalkylsuccinimid-3-yl), and the like, as further illustrated by the following formulae:

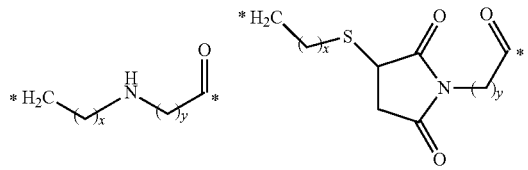

where the integers x and y independently are 1, 2, 3, 4, or 5:

In another embodiment, linkers that include hydrophilic regions are also described. In one aspect, the hydrophilic region of the linker forms part or all of a spacer linker included in the conjugates described herein. Illustrative hydrophilic spacer linkers are described in PCT international application serial No. PCT/US2008/068093, filed Jun. 25, 2008, the disclosure of which is incorporated herein by reference.

The term "cycloalkyl" as used herein includes molecular fragments or radicals comprising a monovalent chain of carbon atoms, a portion of which forms a ring. It is to be understood that the term cycloalkyl as used herein includes fragments and radicals attached at either ring atoms or non-ring atoms, such as, such as cyclopropyl, cyclohexyl, 3-ethylcyclopent-1-yl, cyclopropylethyl, cyclohexylmethyl, and the like.

The term "cycloalkylene" as used herein includes molecular fragments or radicals comprising a bivalent chain of carbon atoms, a portion of which forms a ring. It is to be understood that the term cycloalkylene as used herein includes fragments and radicals attached at either ring atoms or non-ring atoms, such as cycloprop-1,1-diyl, cycloprop-1,2-diyl, cyclohex-1,4-diyl, 3-ethylcyclopent-1,2-diyl, 1-methylenecyclohex-4-yl, and the like.

The terms "heteroalkyl" and "heteroalkylene" as used herein includes molecular fragments or radicals comprising monovalent and divalent, respectively, groups that are formed from a linear or branched chain of carbon atoms and heteroatoms, wherein the heteroatoms are selected from nitrogen, oxygen, and sulfur, such as alkoxyalkyl, alkyleneoxyalkyl, aminoalkyl, alkylaminoalkyl, alkyleneaminoalkyl, alkylthioalkyl, alkylenethioalkyl, alkoxyalkylaminoalkyl, alkylaminoalkoxyalkyl, alkyleneoxyalkylaminoalkyl, and the like.

The term "heterocyclyl" as used herein includes molecular fragments or radicals comprising a monovalent chain of carbon atoms and heteroatoms, wherein the heteroatoms are selected from nitrogen, oxygen, and sulfur, a portion of which, including at least one heteroatom, form a ring, such as aziridine, pyrrolidine, oxazolidine, 3-methoxypyrrolidine, 3-methylpiperazine, and the like. Accordingly, as used herein, heterocyclyl includes alkylheterocyclyl, heteroalkylheterocyclyl, heterocyclylalkyl, heterocyclylheteroalkyl, and the like. It is to be understood that the term heterocyclyl as used herein includes fragments and radicals attached at either ring atoms or non-ring atoms, such as tetrahydrofuran-2-yl, piperidin-1-yl, piperidin-4-yl, piperazin-1-yl, morpholin-1-yl, tetrahydrofuran-2-ylmethyl, piperidin-1-ylethyl, piperidin-4-ylmethyl, piperazin-1-ylpropyl, morpholin-1-ylethyl, and the like.

The term "aryl" as used herein includes molecular fragments or radicals comprising an aromatic mono or polycyclic ring of carbon atoms, such as phenyl, naphthyl, and the like.

The term "heteroaryl" as used herein includes molecular fragments or radicals comprising an aromatic mono or polycyclic ring of carbon atoms and at least one heteroatom selected from nitrogen, oxygen, and sulfur, such as pyridinyl, pyrimidinyl, indolyl, benzoxazolyl, and the like.

The term "substituted aryl" or "substituted heteroaryl" as used herein includes molecular fragments or radicals comprising aryl or heteroaryl substituted with one or more substituents, such as alkyl, heteroalkyl, halo, hydroxy, amino, alkyl or dialkylamino, alkoxy, alkylsulfonyl, aminosulfonyl, carboxylate, alkoxycarbonyl, aminocarbonyl, cyano, nitro, and the like. It is to be understood that the alkyl groups in such substituents may be optionally substituted with halo.

The term "iminoalkylidenyl" as used herein includes molecular fragments or radicals comprising a divalent radical containing alkylene as defined herein and a nitrogen atom, where the terminal carbon of the alkylene is double-bonded to the nitrogen atom, such as the formulae —(CH)═N—, —(CH$_2$)$_2$(CH)═N—, —CH$_2$C(Me)═N—, and the like.

The term "amino acid" as used herein includes molecular fragments or radicals comprising an aminoalkylcarboxylate, where the alkyl radical is optionally substituted with alkyl, hydroxy alkyl, sulfhydrylalkyl, aminoalkyl, carboxyalkyl, and the like, including groups corresponding to the naturally occurring amino acids, such as serine, cysteine, methionine, aspartic acid, glutamic acid, and the like.

For example, in one embodiment, amino acid is a divalent radical having the general formula:

—N(R)—(CR'R'')$_q$—C(O)— where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornitine, threonine, and the like. In one variation, the amino acid may be selected from phenylalanine, tyrosine, and the like, derivatives thereof, and substituted variants thereof.

The terms "arylalkyl" and "heteroarylalkyl" as used herein includes molecular fragments or radicals comprising aryl and heteroaryl, respectively, as defined herein substituted with a linear or branched alkylene group, such as benzyl, phenethyl, α-methylbenzyl, picolinyl, pyrimidinylethyl, and the like.

It is to be understood that the above-described terms can be combined to generate chemically-relevant groups, such as "haloalkoxyalkyl" referring to for example trifluoromethyloxyethyl, 1,2-difluoro-2-chloroeth-1-yloxypropyl, and the like.

The term "amino acid derivative" as used herein refers generally to aminoalkylcarboxylate, where the amino radical or the carboxylate radical are each optionally substituted with alkyl, carboxylalkyl, alkylamino, and the like, or optionally protected; and the intervening divalent alkyl fragment is optionally substituted with alkyl, hydroxy alkyl, sulfhydrylalkyl, aminoalkyl, carboxyalkyl, and the like, including groups corresponding to the side chains found in naturally occurring amino acids, such as are found in serine, cysteine, methionine, aspartic acid, glutamic acid, and the like.

The term "peptide" as used herein includes molecular fragments or radicals comprising a series of amino acids and amino acid analogs and derivatives covalently linked one to the other by amide bonds.

In another embodiment, the bivalent linker comprises a spacer linker and a releasable linker taken together to form 3-thiosuccinimid-1-ylalkyloxymethyloxy, where the methyl is optionally substituted with alkyl or substituted aryl.

In another embodiment, the bivalent linker comprises a spacer linker and a releasable linker taken together to form 3-thiosuccinimid-1-ylalkylcarbonyl, where the carbonyl forms an acylaziridine with the drug, or analog or derivative thereof.

In another embodiment, the bivalent linker comprises a spacer linker and a releasable linker taken together to form 1-alkoxycycloalkylenoxy.

In another embodiment, the bivalent linker comprises a spacer linker and a releasable linker taken together to form alkyleneaminocarbonyl(dicarboxylarylene)carboxylate.

In another embodiment, the bivalent linker comprises a releasable linker, a spacer linker, and a releasable linker taken together to form dithioalkylcarbonylhydrazide, where the hydrazide forms an hydrazone with the drug, or analog or derivative thereof.

In another embodiment, the bivalent linker comprises a spacer linker and a releasable linker taken together to form 3-thiosuccinimid-1-ylalkylcarbonylhydrazide, where the hydrazide forms an hydrazone with the drug, or analog or derivative thereof.

In another embodiment, the bivalent linker comprises a spacer linker and a releasable linker taken together to form 3-thioalkylsulfonylalkyl(disubstituted silyl)oxy, where the disubstituted silyl is substituted with alkyl or optionally substituted aryl.

In another embodiment, the bivalent linker comprises a plurality of spacer linkers selected from the group consisting of the naturally occurring amino acids and stereoisomers thereof.

In another embodiment, the bivalent linker comprises a releasable linker, a spacer linker, and a releasable linker taken together to form 3-dithioalkyloxycarbonyl, where the carbonyl forms a carbonate with the drug, or analog or derivative thereof.

In another embodiment, the bivalent linker comprises a releasable linker, a spacer linker, and a releasable linker taken together to form 2-dithioalkyloxycarbonyl, where the carbonyl forms a carbonate with the drug, or analog or derivative thereof. In another embodiment, alkyl is ethyl.

In another embodiment, the bivalent linker comprises a releasable linker, a spacer linker, and a releasable linker taken together to form 3-dithioarylalkyloxycarbonyl, where the carbonyl forms a carbonate with the drug, or analog or derivative thereof, and the aryl is optionally substituted.

In another embodiment, the bivalent linker comprises a releasable linker, a spacer linker, and a releasable linker taken together to form 2-dithioarylalkyloxycarbonyl or 3-dithioarylalkyloxycarbonyl, where the carbonyl forms a carbonate with the drug, or analog or derivative thereof, and the aryl is optionally substituted.

In another embodiment, the bivalent linker comprises a spacer linker and a releasable linker taken together to form 3-thiosuccinimid-1-ylalkyloxyalkyloxyalkylidene, where the alkylidene forms an hydrazone with the drug, or analog or derivative thereof, each alkyl is independently selected, and the oxyalkyloxy is optionally substituted with alkyl or optionally substituted aryl.

In another embodiment, the bivalent linker comprises a releasable linker, a spacer linker, and a releasable linker taken together to form 3-dithioalkyloxycarbonylhydrazide.

In another embodiment, the bivalent linker comprises a releasable linker, a spacer linker, and a releasable linker taken together to form 2-dithioalkyloxycarbonylhydrazide. In another embodiment, alkyl is ethyl.

In another embodiment, the bivalent linker comprises a releasable linker, a spacer linker, and a releasable linker taken together to form 3-dithioalkylamino, where the amino forms a vinylogous amide with the drug, or analog or derivative thereof.

In another embodiment, the bivalent linker comprises a releasable linker, a spacer linker, and a releasable linker taken together to form 2-dithioalkylamino, where the amino forms a vinylogous amide with the drug, or analog or derivative thereof. In another embodiment, alkyl is ethyl.

In another embodiment, the bivalent linker comprises a releasable linker, a spacer linker, and a releasable linker taken together to form 3-dithioalkylamino, where the amino forms a vinylogous amide with the drug, or analog or derivative thereof. In another embodiment, the bivalent linker comprises a releasable linker, a spacer linker, and a releasable linker taken together to form 2-dithioalkylamino, where the amino forms a vinylogous amide with the drug, or analog or derivative thereof. Illustratively, the alkyl is ethyl.

In another embodiment, the bivalent linker comprises a releasable linker, a spacer linker, and a releasable linker taken together to form 3-dithioalkylaminocarbonyl, where the carbonyl forms a carbamate with the drug, or analog or derivative thereof.

In another embodiment, the bivalent linker comprises a releasable linker, a spacer linker, and a releasable linker taken together to form 2-dithioalkylaminocarbonyl, where the carbonyl forms a carbamate with the drug, or analog or derivative thereof. Illustratively the alkyl is ethyl.

In another embodiment, the bivalent linker comprises a releasable linker, a spacer linker, and a releasable linker taken together to form 3-dithioalkylaminocarbonyl, where the carbonyl forms a carbamate with the drug, or analog or derivative thereof. In another embodiment, the bivalent linker comprises a releasable linker, a spacer linker, and a releasable linker taken together to form 2-dithioalkylaminocarbonyl, where the carbonyl forms a carbamate with the drug, or analog or derivative thereof. Illustratively, the alkyl is ethyl.

In another embodiment, the bivalent linker comprises a releasable linker, a spacer linker, and a releasable linker taken together to form 3-dithioarylalkyloxycarbonyl, where the carbonyl forms a carbamate or a carbamoylaziridine with the drug, or analog or derivative thereof.

In another embodiment, the bivalent linker comprises a releasable linker, a spacer linker, and a releasable linker taken together to form 2-dithioarylalkyloxycarbonyl or 4-dithioarylalkyloxycarbonyl, where the carbonyl forms a carbamate or a carbamoylaziridine with the drug, or analog or derivative thereof.

In another embodiment, the polyvalent linker includes spacer linkers and releasable linkers connected to form a polyvalent 3-thiosuccinimid-1-ylalkyloxymethyloxy group, illustrated by the following formula

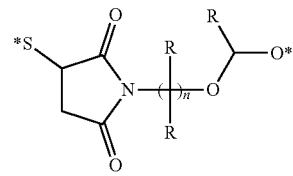

where n is an integer from 1 to 6, the alkyl group is optionally substituted, and the methyl is optionally substituted with an additional alkyl or optionally substituted aryl group, each of which is represented by an independently selected group R. The (*) symbols indicate points of attachment of the polyvalent linker fragment to other parts of the conjugates described herein.

In another embodiment, the polyvalent linker includes spacer linkers and releasable linkers connected to form a polyvalent 3-thiosuccinimid-1-ylalkylcarbonyl group, illustrated by the following formula

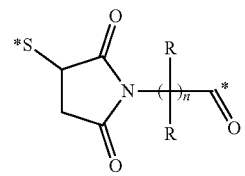

where n is an integer from 1 to 6, and the alkyl group is optionally substituted. The (*) symbols indicate points of attachment of the polyvalent linker fragment to other parts of the conjugates described herein. In another embodiment, the polyvalent linker includes spacer linkers and releasable linkers connected to form a polyvalent 3-thioalkylsulfonylalkyl(disubstituted silyl)oxy group, where the disubstituted silyl is substituted with alkyl and/or optionally substituted aryl groups.

In another embodiment, the polyvalent linker includes spacer linkers and releasable linkers connected to form a polyvalent dithioalkylcarbonylhydrazide group, or a polyvalent 3-thiosuccinimid-1-ylalkylcarbonylhydrazide, illustrated by the following formulae

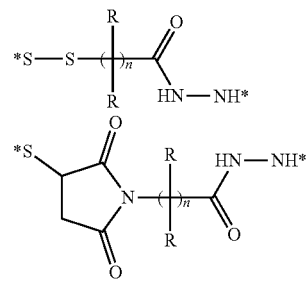

where n is an integer from 1 to 6, the alkyl group is optionally substituted, and the hydrazide forms an hydrazone with (B), (D), or another part of the polyvalent linker (L). The (*) symbols indicate points of attachment of the polyvalent linker fragment to other parts of the conjugates described herein.

In another embodiment, the polyvalent linker includes spacer linkers and releasable linkers connected to form a polyvalent 3-thiosuccinimid-1-ylalkyloxyalkyloxyalkylidene group, illustrated by the following formula

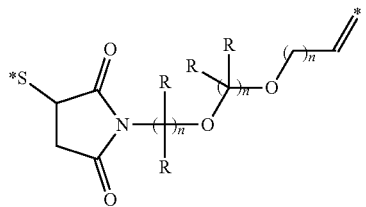

where each n is an independently selected integer from 1 to 6, each alkyl group independently selected and is optionally substituted, such as with alkyl or optionally substituted aryl, and where the alkylidene forms an hydrazone with (B), (D), or another part of the polyvalent linker (L). The (*) symbols indicate points of attachment of the polyvalent linker fragment to other parts of the conjugates described herein.

Additional illustrative linkers are described in WO 2006/012527, the disclosure of which is incorporated herein by reference. Additional linkers are described in the following Table, where the (*) atom is the point of attachment of additional spacer or releasable linkers, the drug, and/or the binding ligand.

Illustrative releasable linkers.

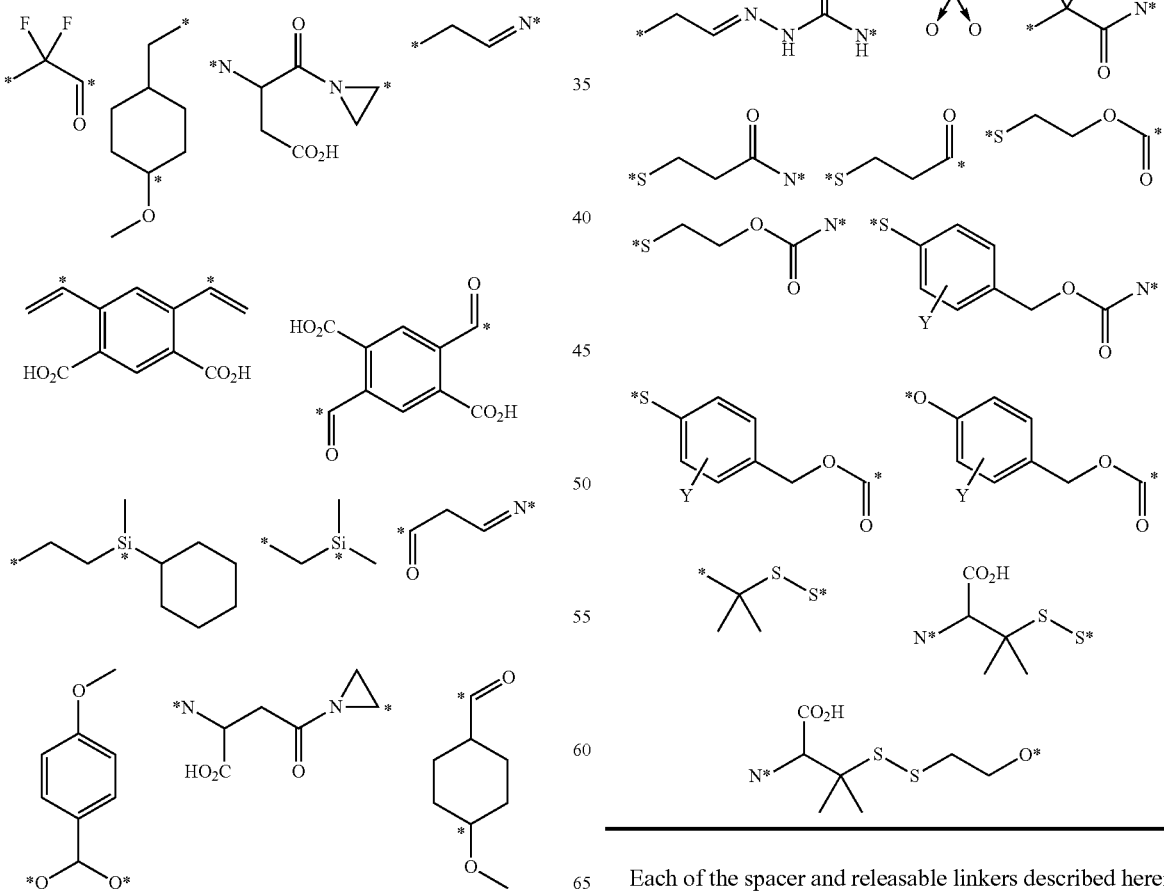

Illustrative releasable linkers.

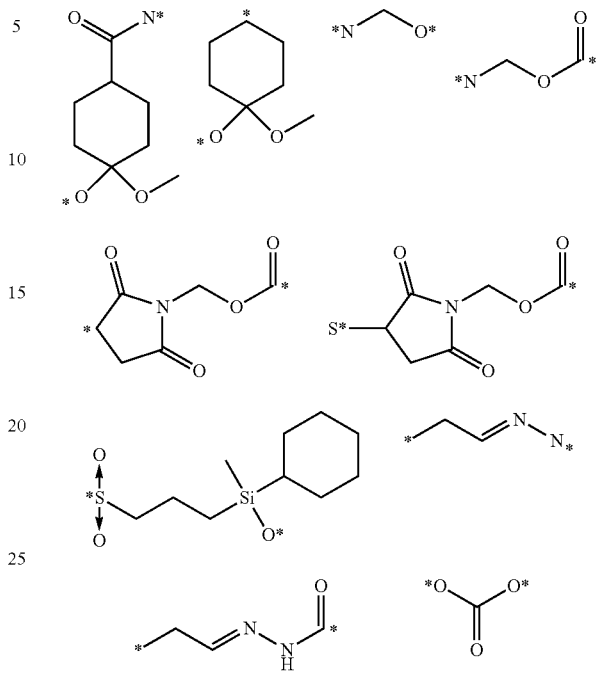

Each of the spacer and releasable linkers described herein is bivalent. In addition, the connections between spacer linkers, releasable linkers, drugs D and ligands B may occur at any atom found in the various spacer linkers, releasable linkers, drugs D, and ligands B.

The drug can include a nitrogen atom, and the releasable linker can be haloalkylenecarbonyl, optionally substituted with a substituent $X^2$, and the releasable linker is bonded to the drug nitrogen to form an amide.

The drug can include an oxygen atom, and the releasable linker can be haloalkylenecarbonyl, optionally substituted with a substituent $X^2$, and the releasable linker is bonded to the drug oxygen to form an ester.

The drug can include a double-bonded nitrogen atom, and in this embodiment, the releasable linkers can be alkylenecarbonylamino and 1-(alkylenecarbonylamino)succinimid-3-yl, and the releasable linker can be bonded to the drug nitrogen to form an hydrazone.

The drug can include a sulfur atom, and in this embodiment, the releasable linkers can be alkylenethio and carbonylalkylthio, and the releasable linker can be bonded to the drug sulfur to form a disulfide.

In another embodiment, the binding or targeting ligand capable of binding or targeting PSMA is a thiophosphoric, thiophosphonic, or thiophosphinic acid or derivative thereof. In one aspect, the thiophosphoric, thiophosphonic, or thiophosphinic acid or derivative thereof includes one or more carboxylic acid groups. In another aspect, the thiophosphoric, thiophosphonic, or thiophosphinic acid or derivative thereof includes one or more thiol groups or derivatives thereof. In another aspect, the thiophosphoric, thiophosphonic, or thiophosphinic acid or derivative thereof includes one or more carboxylic acid bioisosteres, such as an optionally substituted tetrazole, and the like.

In another embodiment, the PSMA ligand is a derivative of pentanedioic acid. Illustratively, the pentanedioic acid derivative is a compound of the formula:

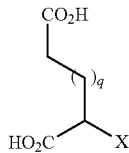

wherein X is RYP(S)(OH)CH$_2$—; RYP(S)(OH)N(R$_1$)—; RP(S)(OH)CH$_2$—; RP(S)(OH)N(R$_1$)—; RP(S)(OH)O—; RYC(S)N(R$_1$)—; RN(OH)C(S)Y; RC(S)NHY; RYP(S)(SH)CH$_2$—; RYP(S)(SH)N(R$_1$)—; RP(S)(SH)CH$_2$—; RP(S)(SH)N(R$_1$)—; RP(S)(SH)S—; RN(SH)C(S)Y— or RC(S)N(OH)Y, and the like; RS(O)Y, RSO$_2$Y, RS(O)(NH)Y, and RS-alkyl, wherein Y is independently selected in each instance from —CR$_1$R$_2$—, —NR$_3$—, —S—, and —O—, wherein R is for example hydrogen, alkyl, aryl, or arylalkyl, each of which may be optionally substituted; and q is 0 to 5.

In another embodiment, the PSMA ligand is a derivative of pentanedioic acid. Illustratively, the pentanedioic acid derivative is a compound of the formula:

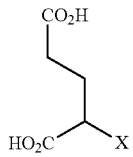

wherein X is RP(S)(OH)CH$_2$—; RP(S)(OH)N(R$_1$)—; RP(S)(OH)O—; RN(OH)C(S)Y; RC(S)NHY; RP(S)(SH)CH$_2$—; RP(S)(SH)N(R$_1$)—; RP(S)(SH)S—; RN(SH)C(S)Y— or RC(S)N(OH)Y, and the like, wherein Y is —CR$_1$R$_2$—, —NR$_3$—, —S—, or —O—; or RS(O)Y, RSO$_2$Y, or RS(O)(NH)Y, wherein Y is —CR$_1$R$_2$—, —NR$_3$— or —O—; or RS-alkyl, wherein R is for example hydrogen, alkyl, aryl, or arylalkyl, each of which may be optionally substituted.

In another embodiment, the PSMA ligand is a derivative of pentanedioic acid. Illustratively, the pentanedioic acid derivative is a compound of the formula:

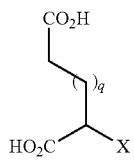

wherein X is RYP(S)(OH)CH$_2$—; RYP(S)(OH)N(R$_1$)—; RP(S)(OH)CH$_2$—; RP(S)(OH)N(R$_1$)—; RYC(S)N(R$_1$)—; RYP(S)(SH)CH$_2$—; RYP(S)(SH)N(R$_1$)—, RP(S)(SH)CH$_2$—; or RP(S)(SH)N(R$_1$)—; wherein Y is independently selected in each instance from —CR$_1$R$_2$—, —NR$_3$—, —S—, and —O—; wherein R is for example hydrogen, alkyl, aryl, or arylalkyl, each of which may be optionally substituted; and q is 0 to 5. In another embodiment, q is 1. In another embodiment, Y is independently selected in each instance from —CR$_1$R$_2$—, and —NR$_3$—.

In each of the foregoing embodiments, R$_1$, R$_2$, and R$_3$ are each independently selected from hydrogen, C$_1$-C$_9$ straight or branched chain alkyl, C$_2$-C$_9$ straight or branched chain alkenyl, C$_3$-C$_8$ cycloalkyl, C$_5$-C$_7$ cycloalkenyl, and aryl. In addition, in each case, each of R, R$_1$, R$_2$, and R$_3$ may be optionally substituted, such as with one or more groups selected from C$_3$-C$_8$ cycloalkyl, C$_5$-C$_7$ cycloalkenyl, halo, hydroxy, nitro, trifluoromethyl, C$_1$-C$_6$ straight or branched chain alkyl, C$_2$-C$_6$ straight or branched chain alkenyl, C$_1$-C$_4$ alkoxy, C$_2$-C$_4$ alkenyloxy, phenoxy, benzyloxy, amino, aryl. In one aspect, aryl is selected from 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl, benzyl, and phenyl, and in each case aryl may be optionally substituted with one or more, illustratively with one to three, groups selected from halo, hydroxy, nitro, trifluoromethyl, C$_1$-C$_6$ straight or branched chain alkyl, C$_2$-C$_6$ straight or branched chain alkenyl, C$_1$-C$_4$ alkoxy, C$_2$-C$_4$ alkenyloxy, phenoxy, benzyloxy, and amino. In one variation of each of the above formulae, R is not hydrogen.

Illustrative PSMA ligands include: 2-[[methylhydroxythiophosphinyl]methyl]pentanedioic acid; 2-[[ethylhydroxythiophosphinyl]methyl]pentanedioic acid; 2-[[propylhydroxythiophosphinyl]methyl]pentanedioic acid; 2-[[butylhydroxythiophosphinyl]methyl]pentanedioic acid; 2-[[cyclohexylhydroxythiophosphinyl]methyl]pentanedioic acid; 2-[[phenylhydroxythiophosphinyl]methyl]pentanedioic acid; 2-[[2-(tetrahydrofuranyl)hydroxythiophosphinyl]methyl]pentanedioic acid; 2-[[(2-tetrahydropyranyl)hydroxythiophosphinyl]methyl] pentanedioic acid; 2-[[((4-pyridyl)methyl)hydroxythiophosphinyl]methyl] pentanedioic acid; 2-[[((2-pyridyl)methyl)hydroxythiophosphinyl]methyl] pentanedioic acid; 2-[[(phenylmethyl)hydroxythiophosphinyl]methyl]pentanedioic acid; 2-[[((2-phenylethyl)methyl)hydroxythiophosphinyl]methyl] pentanedioic acid; 2-[[((3-phenylpropyl)methyl)hydroxythiophosphinyl]methyl]

pentanedioic acid; 2-[[((3-phenylbutyl)methyl)hydroxythiophosphinyl]methyl] pentanedioic acid; 2-[[((2-phenylbutyl)methyl)hydroxythiophosphinyl]methyl] pentanedioic acid; 2-[[(4-phenylbutyl)hydroxythiophosphinyl]methyl] pentanedioic acid; and 2-[[(aminomethyl)hydroxythiophosphinyl]methyl]pentanedioic acid.

Illustrative PSMA ligands include: N-[methylhydroxythiophosphinyl]glutamic acid; N-[ethylhydroxythiophosphinyl]glutamic acid; N-[propylhydroxythiophosphinyl]glutamic acid; N-[butylhydroxythiophosphinyl]glutamic acid; N-[phenylhydroxythiophosphinyl]glutamic acid; N-[(phenylmethyl)hydroxythiophosphinyl]glutamic acid; N-[((2-phenylethyl)methyl)hydroxythiophosphinyl]glutamic acid; and N-methyl-N-[phenylhydroxythiophosphinyl]glutamic acid.

Illustrative PSMA ligands include: 2-[[methylhydroxythiophosphinyl]oxy]pentanedioic acid; 2-[[ethylhydroxythiophosphinyl]oxy]pentanedioic acid; 2-[[propylhydroxythiophosphinyl]oxy]pentanedioic acid; 2-[[butylhydroxythiophosphinyl]oxy]pentanedioic acid; 2-[[phenylhydroxythiophosphinyl]oxy]pentanedioic acid; 2-[[((4-pyridyl)methyl)hydroxythiophosphinyl]oxy]pentanedioic acid; 2-[[((2-pyridyl)methyl)hydroxythiophosphinyl]oxy] pentanedioic acid; 2-[[(phenylmethyl)hydroxythiophosphinyl]oxy]pentanedioic acid; and 2-[[((2-phenylethyl)methyl)hydroxythiophosphinyl]oxy]pentanedioic acid.

Illustrative PSMA ligands include: 2-[[(N-hydroxy)thiocarbamoyl]methyl]pentanedioic acid; 2-[[(N-hydroxy-N-methyl)thiocarbamoyl]methyl]pentanedioic acid; 2-[[(N-butyl-N-hydroxy)thiocarbamoyl]methyl]pentanedioic acid; 2-[[(N-benzyl-N-hydroxy)thiocarbamoyl]methyl]pentanedioic acid; 2-[[(N-hydroxy-N-phenyl)thiocarbamoyl]methyl]pentanedioic acid; 2-[[(N-hydroxy-N-2-phenylethyl)thiocarbamoyl]methyl]pentanedioic acid; 2-[[(N-ethyl-N-hydroxy)thiocarbamoyl]methyl]pentanedioic acid; 2-[[(N-hydroxy-N-propyl)thiocarbamoyl]methyl]pentanedioic acid; 2-[[(N-hydroxy-N-3-phenylpropyl)thiocarbamoyl]methyl]pentanedioic acid; 2-[[(N-hydroxy-N-4-pyridyl)thiocarbamoyl]methyl]pentanedioic acid; 2-[[(N-hydroxy)thiocarboxamido]methyl]pentanedioic acid; 2-[[N-hydroxy(methyl)thiocarboxamido]methyl]pentanedioic acid; 2-[[N-hydroxy(benzyl)thiocarboxamido]methyl]pentanedioic acid; 2-[[N-hydroxy(phenyl)thiocarboxamido]methyl]pentanedioic acid; 2-[[N-hydroxy(2-phenylethyl)thiocarboxamido]methyl]pentanedioic acid; 2-[[N-hydroxy(ethyl)thiocarboxamido]methyl]pentanedioic acid; 2-[[N-hydroxy(propyl)thiocarboxamido]methyl]pentanedioic acid; 2-[[N-hydroxy(3-phenylpropyl)thiocarboxamido]methyl] pentanedioic acid; and 2-[[N-hydroxy(4-pyridyl)thiocarboxamido]methyl]pentanedioic acid.

Pentanedioic acid derivatives described herein, including but not limited to the following thiophosphonic and thiophosphinic acid derivatives.

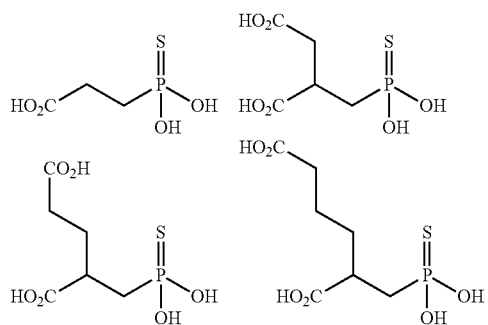

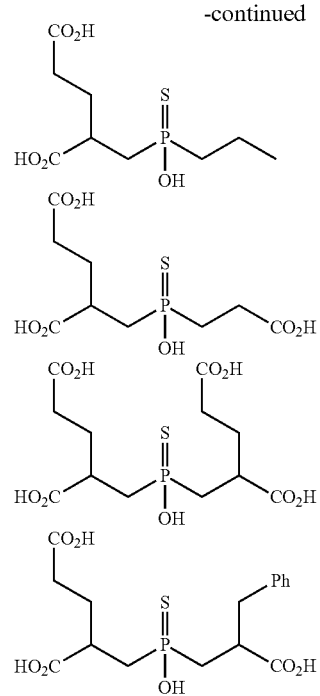

In another embodiment, the PSMA ligand is a thiourea of two amino acids. In one aspect, the amino acids include one or more additional carboxylic acids. In another aspect, the amino acids include one or more additional phosphoric, phosphonic, phosphinic, sulfinic, sulfonic, or boronic acids. In another aspect, the amino acids include one or more thiol groups or derivatives thereof. In another aspect, the amino acids includes one or more carboxylic acid bioisosteres, such as tetrazoles and the like.

In another embodiment, the PSMA ligand is a aminothiocarbonyl derivative of pentanedioic acid. Illustratively, the aminocarbonylpentanedioic acid derivative is a compound of the formula:

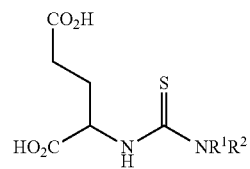

wherein $R^1$ and $R^2$ are each selected from hydrogen, optionally substituted carboxylic acids, such as thiolacetic acids, thiolpropionic acids, and the like; malonic acids, succinic acids, glutamic acids, adipic acids, and the like; and others.

In another embodiment, the PSMA ligand is a compound of the formula:

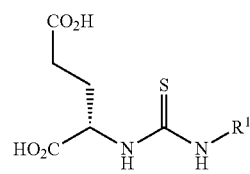

| R¹ | R |
|---|---|
| 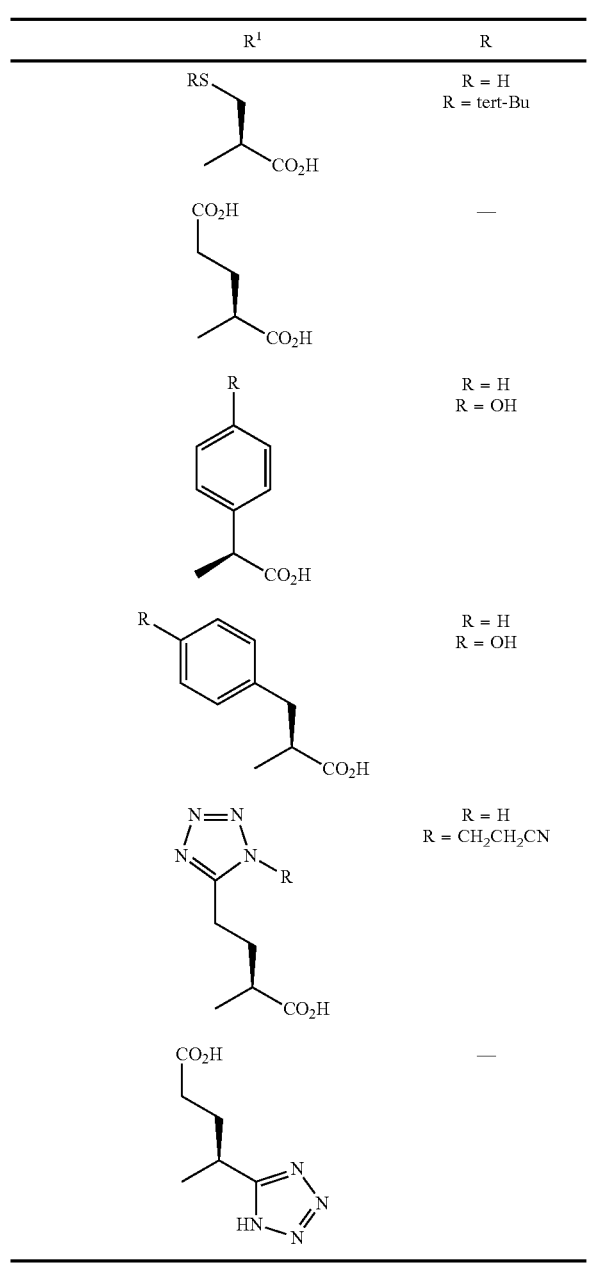 | R = H<br>R = tert-Bu |
| | — |
| | R = H<br>R = OH |
| | R = H<br>R = OH |
| | R = H<br>R = CH₂CH₂CN |
| | — |

It is appreciated that the urea and thiourea compounds described herein may also be advantageous in the preparation of the ligands also described herein due to the sub-nanomolar potency, water solubility, and/or long term stability of these compounds. The thiourea compounds described herein may generally be prepared from commercially available starting materials as described herein.

It is appreciated that in each of the above illustrative pentanedioic acid compounds and thiourea compounds, there is at least one asymmetric carbon atom. Accordingly, the above illustrative formulae are intended to refer both individually and collectively to all stereoisomers as pure enantiomers, or mixtures of enantiomers and/or diastereomers, including but not limited to racemic mixtures, mixtures that include one epimer at a first asymmetric carbon but allow mixtures at other asymmetric carbons, including racemic mixtures, and the like.

In another illustrative embodiment, the binding agent is a thiourea of an amino dicarboxylic acid, such as aspartic acid, glutamic acid, and the like, and another amino dicarboxylic acid, or an analog thereof, such as a binding agent of the formulae

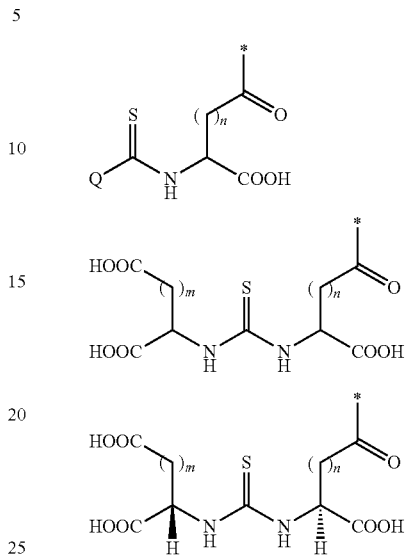

wherein Q is a an amino dicarboxylic acid, such as aspartic acid, glutamic acid, or an analog thereof, n and m are each selected from an integer between 1 and about 6, and (*) represents the point of attachment for the linker L.

In another embodiment, the PSMA ligand includes at least four carboxylic acid groups, or at least three free carboxylic acid groups after the PSMA ligand is conjugated to the agent or linker. It is understood that as described herein, carboxylic acid groups on the PSMA ligand include bioisosteres of carboxylic acids.

Illustratively, the PSMA ligand is a compound of the formulae:

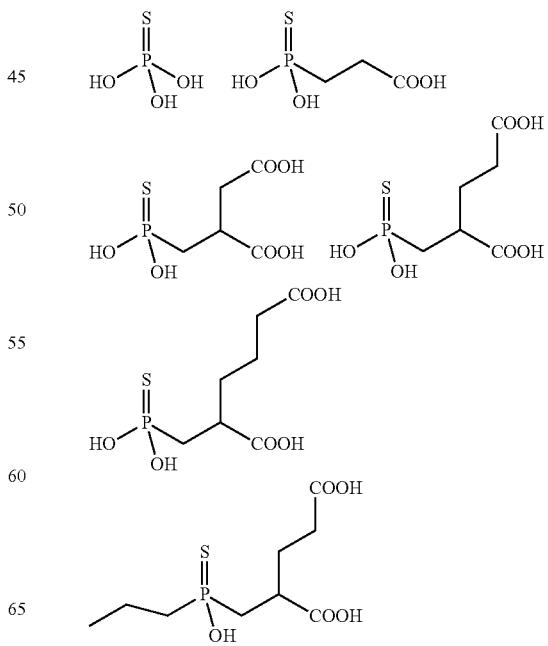

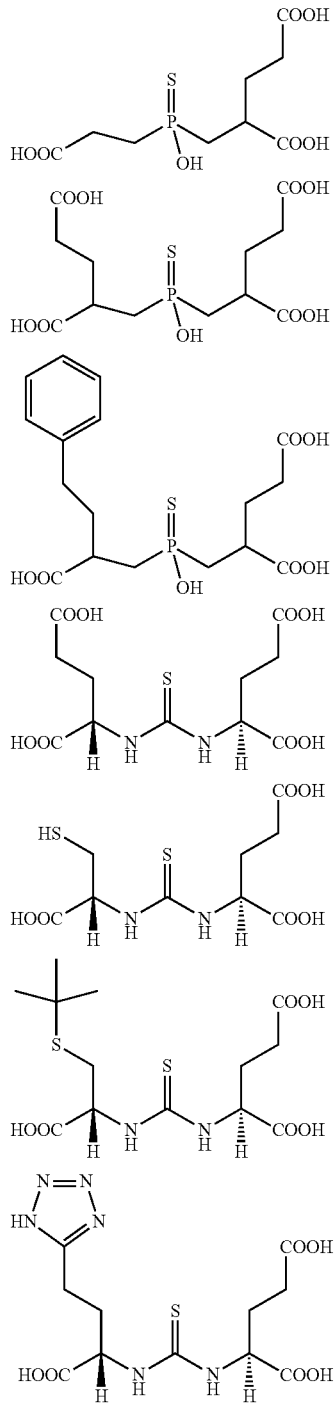
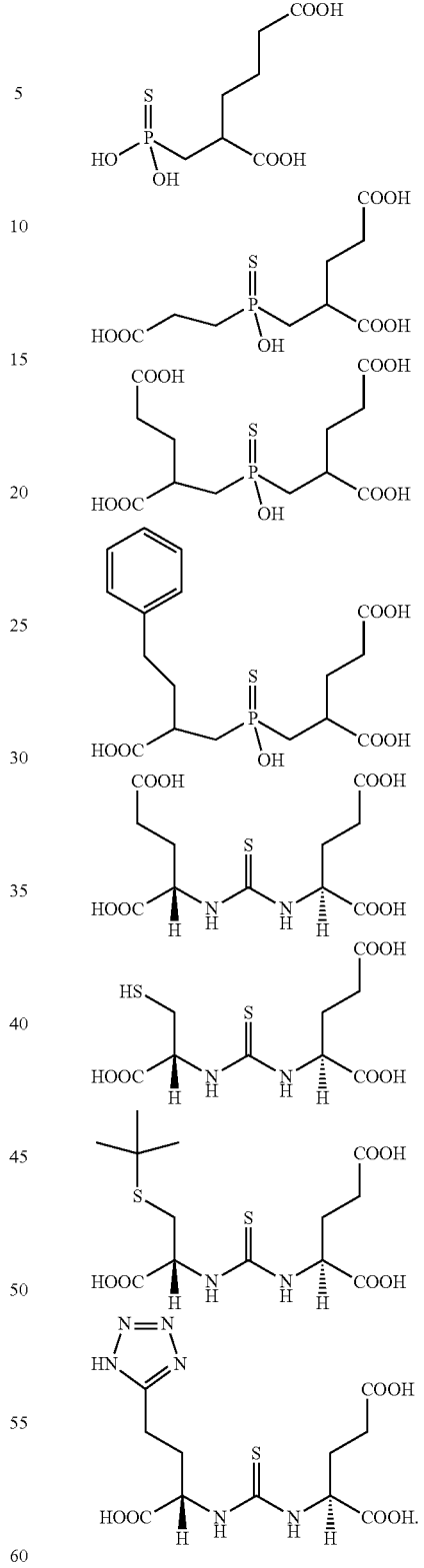
Illustratively, the PSMA ligand is a compound of the formulae:
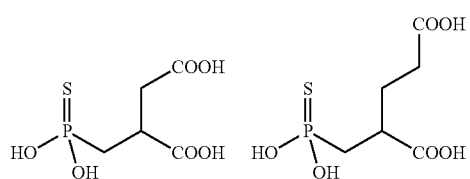
In another embodiment, the PSMA ligand is 2-[3-(1-Carboxy-2-mercapto-ethyl)-thioureido]-pentanedioic acid (thiono-MUPA) or 2-[3-(1,3-Dicarboxy-propyl)-thioureido]-pentanedioic acid (thiono-DUPA).
In another illustrative embodiment, the binding agent is a thiourea of an amino dicarboxylic acid, such as aspartic acid, glutamic acid, and the like, and another amino dicarboxylic acid, or an analog thereof, and the linker is peptide of amino acids, including naturally occurring and non-naturally occurring amino acids. In one embodiment, the linker is a peptide comprising amino acids selected from Glu, Asp, Phe, Cys, beta-amino Ala, and aminoalkylcarboxylic acids, such as Gly, beta Ala, amino valeric acid, amino caproic acid, and the like. In another embodiment, the linker is a peptide consisting of amino acids selected from Glu, Asp, Phe, Cys, beta-amino Ala, and aminoalkylcarboxylic acids, such as Gly, beta Ala, amino valeric acid, amino caproic acid, and the like. In another embodiment, the linker is a peptide comprising at least one Phe. In variations, the linker is a peptide comprising at least two Phe residues, or at least three Phe residues. In another embodiment, the linker is a peptide comprising Glu-Phe or a dipeptide of an aminoalkylcarboxylic acid and Phe. In another embodiment, the linker is a peptide comprising Glu-Phe-Phe or a tripeptide of an aminoalkylcarboxylic acid and two Phe residues. In another embodiment, the linker is a peptide comprising one or more Phe residues, where at least one Phe is about 7 to about 11, or about 7 to about 14 atoms from the binding ligand B. In another embodiment, the linker is a peptide comprising Phe-Phe about 7 to about 11, or about 7 to about 14 atoms from the binding ligand B. It is to be understood that in each of the foregoing embodiments and variations, one or more Phe residues may be replaced with Tyr, or another substituted variation thereof.

In another illustrative embodiment, the binding agent is a thiourea of an amino dicarboxylic acid, such as aspartic acid, glutamic acid, and the like, and another amino dicarboxylic acid, or an analog thereof, and the linker includes one or more aryl or arylalkyl groups, each of which is optionally substituted, attached to the backbone of the linker. In another embodiment, the linker is a peptide comprising one or more aryl or arylalkyl groups, each of which is optionally substituted, attached to the backbone of the linker about 7 to about 11 atoms from the binding ligand B. In another embodiment, the linker is a peptide comprising two aryl or arylalkyl groups, each of which is optionally substituted, attached to the backbone of the linker, where one aryl or arylalkyl group is about 7 to about 11, or about 7 to about 14 atoms from the binding ligand B, and the other aryl or arylalkyl group is about 10 to about 14, or about 10 to about 17 atoms from the binding ligand B.

As described herein, the conjugates are targeted to cells that express or over-express PSMA, using a PSMA binding ligand. Once delivered, the conjugates bind to PSMA. It is understood that in certain embodiments the conjugates remain on the surface of the cell for a period of time sufficient for imaging and/or diagnosis. In other embodiments, the conjugates are internalized in the cell expressing or over-expressing PSMA by endogenous cellular mechanisms, such as endocytosis, for subsequent imaging and/or diagnosis, or treatment. Once internalized, the conjugates may remain intact or be decomposed, degraded, or otherwise altered to allow the release of the agent forming the conjugate. It is appreciated that in imaging and/or diagnostic configurations, the agent may remain intact as the conjugate or be released once it has been internalized into the targeted cell. It is further appreciated that in therapeutic configurations, the agent is advantageously released from the conjugate once it has been internalized into the targeted cell.

In one illustrative embodiment, the drug is an imaging agent. In another illustrative variation, the drug is a diagnostic agent. In another illustrative variation, the drug is an chemotherapeutic agent.

In one aspect, the imaging agent is a radioisotope covalently attached to the linker. In another aspect, the imaging agent is a radioactive isotope, such as a radioactive isotope of a metal, coordinated to a chelating group. Illustrative radioactive metal isotopes include technetium, rhenium, gallium, gadolinium, indium, copper, and the like, including isotopes $^{111}$In, $^{99m}$Tc, $^{64}$Cu, $^{67}$Cu, $^{67}$Ga, $^{68}$Ga, and the like. Additional illustrative examples of radionuclide imaging agents are described in U.S. Pat. No. 7,128,893, the disclosure of which is incorporated herein by reference. Additional illustrative chelating groups are tripeptide or tetrapeptides, including but not limited to tripeptides having the formula:

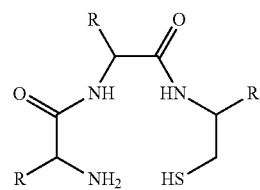

wherein R is independently selected in each instance H, alkyl, heteroalkyl, cycloalkyl, heterocyclyl, alkenyl, alkynyl, aryl, heteroaryl, arylalkyl, heteroarylalkyl, and the like, each of which is optionally substituted. It is to be understood that one R includes a heteroatom, such as nitro, oxygen, or sulfur, and is the point of attachment of linker L. Illustratively, the following chelating groups are described:

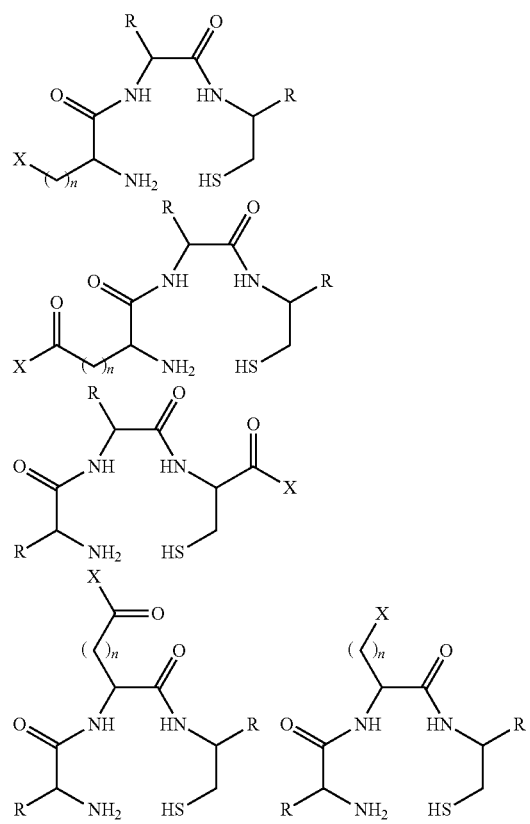

where X is oxygen, nitrogen, or sulfur, and where X is attached to linker L, and n is an integer from 1 to about 5.

In another aspect, the imaging agent is a fluorescent agent. Fluorescent agents include Oregon Green fluorescent agents, including but not limited to Oregon Green 488, Oregon Green 514, and the like, AlexaFluor fluorescent agents, including but not limited to AlexaFluor 488, AlexaFluor 647, and the like, fluorescein, and related analogs, BODIPY fluorescent agents, including but not limited to BODIPY F1, BODIPY 505, and the like, rhodamine fluorescent agents, including but not limited to tetramethylrhodamine, and the like, DyLight fluorescent agents, including but not limited to DyLight 680, DyLight 800, and the like, CW 800, Texas Red, phycoerythrin, and others. Illustrative fluorescent agent are shown in the following illustrative general structures:

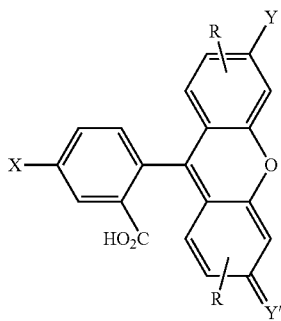

where X is oxygen, nitrogen, or sulfur, and where X is attached to linker L; Y is $OR^a$, $NR^a{}_2$, or $NR^a{}_3{}^+$; and Y' is O, $NR^a$, or $NR^a{}_2{}^+$; where each R is independently selected in each instance from H, fluoro, sulfonic acid, sulfonate, and salts thereof, and the like; and $R^a$ is hydrogen or alkyl.

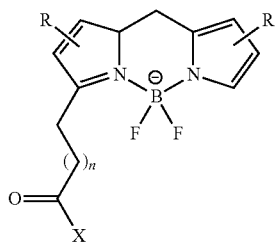

where X is oxygen, nitrogen, or sulfur, and where X is attached to linker L; and each R is independently selected in each instance from H, alkyl, heteroalkyl, and the like; and n is an integer from 0 to about 4.

In another aspect, the imaging agent is a PET imaging agent, or a FRET imaging agent. PET imaging agents $^{18}$F, $^{11}$C, $^{64}$Cu, $^{65}$Cu, and the like. FRET imaging agents include $^{64}$Cu, $^{65}$Cu, and the like. It appreciated that in the case of $^{18}$F, $^{11}$C, the imaging isotope may be present on any part of the linker, or alternatively may be present on a structure attached to the linker. For example in the case of $^{18}$F, fluoroaryl groups, such as fluorophenyl, difluorophenyl, fluoronitrophenyl, and the like are described. For example in the case of $^{11}$C, alkyl and alkyl aryl are described.

In another aspect, the chemotherapeutic agent is a cytotoxic compound. The cytotoxic compounds described herein operate by any of a large number of mechanisms of action. Generally, cytotoxic compounds disrupt cellular mechanisms that are important for cell survival and/or cell proliferation and/or cause apoptosis.

The drug can be any molecule capable of modulating or otherwise modifying cell function, including pharmaceutically active compounds. Suitable molecules can include, but are not limited to: peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; antibiotics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; anti-depressants; H-2 antagonists; anticonvulsants; antinauseants; prostaglandins and prostaglandin analogs; muscle relaxants; anti-inflammatory substances; stimulants; decongestants; antiemetics; diuretics; antispasmodics; antiasthmatics; anti-Parkinson agents; expectorants; cough suppressants; mucolytics; and mineral and nutritional additives.

Further, the drug can be any drug known in the art which is cytotoxic, enhances tumor permeability, inhibits tumor cell proliferation, promotes apoptosis, decreases anti-apoptotic activity in target cells, is used to treat diseases caused by infectious agents, enhances an endogenous immune response directed to the pathogenic cells, or is useful for treating a disease state caused by any type of pathogenic cell. Drugs suitable for use in accordance with this invention include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, taxanes, such as tamoxiphen, taxol, paclitaxel, paclitaxel derivatives, Taxotere®, and the like, maytansines and analogs and derivatives thereof, cyclophosphamide, daunomycin, doxorubicin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O—Ac-seco-cyclopropyl benz[e]indolone, bleomycin and any other antibiotic, nitrogen mustards, nitrosureas, vincristine, vinblastine, and analogs and derivative thereof such as deacetylvinblastine monohydrazide, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used in accordance with the invention include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, and any other art-recognized antimicrobial compound.

Illustrative drugs and other therapeutic agents are described in U.S. Patent Application Publication Nos. US-2005-0002942-A1, US-2001-0031252-A1, and US-2003-0086900-A1. Illustrative imaging agents and diagnostic agents are described in U.S. Patent Application Publication No. US-2004-0033195-A1 and International Patent Application Publication No. WO 03/097647. The disclosures of each of the foregoing patent application publications are incorporated herein by reference.

The invention described herein also includes pharmaceutical compositions comprising an amount of a binding ligand (B) drug delivery conjugate effective to eliminate a population of pathogenic cells in a host animal when administered in one or more doses. The binding ligand drug delivery conjugate is preferably administered to the host animal parenterally, e.g., intradermally, subcutaneously, intramuscularly, intraperitoneally, intravenously, or intrathecally. Alternatively, the binding ligand drug delivery conjugate can be administered to the host animal by other medically useful processes, such as orally, and any effective dose and suitable therapeutic dosage form, including prolonged release dosage forms, can be used.

Examples of parenteral dosage forms include aqueous solutions of the active agent, in an isotonic saline, 5% glucose or other well-known pharmaceutically acceptable liquid carriers such as liquid alcohols, glycols, esters, and amides. The parenteral dosage form in accordance with this invention can be in the form of a reconstitutable lyophilizate comprising the dose of the drug delivery conjugate. In one aspect of the present embodiment, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference, or, alternatively, a slow pump (e.g., an osmotic pump) can be used.

In one illustrative aspect, at least one additional composition comprising a therapeutic factor can be administered to the host in combination or as an adjuvant to the above-detailed methodology, to enhance the binding ligand drug delivery conjugate-mediated elimination of the population of pathogenic cells, or more than one additional therapeutic factor can be administered. The therapeutic factor can be selected from a chemotherapeutic agent, or another therapeutic factor capable of complementing the efficacy of the administered binding ligand drug delivery conjugate.

In one illustrative aspect, therapeutically effective combinations of these factors can be used. In one embodiment, for example, therapeutically effective amounts of the therapeutic factor, for example, in amounts ranging from about 0.1 MIU/m$^2$/dose/day to about 15 MIU/m$^2$/dose/day in a multiple dose daily regimen, or for example, in amounts ranging from about 0.1 MIU/m$^2$/dose/day to about 7.5 MIU/m$^2$/dose/day in a multiple dose daily regimen, can be used along with the binding ligand drug delivery conjugates to eliminate, reduce, or neutralize pathogenic cells in a host animal harboring the pathogenic cells (MIU=million international units; m$^2$=approximate body surface area of an average human).

In another embodiment, chemotherapeutic agents, which are, for example, cytotoxic themselves or can work to enhance tumor permeability, are also suitable for use in the method of the invention in combination with the binding ligand drug delivery conjugates. Such chemotherapeutic agents include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives, Taxotere®, cyclophosphamide, daunomycin, doxorubicin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O—Ac-seco-cyclopropyl benz[e]indolone, bleomycin and any other antibiotic, nitrogen mustards, nitrosureas, vincristine, vinblastine, and analogs and derivative thereof such as deacetylvinblastine monohydrazide, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used in accordance with the invention include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, maytansines and analogs and derivatives thereof, gemcitabine, and any other art-recognized antimicrobial compound.

The therapeutic factor can be administered to the host animal prior to, after, or at the same time as the binding ligand drug delivery conjugates and the therapeutic factor can be administered as part of the same composition containing the binding ligand drug delivery conjugate or as part of a different composition than the binding ligand drug delivery conjugate. Any such therapeutic composition containing the therapeutic factor at a therapeutically effective dose can be used in the present invention.

Additionally, more than one type of binding ligand drug delivery conjugate can be used. Illustratively, for example, the host animal can be treated with conjugates with different vitamins, but the same drug in a co-dosing protocol. In other embodiments, the host animal can be treated with conjugates comprising the same binding ligand linked to different drugs, or various binding ligands linked to various drugs. In another illustrative embodiment, binding ligand drug delivery conjugates with the same or different vitamins, and the same or different drugs comprising multiple vitamins and multiple drugs as part of the same drug delivery conjugate could be used.

In another illustrative aspect, any effective regimen for administering the binding ligand drug delivery conjugates can be used. For example, the binding ligand drug delivery conjugates can be administered as single doses, or can be divided and administered as a multiple-dose daily regimen. In other embodiments, a staggered regimen, for example, one to three days per week can be used as an alternative to daily treatment, and for the purpose of defining this invention such intermittent or staggered daily regimen is considered to be equivalent to every day treatment and within the scope of this invention. In one embodiment, the host is treated with multiple injections of the binding ligand drug delivery conjugate to eliminate the population of pathogenic cells. In another embodiment, the host is injected multiple times (preferably about 2 up to about 50 times) with the binding ligand drug delivery conjugate, for example, at 12-72 hour intervals or at 48-72 hour intervals. In other embodiments, additional injections of the binding ligand drug delivery conjugate can be administered to the patient at an interval of days or months after the initial injections(s) and the additional injections prevent recurrence of the disease state caused by the pathogenic cells.

Illustratively, the binding ligand drug delivery conjugates can be administered parenterally to the animal or patient suffering from the disease state, for example, intradermally, subcutaneously, intramuscularly, intraperitoneally, or intravenously in combination with a pharmaceutically acceptable carrier. In another embodiment, the binding ligand drug delivery conjugates can be administered to the animal or patient by other medically useful procedures and effective doses can be administered in standard or prolonged release dosage forms. In another aspect, the therapeutic method can be used alone or in combination with other therapeutic methods recognized for treatment of disease states mediated by activated macrophages.

Described herein is a method for imaging pathogenic cell populations that express or over-express PSMA.

Described herein is a method for diagnosing diseases and disease states that are related to pathogenic cell populations that express or over-express PSMA. The compounds described herein bind selectively and/or specifically to cells that express or over-express PSMA. Compounds described herein show selectivity between pathogenic cells and normal tissues. Compounds described herein show selectivity among pathogenic cell populations, such as between PSMA expressing LNCaP cells compared to A549 tumors or KB tumos, which do not express PSMA. Compounds described herein exhibit a response that is specific to PSMA binding as indicated by competition studies conducted with the conjugates described herein where binding is determined with the conjugate alone or in the presence of a competing PSMA ligand, such as excess PMPA.

In another embodiment, the conjugate has a binding constant $K_d$ of about 100 nM or less. In another aspect, the conjugate has a binding constant $K_d$ of about 75 nM or less. In another aspect, the conjugate has a binding constant $K_d$ of about 50 nM or less. In another aspect, the conjugate has a binding constant $K_d$ of about 25 nM or less.

In another embodiment, the conjugates described herein exhibit selectivity for PSMA expressing or PSMA over-expressing cells or tissues relative to normal tissues such as blood, hear, lung, liver, spleen, duodenum, skin, muscle, bladder, and prostate, with at least 3-fold selectivity, or at least 5-fold selectivity. In one variation, the conjugates described herein exhibit selectivity for PSMA expressing or PSMA over-expressing cells or tissues relative to normal tissues with at least 10-fold selectivity. It is appreciated that the selectivity observed for imaging is indicative of the selectivity that may be observed in treating disease states responsive to the selective or specific elimination of cells or cell populations that express or over-express PSMA.

The unitary daily dosage of the drug delivery conjugate can vary significantly depending on the host condition, the disease state being treated, the molecular weight of the conjugate, its route of administration and tissue distribution, and the possibility of co-usage of other therapeutic treatments such as radiation therapy. The effective amount to be administered to a patient is based on body surface area, patient weight, and physician assessment of patient condition. Effective doses can range, for example, from about 1 ng/kg to about 1 mg/kg, from about 1 µg/kg to about 500 µg/kg, from about 1 µg/kg to about 100 µg/kg, and from about 1 µg/kg to about 10 µg/kg.

Generally, any manner of forming a conjugate between the bivalent linker (L) and the binding ligand (B), or analog or derivative thereof, between the bivalent linker (L) and the drug, or analog or derivative thereof, including any intervening heteroatoms, can be utilized in accordance with the present invention. Also, any art-recognized method of forming a conjugate between the spacer linker, the releasable linker, and one or more heteroatoms to form the bivalent linker (L) can be used. The conjugate can be formed by direct conjugation of any of these molecules, for example, through hydrogen, ionic, or covalent bonds. Covalent bonding can occur, for example, through the formation of amide, ester, disulfide, or imino bonds between acid, aldehyde, hydroxy, amino, sulfhydryl, or hydrazo groups.

The synthetic methods are chosen depending upon the selection of the optionally included heteroatoms or the heteroatoms that are already present on the spacer linkers, releasable linkers. the drug, and/or the binding ligand. In general, the relevant bond forming reactions are described in Richard C. Larock, "Comprehensive Organic Transformations, a guide to functional group preparations," VCH Publishers, Inc. New York (1989), and in Theodora E. Greene & Peter G. M. Wuts, "Protective Groups ion Organic Synthesis," 2d edition, John Wiley & Sons, Inc. New York (1991), the disclosures of which are incorporated herein by reference.

More specifically, disulfide groups can be generally formed by reacting an alkyl or aryl sulfonylthioalkyl derivative, or the corresponding heteroaryldithioalkyl derivative such as a pyridin-2-yldithioalkyl derivative, and the like, with an alkylenethiol derivative. For example, the required alkyl or aryl sulfonylthioalkyl derivative may be prepared according to the method of Ranasinghe and Fuchs, Synth. Commun. 18(3), 227-32 (1988), the disclosure of which is incorporated herein by reference. Other methods of preparing unsymmetrical dialkyl disulfides are based on a trans-thiolation of unsymmetrical heteroaryl-alkyl disulfides, such as 2-thiopyridinyl, 3-nitro-2-thiopyridinyl, and like disulfides, with alkyl thiol, as described in WO 88/01622, European Patent Application No. 0116208A1, and U.S. Pat. No. 4,691,024, the disclosures of which are incorporated herein by reference. Further, carbonates, thiocarbonates, and carbamates can generally be formed by reacting an hydroxy-substituted compound, a thio-substituted compound, or an amine-substituted compound, respectively, with an activated alkoxycarbonyl derivative having a suitable leaving group.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

Illustrative derivatives include, but are not limited to, both those compounds that may be synthetically prepared from the compounds described herein, as well as those compounds that may be prepared in a similar way as those described herein, but differing in the selection of starting materials. It is to be understood that such derivatives may include prodrugs of the compounds described herein, compounds described herein that include one or more protection or protecting groups, including compounds that are used in the preparation of other compounds described herein.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical —$(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl) aminoalkyl, alkylcarbonylaminoalkyl, N—($C_1$-$C_6$ alkyl) alkylcarbonylaminoalkyl, cyano, and nitro; or $Z^X$ is selected from —$CO_2R^4$ and —$CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by conventional routes for the methods described herein, utilizing known procedures (see generally, Remington: The Science and Practice of Pharmacy, (21$^{st}$ ed., 2005)).

The term "administering" as used herein includes all means of introducing the compounds and compositions described herein to the patient, including, but are not limited to, intravenous (iv), and the like. The compounds and compositions described herein may be administered in unit dosage forms and/or formulations containing conventional nontoxic pharmaceutically-acceptable carriers, adjuvants, and vehicles.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

Depending upon the disease as described herein, the route of administration and/or whether the compounds and/or compositions are administered locally or systemically, a wide range of permissible dosages are contemplated herein, including doses falling in the range from about 1 μg/kg to about 1 g/kg. The dosages may be single or divided, and may be administered according to a wide variety of protocols, including q.d., b.i.d., t.i.d., or even every other day, once a week, once a month, once a quarter, and the like. In each of these cases it is understood that the total daily, weekly, monthly, or quarterly dose corresponds to the therapeutically effective amounts described herein.

In addition to the foregoing illustrative dosages and dosing protocols, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The following examples further illustrate specific embodiments of the invention; however, the following illustrative examples should not be interpreted in any way to limit the invention.

EXAMPLES

The compounds described herein may be prepared by conventional organic synthetic methods. In addition, the compounds described herein may be prepared as indicated below. Unless otherwise indicated, all starting materials and reagents are available from commercial supplies. All amino acid starting materials were purchased from Chem-Impex Int (Chicago, Ill.). $^1$H NMR spectra were obtained using a Bruker 500 MHz cryoprobe, unless otherwise indicated.

Example

General synthesis of PSMA imaging agent conjugates. Illustrated by synthesis of a 14-atom linker compound, where B is a PSMA binding ligand as described herein.

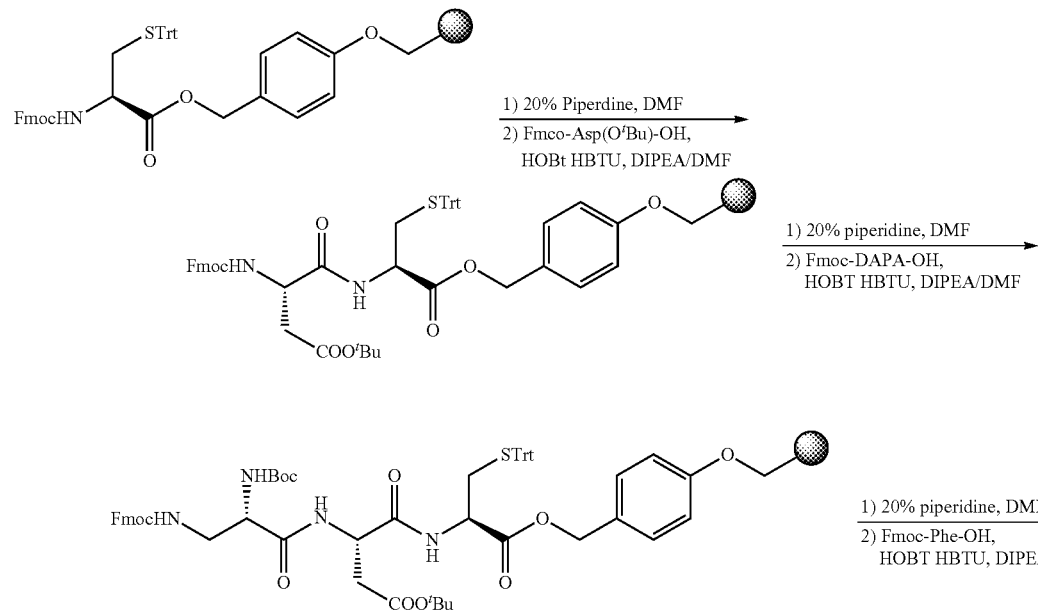

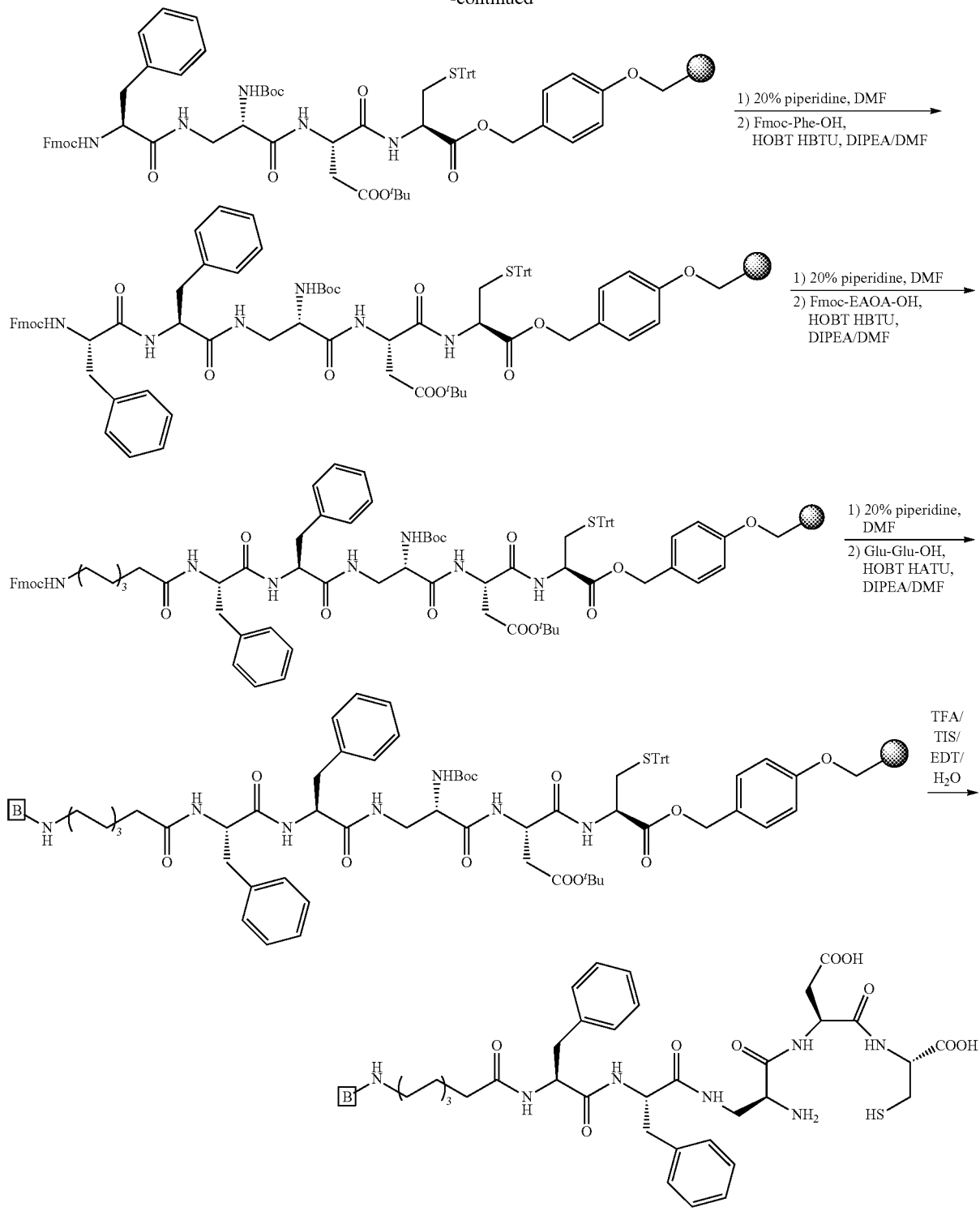

Compounds are synthesized using standard fluorenylmethyloxycarbonyl (Fmoc) solid phase peptide synthesis (SPPS) starting from Fmoc-Cys(Trt)-Wang resin (Novabiochem; Catalog #04-12-2050). Compounds are purified using reverse phase preparative HPLC (Waters, xTerra $C_{18}$ 10 μm; 19×250 mm) A=0.1 TFA, B=Acetonitrile (ACN); λ=257 nm; Solvent gradient: 5% B to 80% B in 25 min, 80% B wash 30 min run, (61%). Purified compounds are analyzed using reverse phase analytical HPLC (Waters, X-Bridge $C_{18}$ 5 μm; 3.0×15 mm); A=0.1 TFA, B=ACN; λ=257 nm, 5% B to 80% B in 10 min, 80% B wash 15 min run. $C_{47}H_{65}N_2O_{17}S$; MW=1060.13 g/mol; white solid; $R_f$=7.7 min; $^1$H NMR (DMSO-$d_6$/$D_2O$) δ 0.93 (m, 2H); 1.08 (m, 5H); 1.27 (m, 5H); 1.69 (m, 2H); 1.90 (m, 2H); 1.94 (m, 2H); 2.10 (m, 2H); 2.24 (q, 2H); 2.62 (m, 2H); 2.78 (m, 4H); 2.88 (dd, 1H); 2.96 (t, 2H); 3.01 (dd, 1H); 3.31 (dd, 1H); 3.62 (dd, 1H); 3.80 (q, 1H, αH); 4.07 (m, 1H, αH); 4.37 (m, 1H, αH); 4.42 (m, 2H, αH); 4.66 (m, 1H, αH); 7.18 (m, 10H, Ar—H): LC-MS=1061 (M+H)₊; ESI-MS=1061 (M+H)⁺.

Example 5

General synthesis of PSMA imaging agent conjugates. Illustrated by synthesis of a 6-atom linker compound, where B is a PSMA binding ligand as described herein.

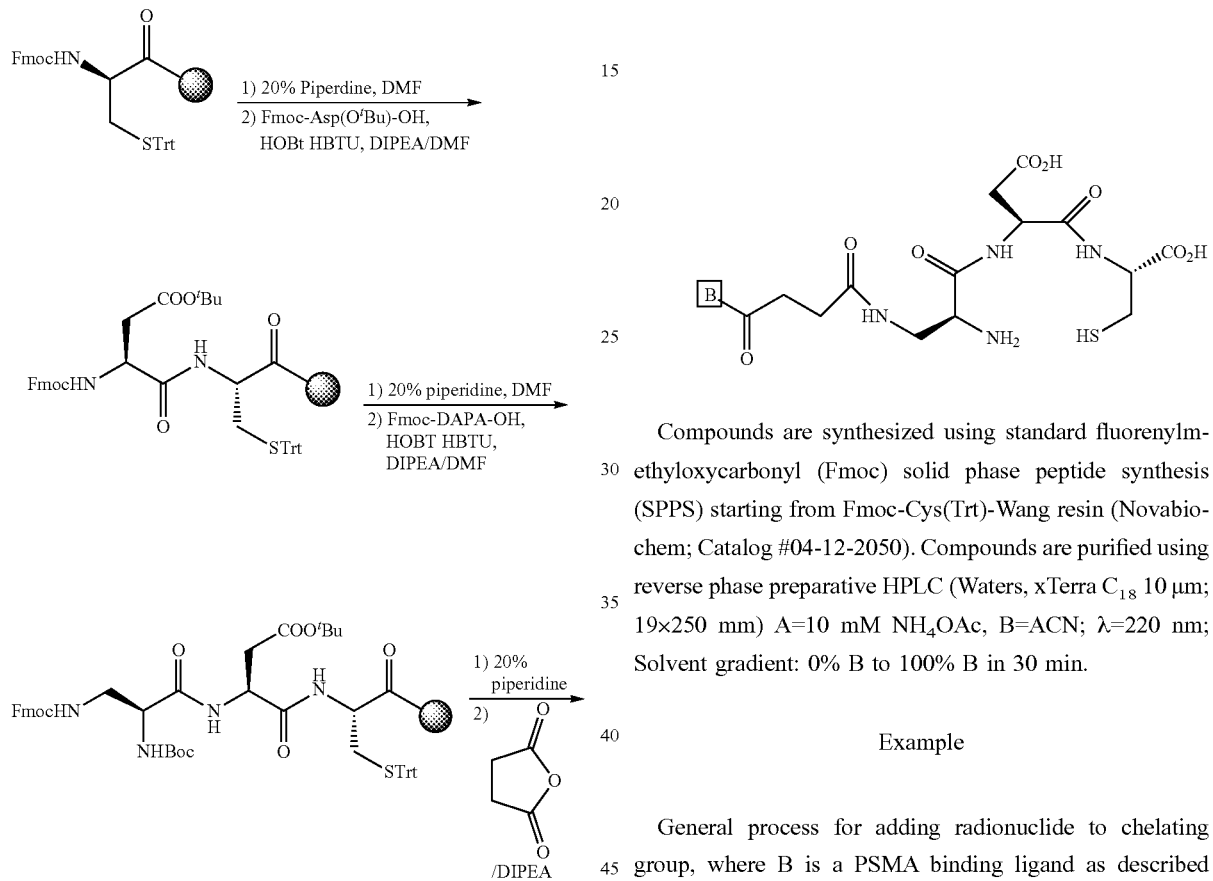

Compounds are synthesized using standard fluorenylmethyloxycarbonyl (Fmoc) solid phase peptide synthesis (SPPS) starting from Fmoc-Cys(Trt)-Wang resin (Novabiochem; Catalog #04-12-2050). Compounds are purified using reverse phase preparative HPLC (Waters, xTerra C$_{18}$ 10 μm; 19×250 mm) A=10 mM NH$_4$OAc, B=ACN; λ=220 nm; Solvent gradient: 0% B to 100% B in 30 min.

Example

General process for adding radionuclide to chelating group, where B is a PSMA binding ligand as described herein.

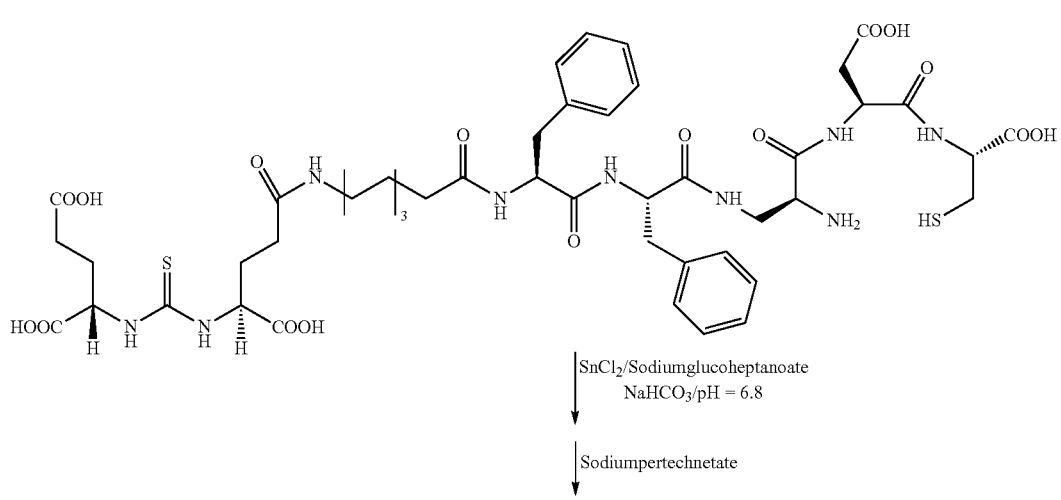

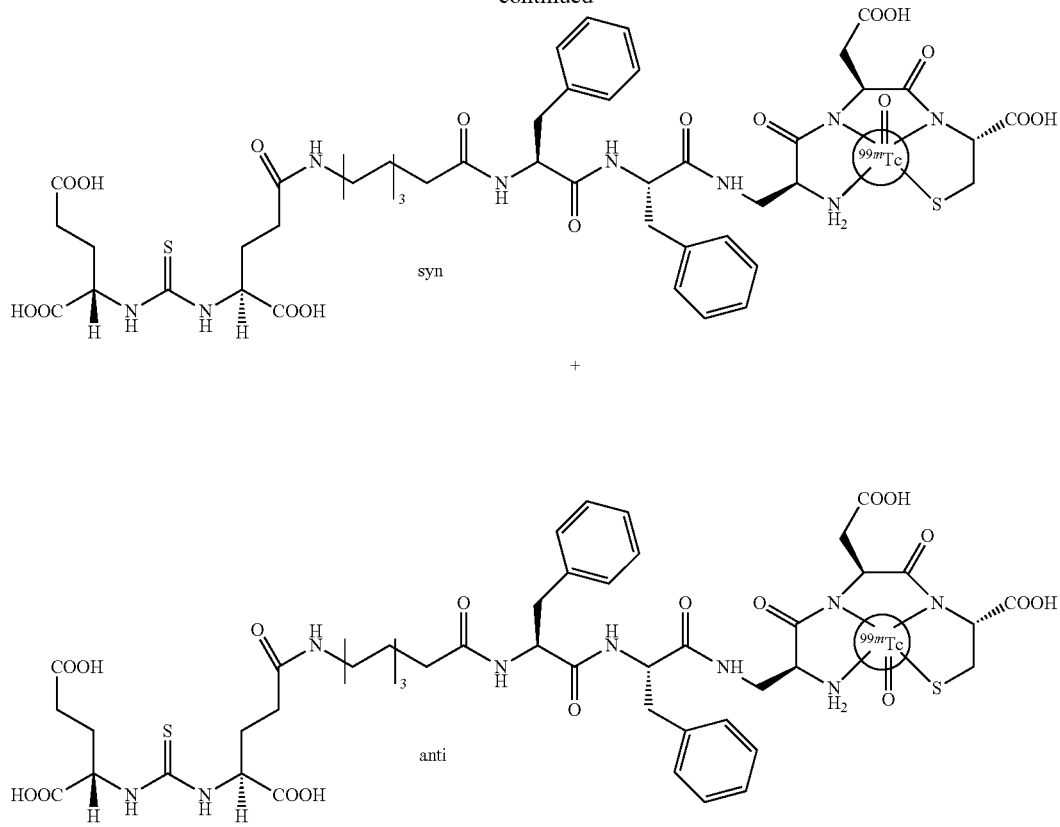

HPLC grade Millipore filtered water (50 mL) was added to a 100 mL bottle and argon was purged for at least 10 min. Sodium α-D-glucoheptonate dihydrate (800 mg) was dissolved in argon purged water (5 mL). Stannous chloride dihydrate (10 mg) was dissolved in 0.02 M HCl (10 mL) while bubbling argon. Stannous chloride (0.8 mL) was added to the sodium glucoheptonate solution under argon. SK28 (1.4 mg) was added to the sodium glucoheptonate/stannous chloride solution under argon. The pH of the reaction mixture was adjusted to 6.8±0.2 using 0.1 N NaOH. Argon purged water (5.2 mL) was added to the reaction mixture to make total volume as 10 mL. 1.0 mL of reaction mixture was dispensed to each vial (10 vials) under argon atmosphere and lyophilized for 36-48 h. The vials were sealed with rubber stoppers and aluminum seals under argon atmosphere to make SK28 formulation kits. The formulation kit vials were stored at −20° C. until they used.

Labeling compounds with $^{99m}$Tc. Radio labeling of compounds with $^{99m}$Tc may be performed according to published procedures. A formulation vial was warmed to room temperature for 10 min and heated in a boiling water bath for 3 min. Then 15 mCi of sodium pertechnetate $^{99m}$Tc (1.0 mL) was injected and an equal volume of gas was withdrawn from the vial to normalize the pressure. The vial was heated in the boiling water bath for 15-20 min and then cooled to room temperature before using in the experiment. Radiochemical purity was analyzed by radioactive TLC (>98%), that shows syn and anti isomers of the radio labeled compound.

Example. Compounds VC3 and VC4

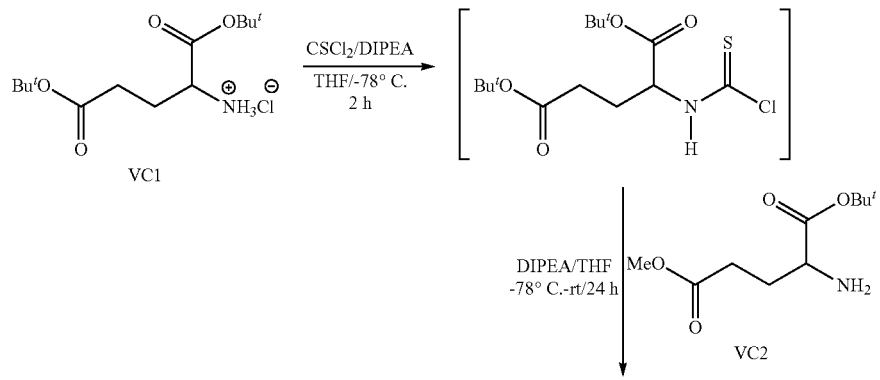

-continued

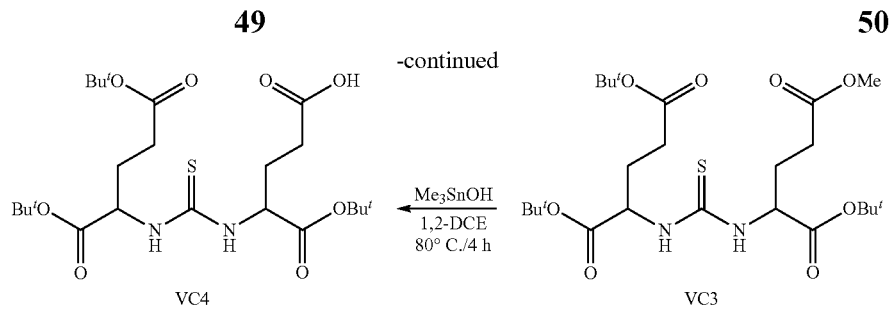

Compound VC3. A solution of aminoesterhydrochloride VC1 (1.19 g, 4.603 mmol) in THF (25 mL) was added dropwise to a cooled (−78° C.) solution of CSCl$_2$ (0.388 mL, 5.063 mmol) in THF (5 mL) over a period of 45-minutes with constant stirring. During the addition of VC1, DIPEA (2.4 mL, 13.809 mmol) was added simultaneously dropwise to the reaction mixture. The reaction mixture was stirred at −78° C. for additional 2 h. After 2 h, a solution of VC2 (1.0 g, 4.603 mmol) in THF (20 mL) and DIPEA (1.6 mL, 9.21 mmol) was added to the reaction mixture simultaneously dropwise for 45-minutes. The reaction mixture was further stirred for overnight while the temperature warmed to ambient condition. Excess THF was evaporated and the residue was dissolved in saturated NH$_4$Cl solution (100 mL). The residue was extracted with EtOAc (4×50 mL), washed with H$_2$O (1×100 mL), brine (50 mL) and dried over anhydrous Na$_2$SO$_4$. After filtration, the organic solvent was evaporated and the residue was purified using silicagel column chromatography (10-30% EtOAc:Hexane) to VC3 as colorless solid (0.752 g, 32%); LC-MS=519.6 [M+H]$^+$; $^1$H NMR spectroscopy also confirmed the structure.

Compound VC4. VC3 (0.30 g, 0.578 mmol) was dissolved in 1,2-dichloroethane and after addition of trimethyltin hydroxide (0.313 g, 1.735 mmol), the mixture was heated at 80° C. and monitored by TLC or LC-MS until the reaction mixture indicated ~90% consumption of VC3, ca. 4 h. The reaction mixture was cooled to room temperature and concentrated in vacuo, and the residue was dissolved in ethyl acetate (50 mL). The organic layer was washed with aqueous solution of KHSO$_4$ (0.01 N, 2×25 mL). The organic layer was washed with brine (25 mL) and dried over anhydrous sodium sulfate, and evaporated. The residue was purified using silicagel column chromatography (EtOAc) to VC4 as colorless liquid (0.152 g, 52%); LC-MS=505.4 [M+H]$^+$; $^1$H NMR spectroscopy also confirmed the structure.

The following additional examples may be prepared according to the procedures described herein:

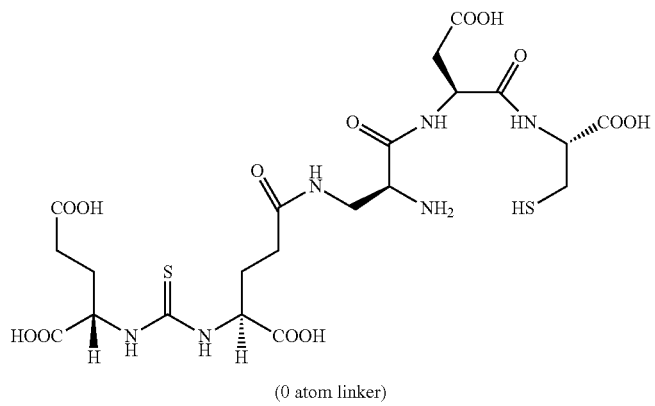

(0 atom linker)

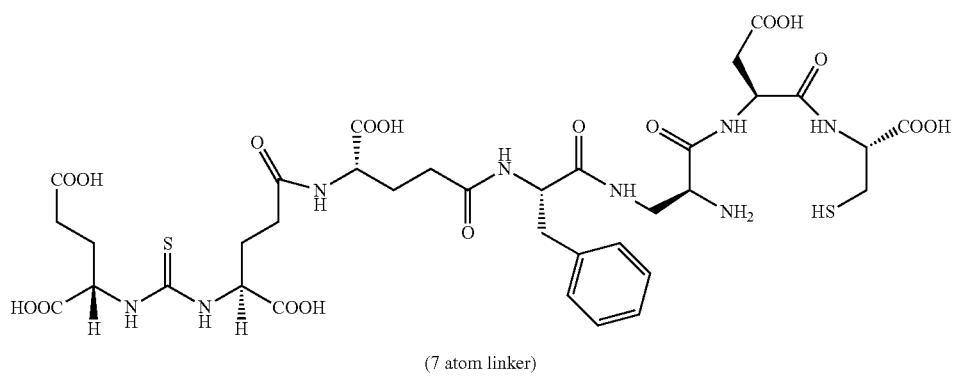

(7 atom linker)

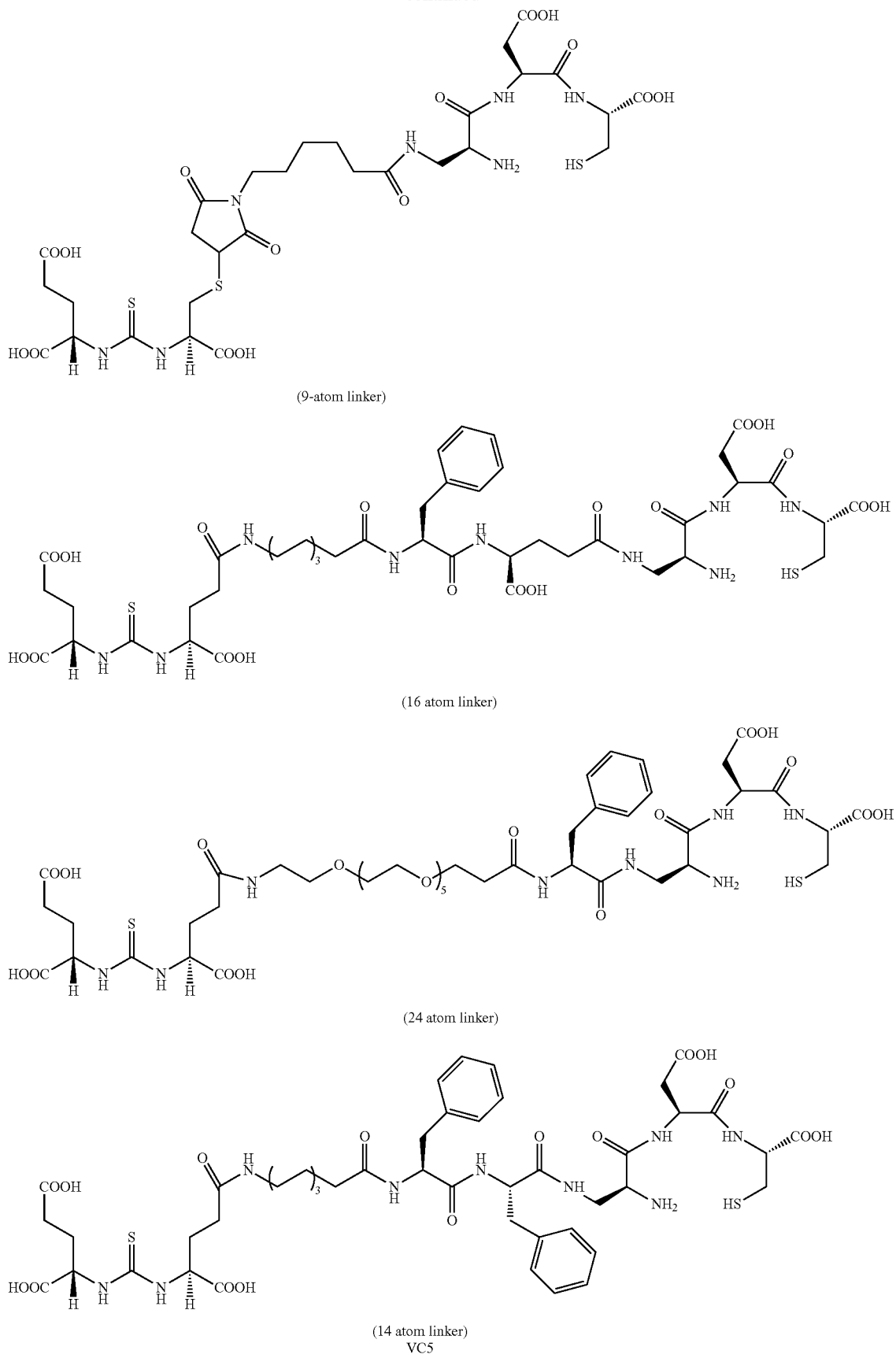

-continued
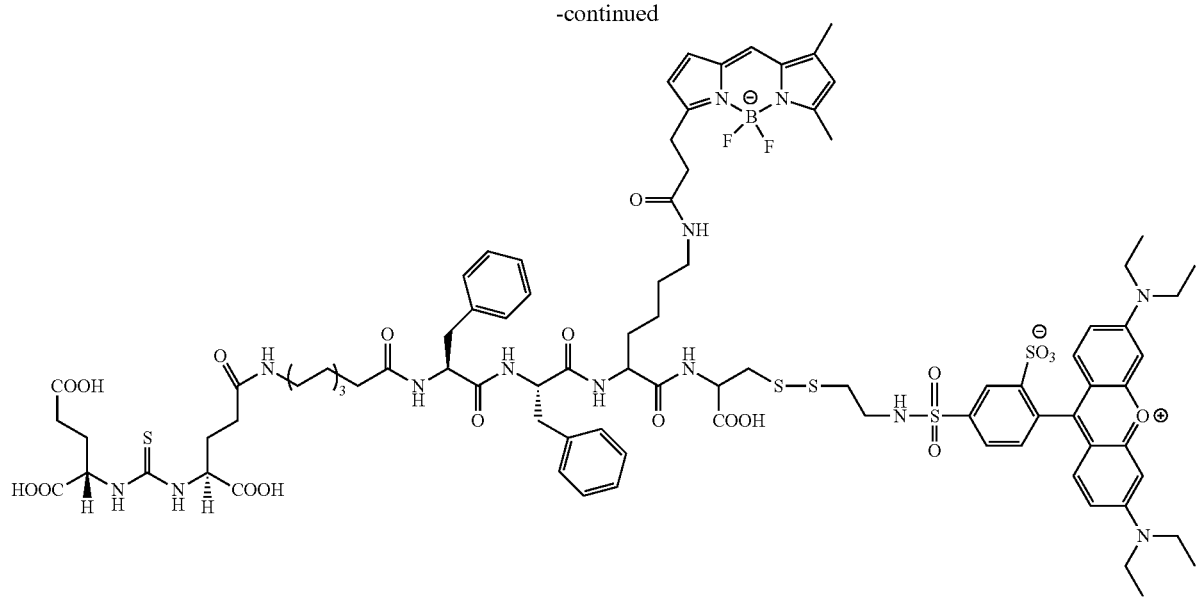
(21/26 atom linker)
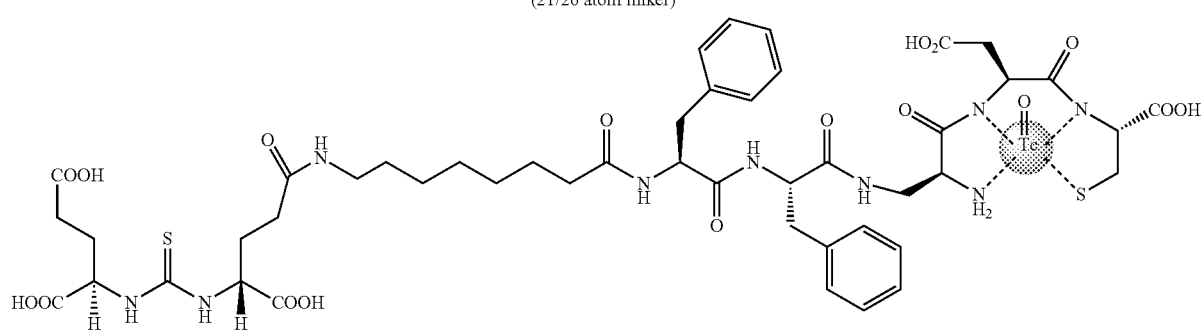
(15 atom liker)
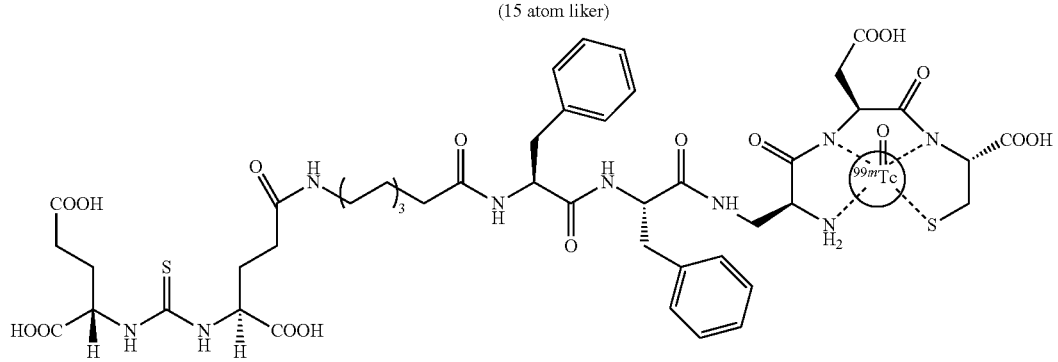
syn-VC6
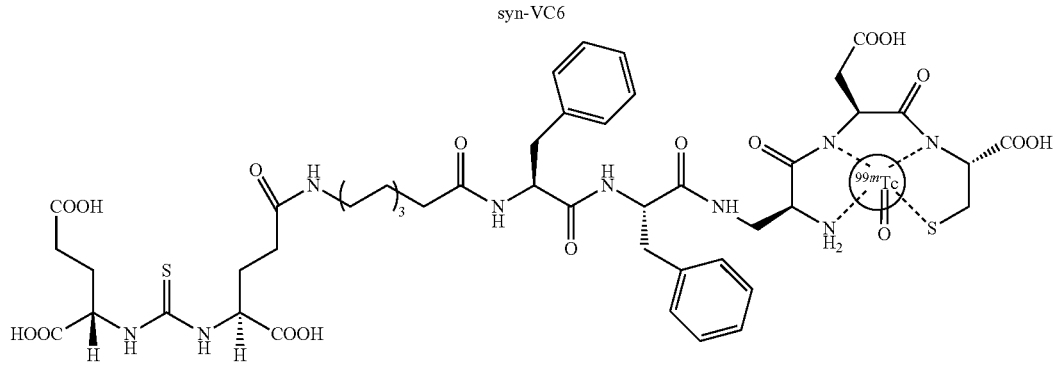
anti-VC6

-continued
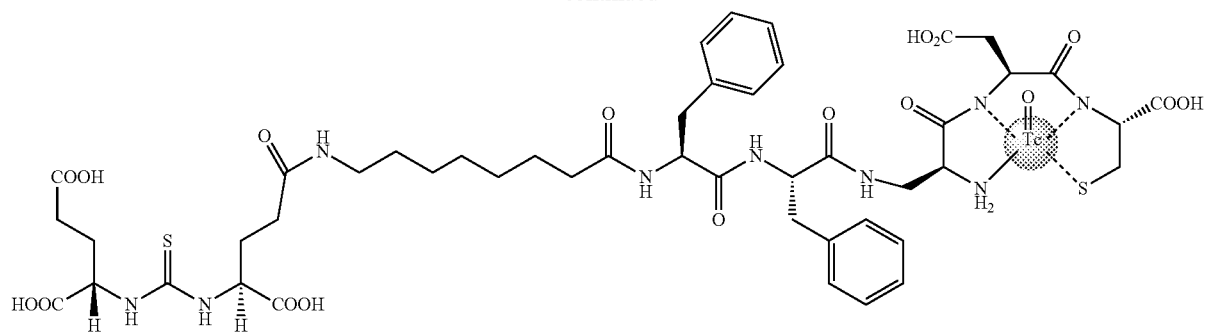
(15 atom linker)
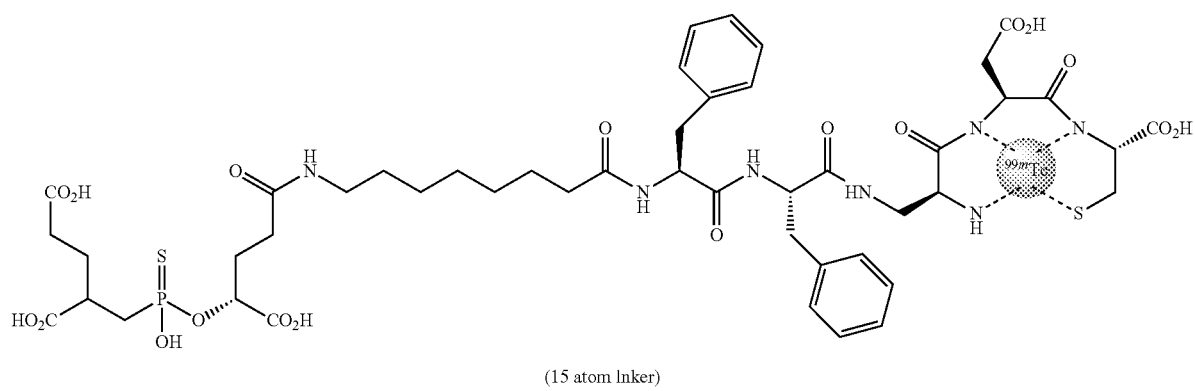
(15 atom linker)
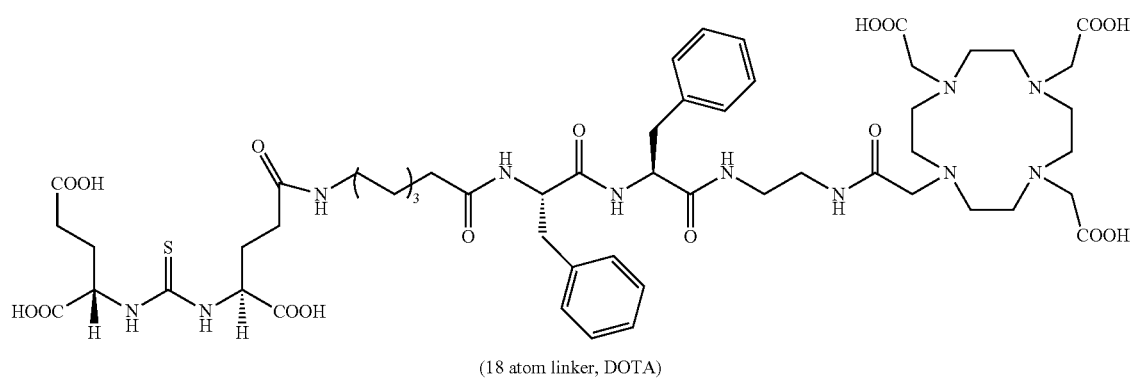
(18 atom linker, DOTA)
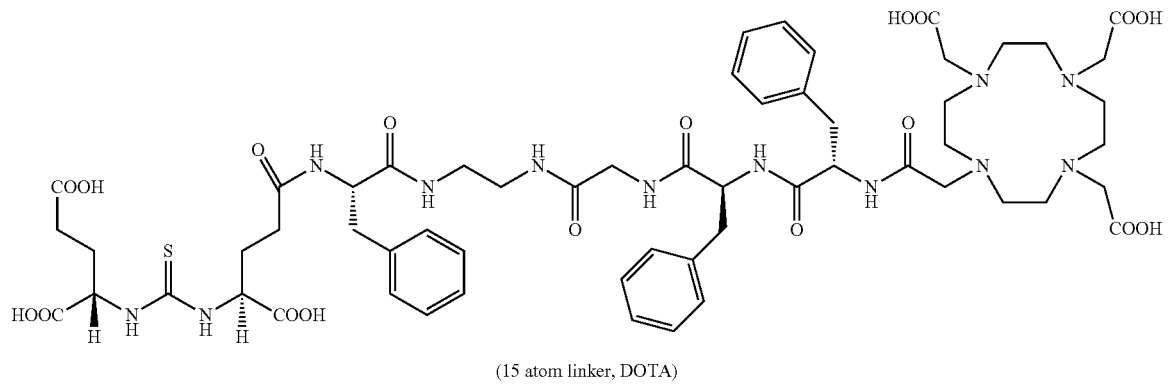
(15 atom linker, DOTA)

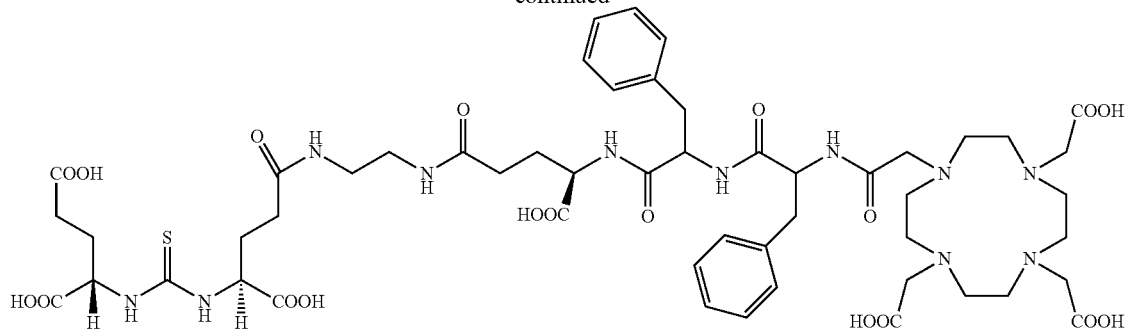

(14 atom linker, DOTA)

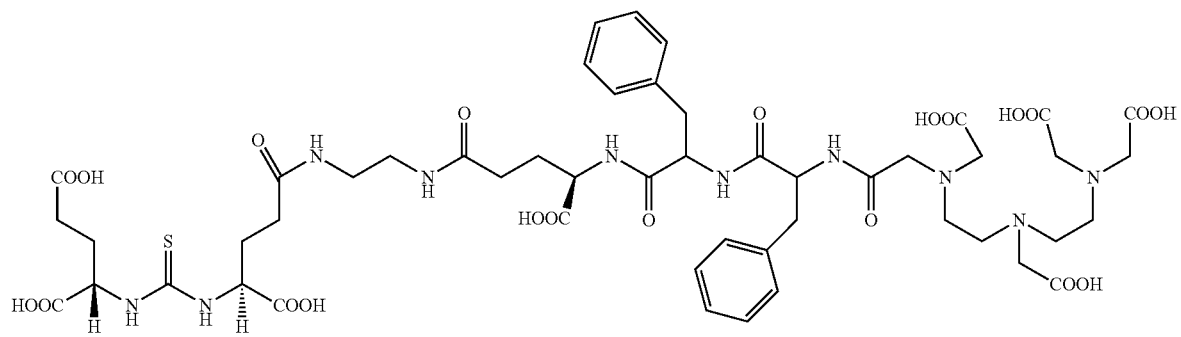

(14 atom linker, DTPA)

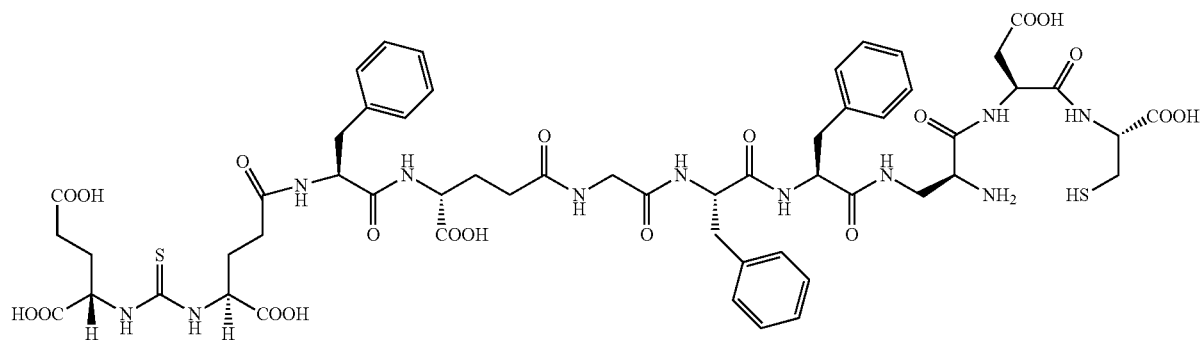

(17 atom linker, DTPA)

Example

General synthesis of PSMA imaging agent conjugates using Universal PSMA (DUPA) resin illustrated for a 2-atom linker, and FITC, where B is a PSMA binding ligand as described herein. These conjugates may also be used for detecting circulating tumor cells in prostate cancer patients.

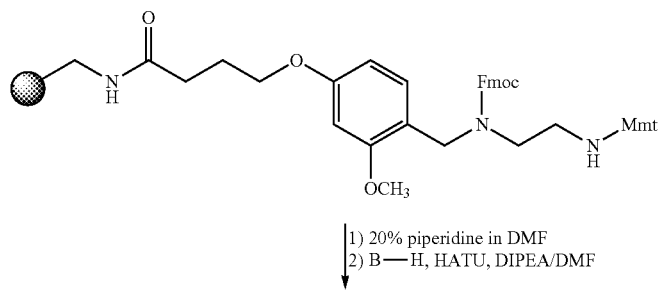

1) 20% piperidine in DMF
2) B—H, HATU, DIPEA/DMF

-continued

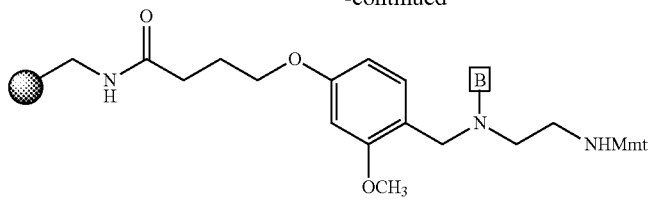

1M HOBt in DCM/TFE (1:1)
to resin swollen in DCM

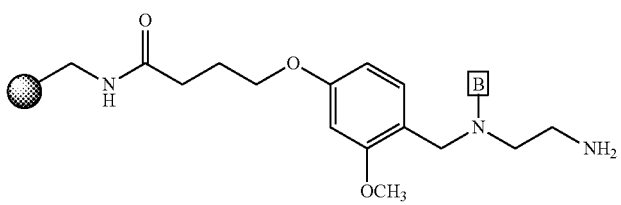

1) FITC, DIPEA/DMF
2) TFA/TIPS/H₂O (95:2.5:2.5)

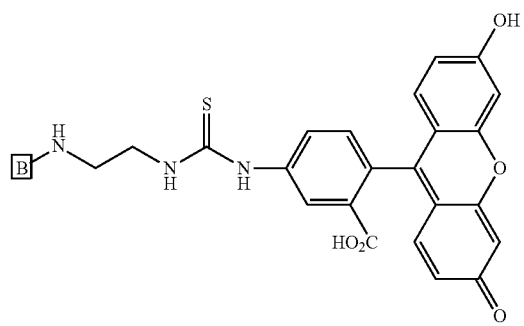

Synthesis of PSMA universal resin. Universal PSMA ligand (thio-DUPA) resin is synthesized using Universal NovaTag™ resin (Novabiochem; Catalog #04-12-3910). Fmoc group are deprotected using 20% piperidine/DMF (N,N-dimethylformamide), after swelling the resin with DCM (CH$_2$Cl$_2$) and DMF. Optionally protected binding ligands B are coupled using HATU [2-(1H-7-azabenzotriazol-1-yl)-1,3,3-tetramethyl uronium hexafluorophosphate] and DIPEA (N,N-diisopropylethylamine) in DMF. The pendant Mmt (4-Methoxytrityl) is removed with 1M HOBT (1-Hyroxybenzotriazole) in DCM/TFE (trifluoroethanol). The resin intermediate can be washed with DMF and used immediately in subsequent synthetic steps or washed with DCM/DMF and then with MeOH, and dried for later use.

Universal PSMA resin is reacted with commercially available FITC (1.25 eq) in the presence of DIPEA (4 eq) in DMF to yield 2 atom linker constructs. The final compound is cleaved from the resin using a mixture of TFA (trifluoro acetic acid), TIPS (triisopropylsilane), and water. Purification is by reverse phase preparative HPLC (Waters, xTerra C$_{18}$ 5 μm; 19×150 mm) A=10 mM NH$_4$OAc, B=ACN; λ=488 nm; Solvent gradient: 1% B to 50% B in 25 min, 80% B wash 40 min run, (63%). The final compound is also analyzed using reverse phase analytical HPLC (Waters, X-Bridge C$_{18}$ 5 μm; 3.0×15 mm); A=10 mM NH$_4$OAc, B=ACN; λ=488 nm, 1% B to 50% B in 10 min, 80% B wash 15 min run.

Example

General synthesis of PSMA imaging agent conjugates using Universal PSMA (DUPA) resin, illustrated with a 16-atom linker, and FITC, where B is a PSMA binding ligand as described herein.

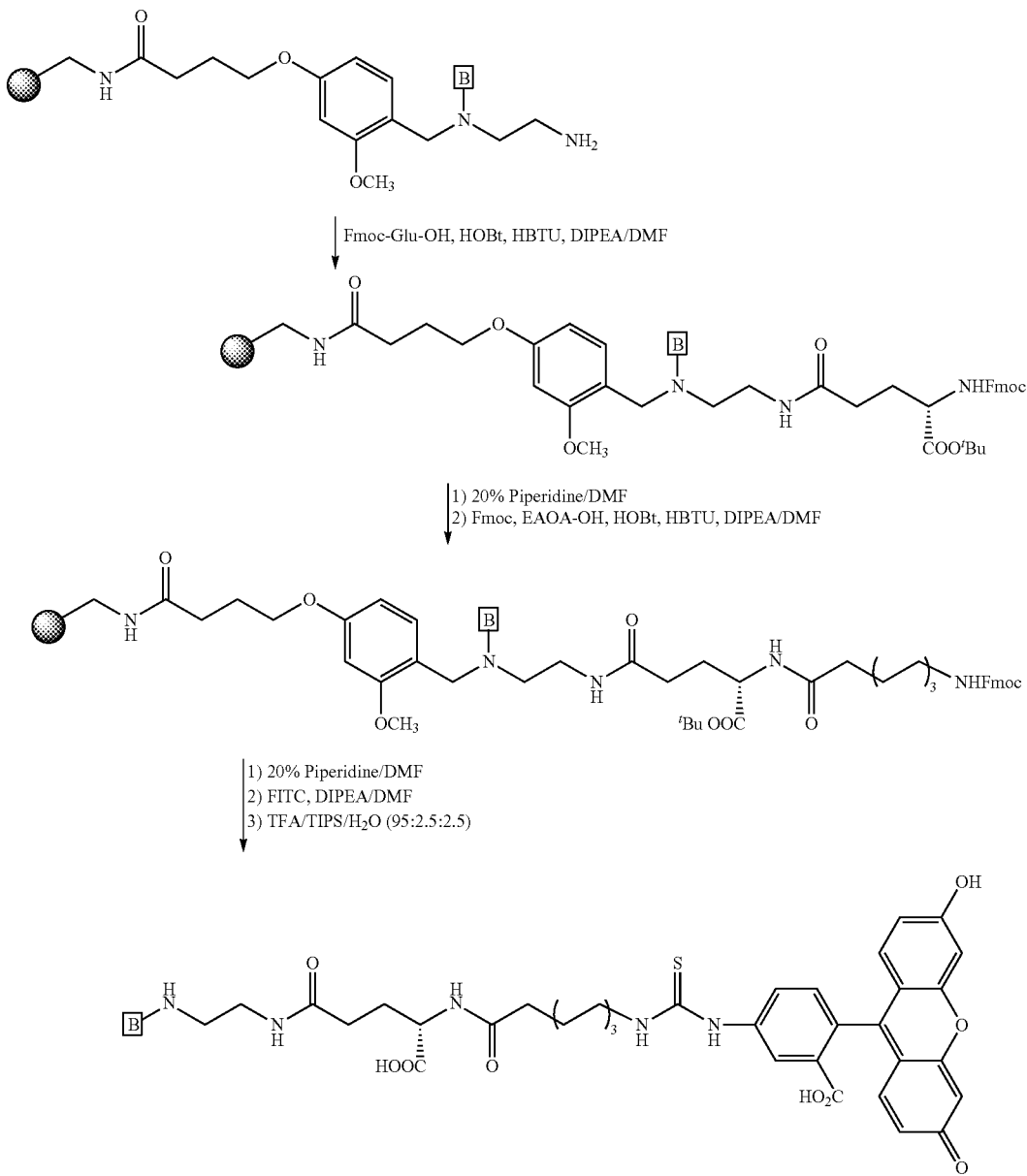

Universal PSMA resin is coupled with Fmoc-Glu-(O'Bu)-OH and Fmoc-EAOA (8-aminooctonoic acid) using standard Fmoc SPPS. After conjugating with fluoresceinisothiocyanate (1.25 eq) in the presence of DIPEA (4 eq) in DMF, the 16 atom linker compound is cleaved from the resin using TFA/TIPS/H$_2$O. Purification is performed using reverse phase preparative HPLC (Waters, xTerra C$_{18}$ 5 µm; 19×150 mm) A=10 mM NH$_4$OAc, B=ACN; λ=488 nm; Solvent gradient: 1% B to 50% B in 25 min, 80% B wash 40 min run, (57%). Analysis is performed using reverse phase analytical HPLC (Waters, X-Bridge C$_{18}$ 5 µm; 3.0×150 mm); A=10 mM NH$_4$OAc, B=ACN; λ=488 nm, 1% to 50% B in 10 min, 80% B wash 15 min run.

Example

Compounds VC8, VC9, and VC10. VC7 (1.1 equiv) is prepared as described herein, and added to a vial containing one of the following near infra red dyes, Alexafluor 647 C2 maleimide (MW ~1300) or Dylight 680 maleimide or IR800CW maleimide, followed by addition of dry DMSO (200 uL) and DIPEA (20 eq). The mixture was stirred under an atmosphere of argon for overnight. LCMS analysis showed the formation of conjugates in 60-80% yield and the dye conjugates were purified using reverse phase preparative HPLC (Waters, xTerra C$_{18}$ 10 µm; 19×250 mm) A=20 mM NH$_4$OAc, B=Acetonitrile (ACN); λ=280 nm; Solvent gradient: 5% B to 80% B in 30 min. Purified dye conjugates were confirmed by LCMS (Waters, X-Bridge C$_{18}$ 5 µm; 3.0×15 mm); A=10 mM NH$_4$OAc, B=Acetonitrile (ACN); λ=280 nm, 1% to 30% or 50% B in 10 min. LC-MS for Alexafluor647 conjugate VC8 (Expected M.W=2360.13) =1021.5 [(M+2H)/2]$^+$; LC-MS for Dylight 680 conjugate VC9 (C$_{90}$H$_{119}$N$_{13}$O$_{30}$S$_4$; MW=1991.24 g/mol)=996.3 [(M+2H)/2]$^+$; LC-MS for IR800CW conjugate VC10 (C$_{99}$H$_{122}$N$_{13}$Na$_3$O$_{33}$S$_5$; MW=2251.4 g/mol)=1093.7 [(M+2H)/2]$^+$.

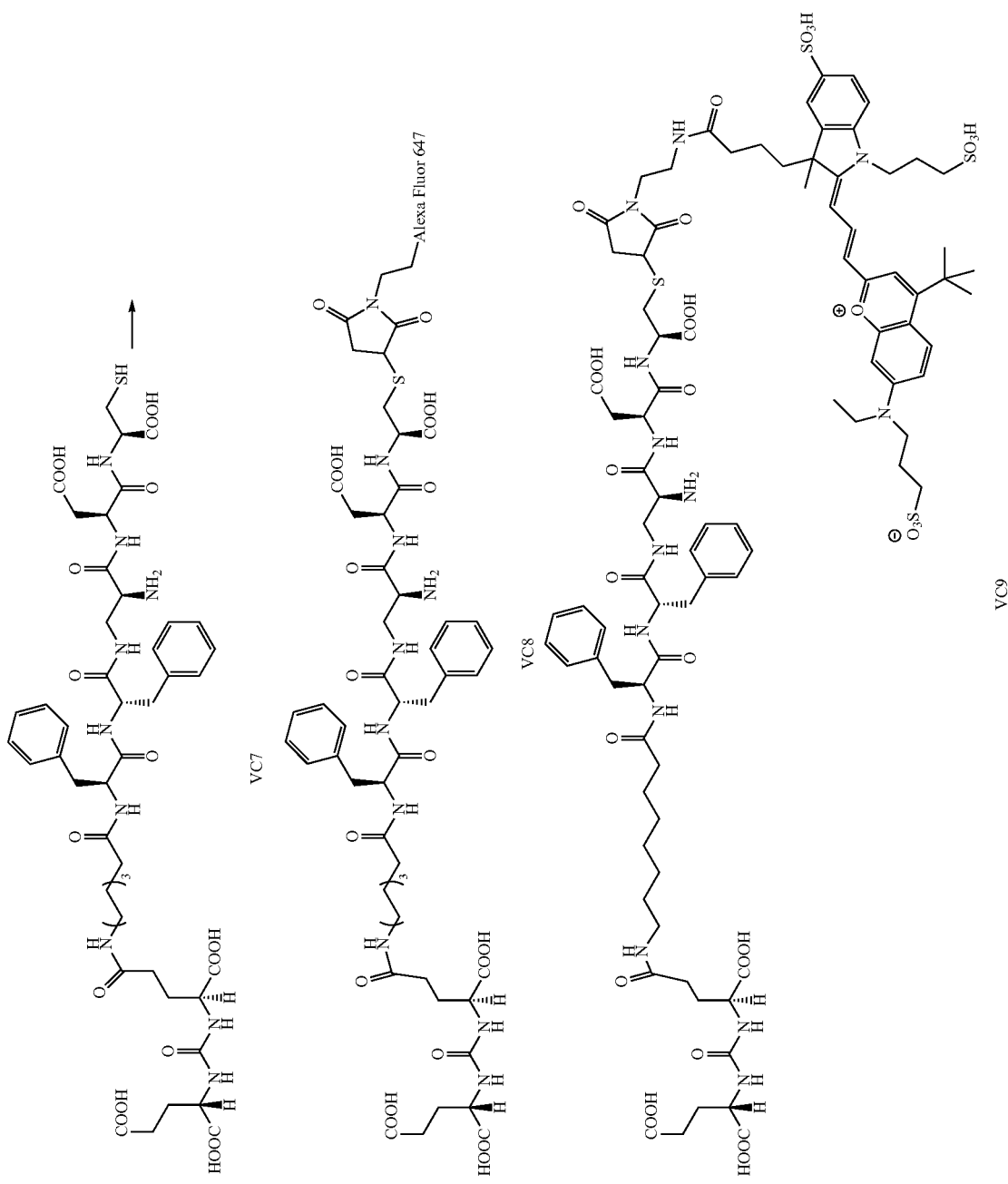

-continued
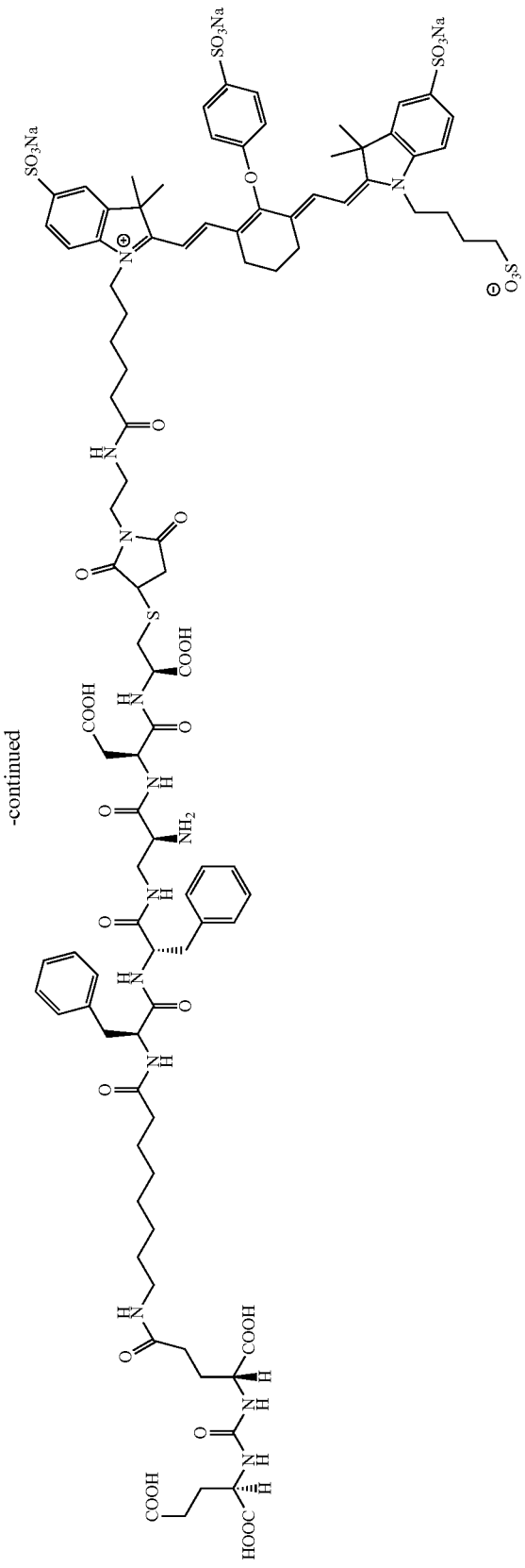
VC10
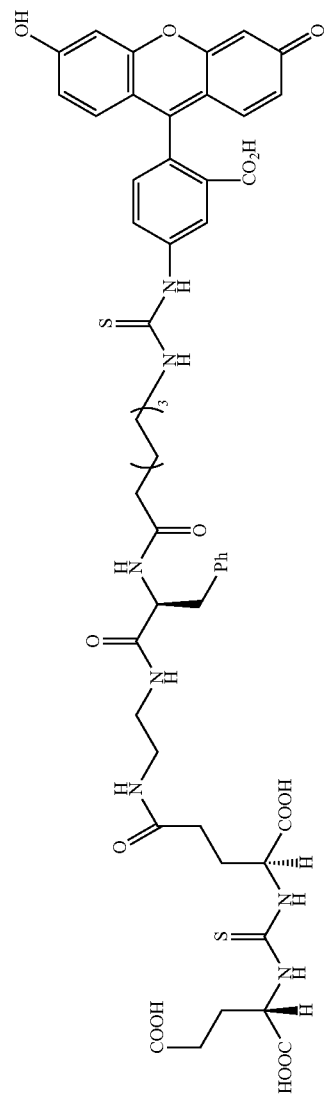
(15 atom linker, FITC)

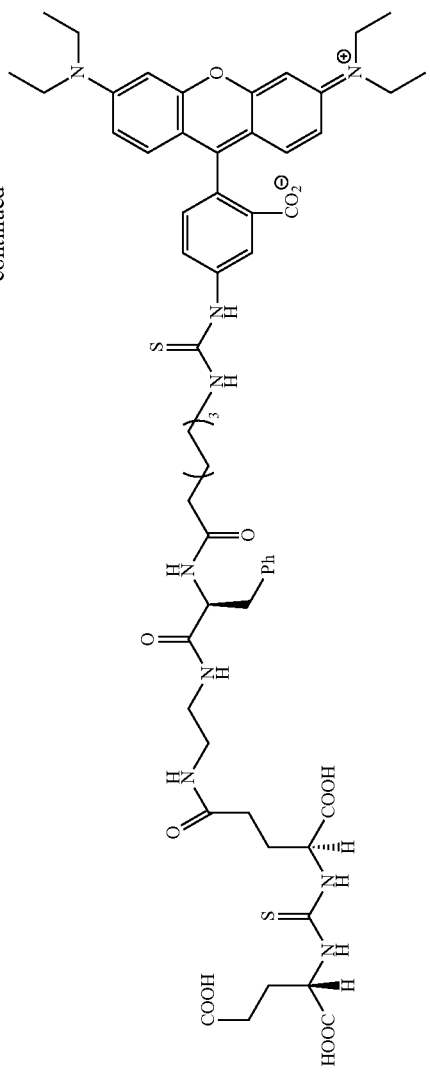
(15 atom linker, Rhodamine)
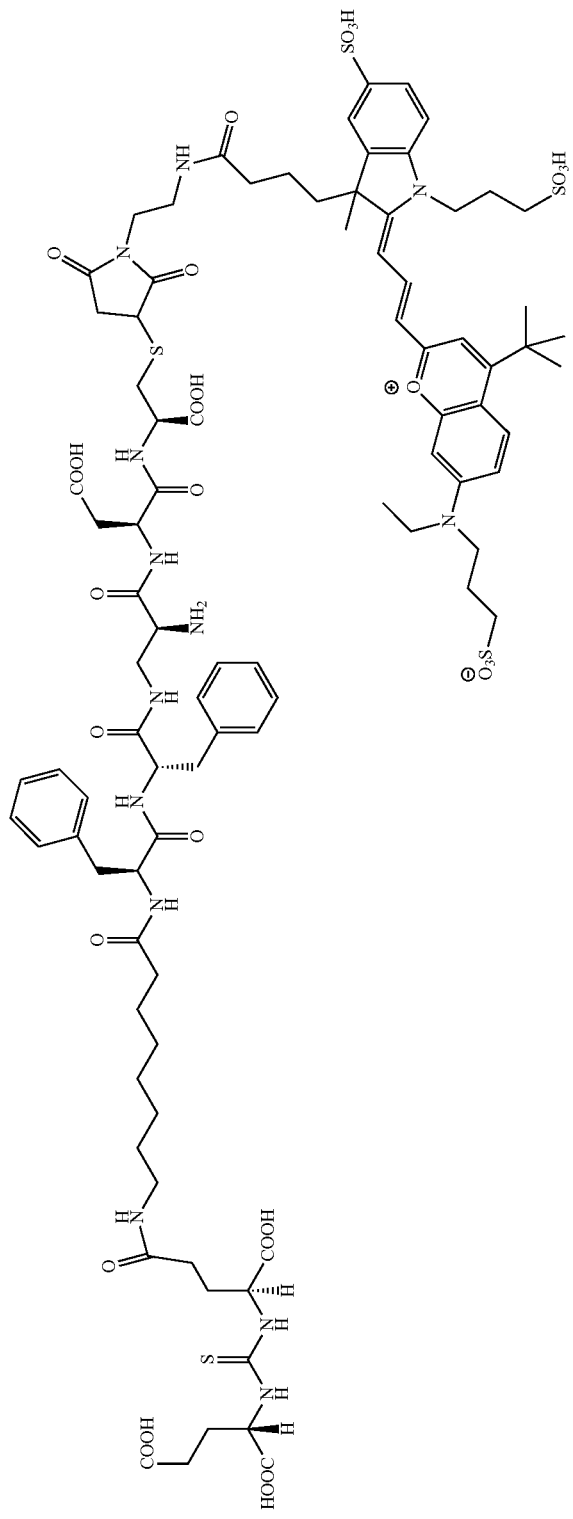
(31 atom linker, Dylight 680)

-continued
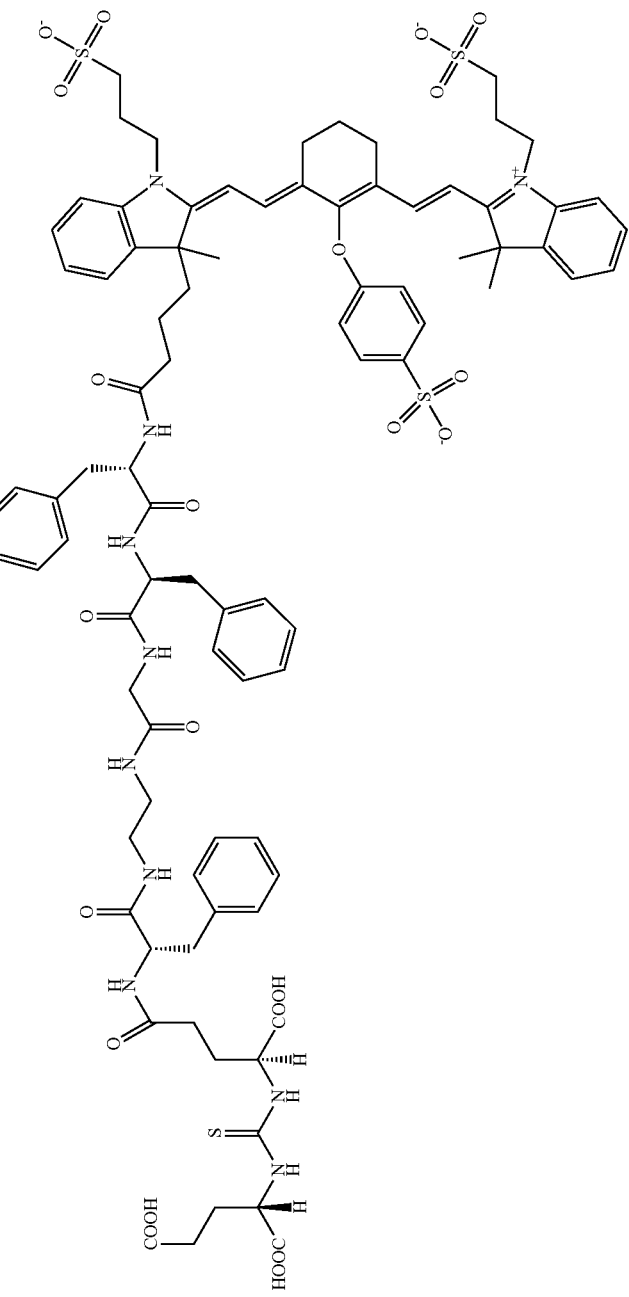
(15 atom linker, Dylight 800)
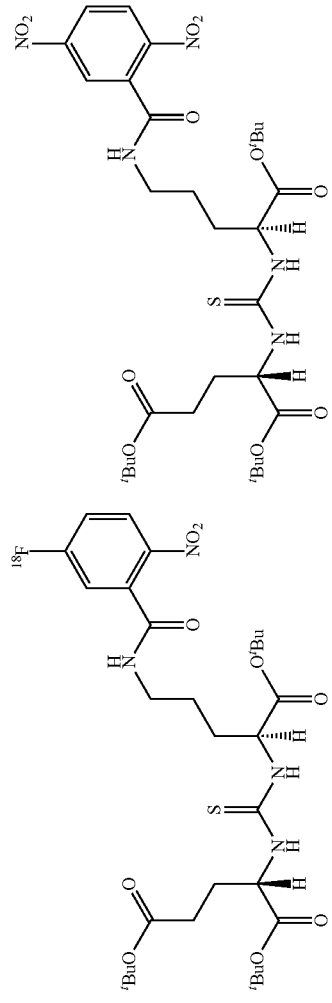
(0 atom linker, PET precursor)
(0 atom linker, PET)

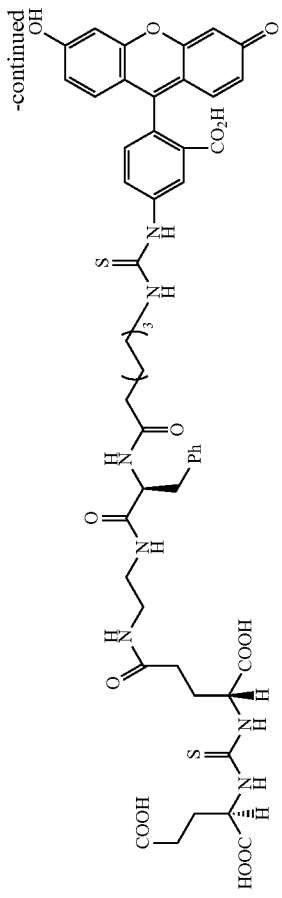
(15 atom linker, FITC)
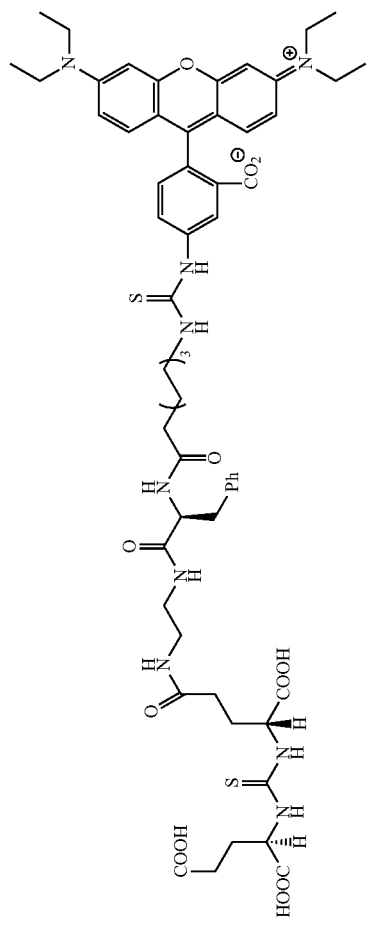
(15 atom linker, Rhodamine)
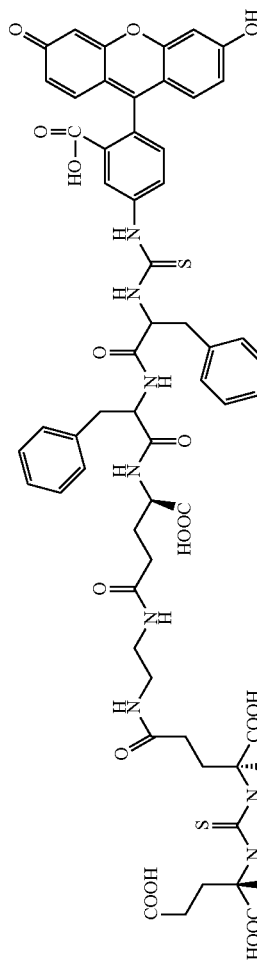
(14 atom linker, FITC)

-continued
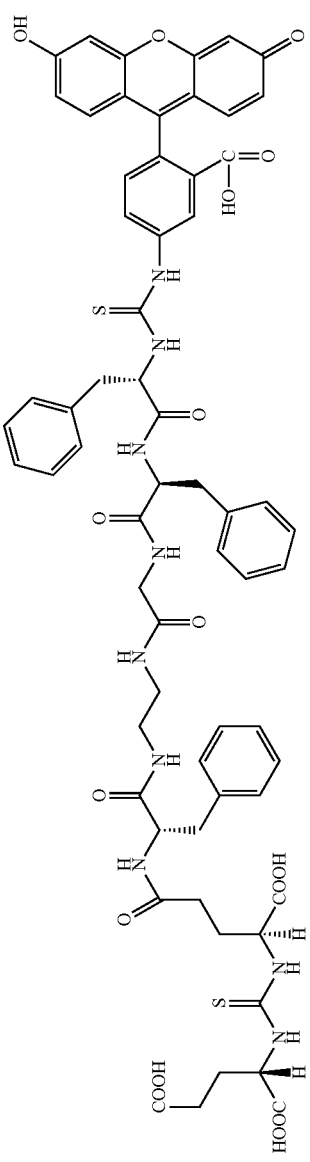
(15 atom linker, FITC)
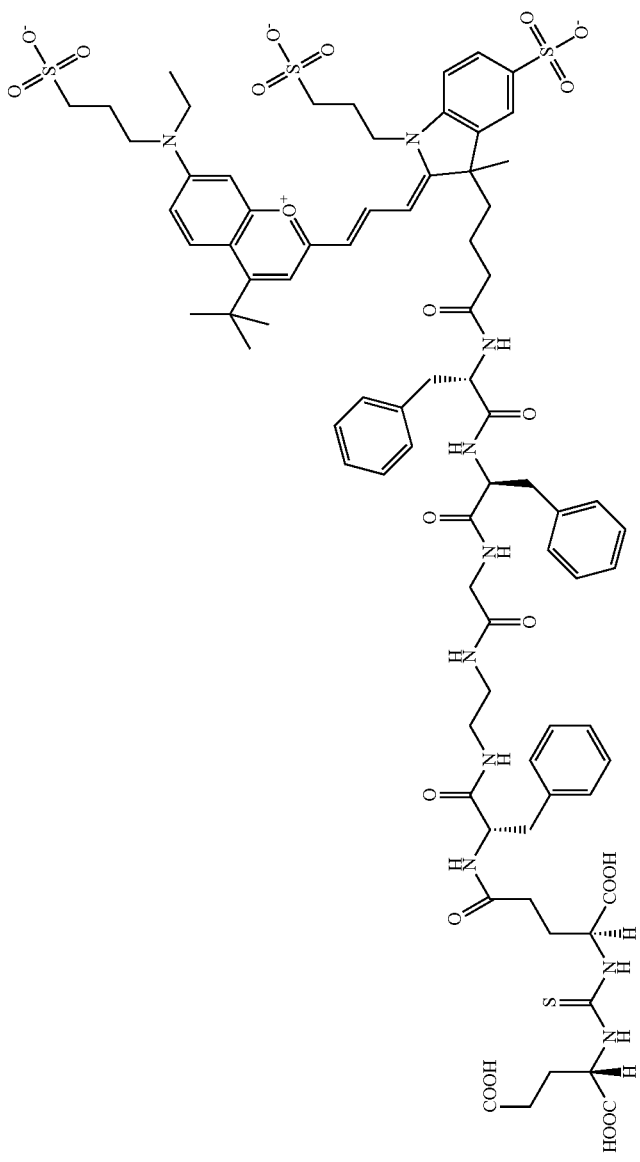
(16 atom linker, DyLight 680)

-continued
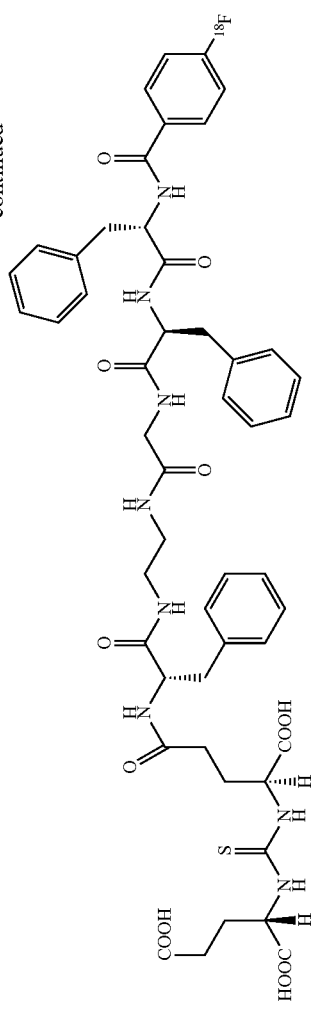
(15 atom linker, PET)
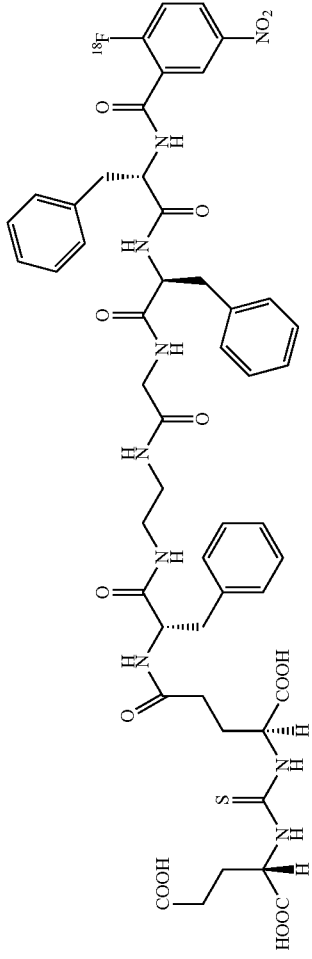
(15 atom linker, PET)
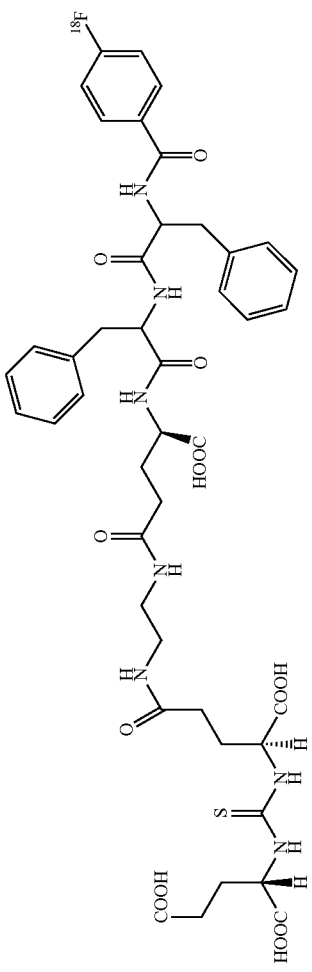
(14 atom linker, PET)

The following additional examples may be prepared according to the procedures described herein:
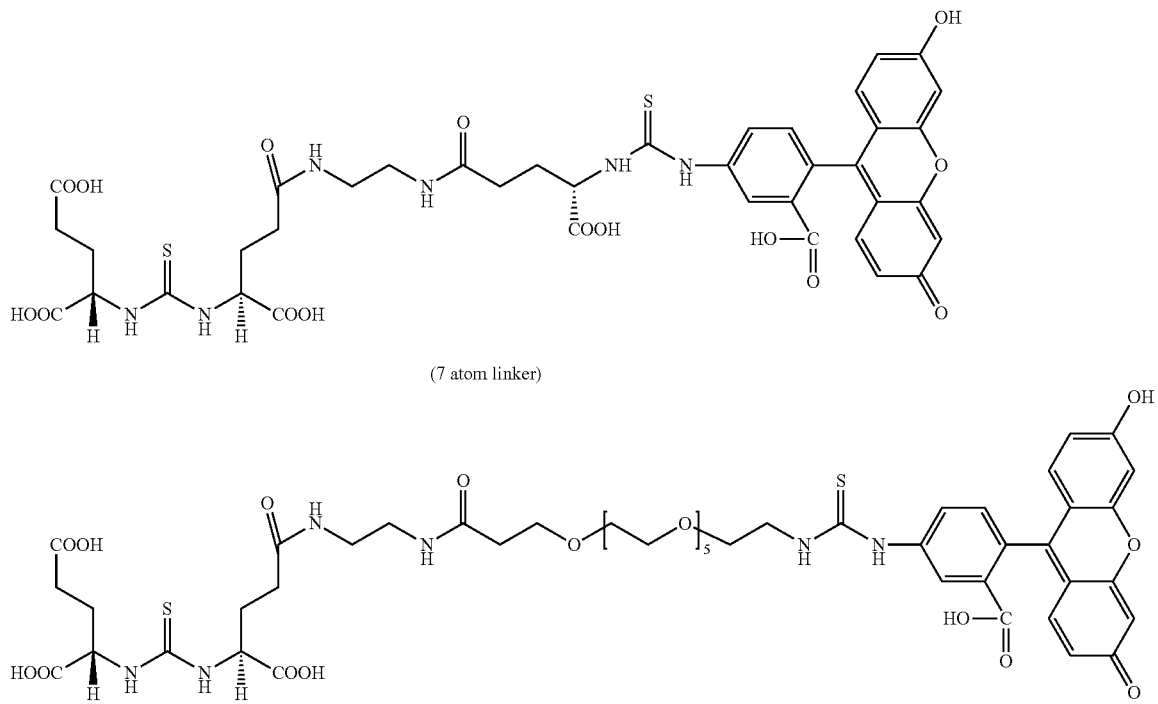
(7 atom linker)
Example
General synthesis of Cys-maleimide PSMA imaging agent conjugates using Wang PSMA (DUPA) resin, illustrated with a 28-atom linker, and Oregon Green 488, where n=3, and where B is a PSMA binding ligand as described herein.
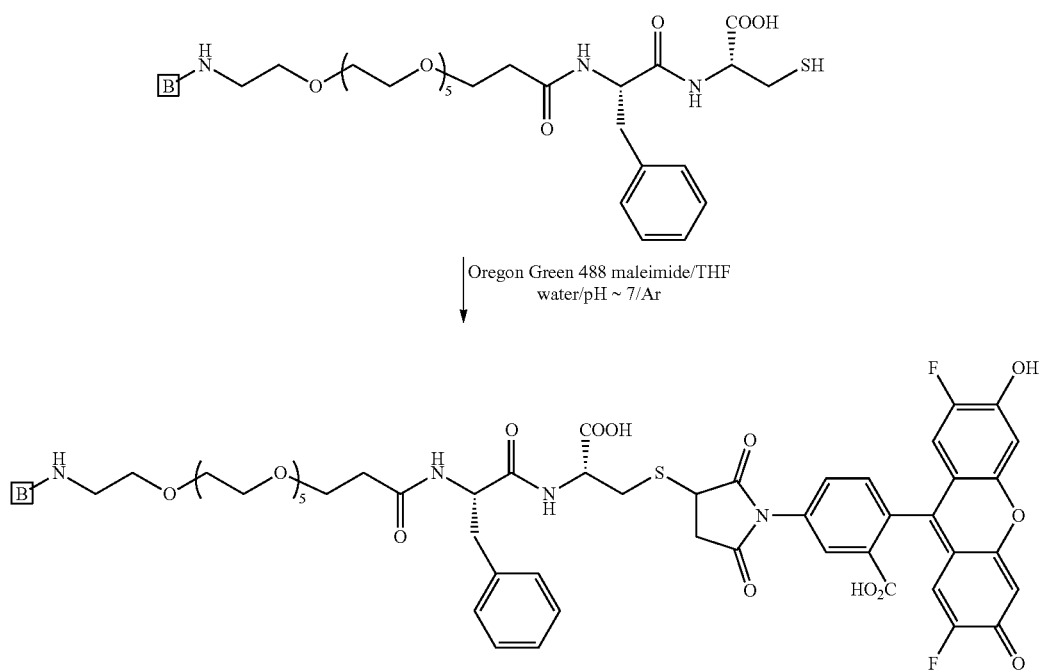

Related analogs where n is an integer from 4 to about 30 may also be prepared according to the processes described herein.

24 atom linker. HPLC grade Milli-Q water and satd NaHCO$_3$ are purged with argon for 10 min. The starting compounds is dissolved in 1.0 mL of argon purged water while bubbling argon. The pH of the solution is increased up to 6.8 and oregon green 488 maleimide dissolved in 1.0 mL of THF is added to the reaction mixture. The reaction is monitored by analytical HPLC (10 mM NH$_4$OAc, pH=7.0; 1% B to 50% B in 10 min 80% B wash 15 min run) and reaction is completed within 10 min. THF is evaporated and reaction mixture is diluted with 5.0 mL of 7 mM phosphate buffer. Purification is performed using reverse phase preparative HPLC (Waters, xTerra C$_{18}$ 10 μm; 19×250 mm) A=7 mM Phosphate buffer pH=7.2, B=ACN; λ=488 nm; Solvent gradient: 1% B to 50% B in 25 min, 80% B wash 40 min run, (89%); and analyzed using reverse phase analytical HPLC (Waters, X-Bridge C$_{18}$ 5 μm; 3.0×150 mm); A=10 mM NH$_4$OAc, B=ACN; λ=488 nm, 1% B to 50% B in 10 min, 80% B wash 15 min run.

The following 24-atom linker compounds are prepared in an analogous manner to those described herein using the General syntheses described herein.

Example

The following AlexaFluor 488 conjugate compound is prepared according to the processes described herein, where n=3, and where B is a PSMA binding ligand as described herein.

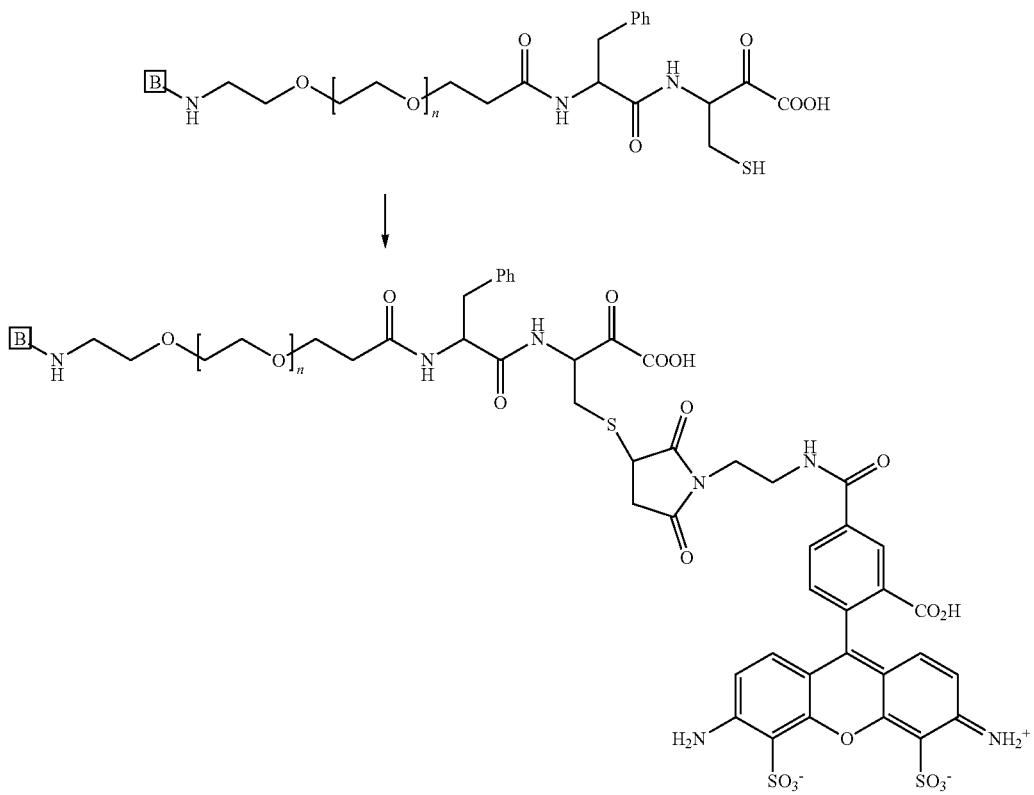

The following compounds where n is an integer from 4 to about 30 may also be prepared according to the processes described herein, including where n is 5:

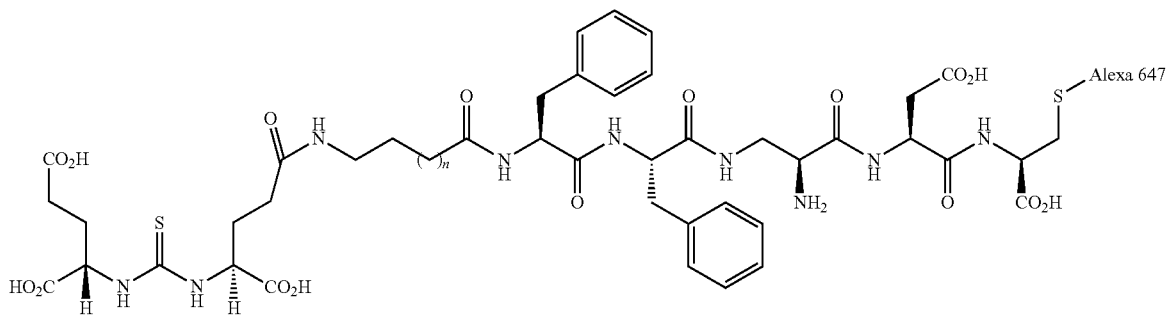

25-atom linker with AlexaFluor 647, MW ~2300 (commercially available from Invitrogen)

The following compounds where n is an integer from 0 to about 12 may also be prepared according to the processes described herein.

Linker is dissolved in 1.0 mL of argon purged while bubbling argon. The pH of the solution is increased to 6.8 and AlexaFluor maleimide, BODIPY maleimide, or Oregon green 488 maleimide, respectively, is dissolved in 1.0 mL of tetrahydrofuran (THF) is added to the reaction mixture.

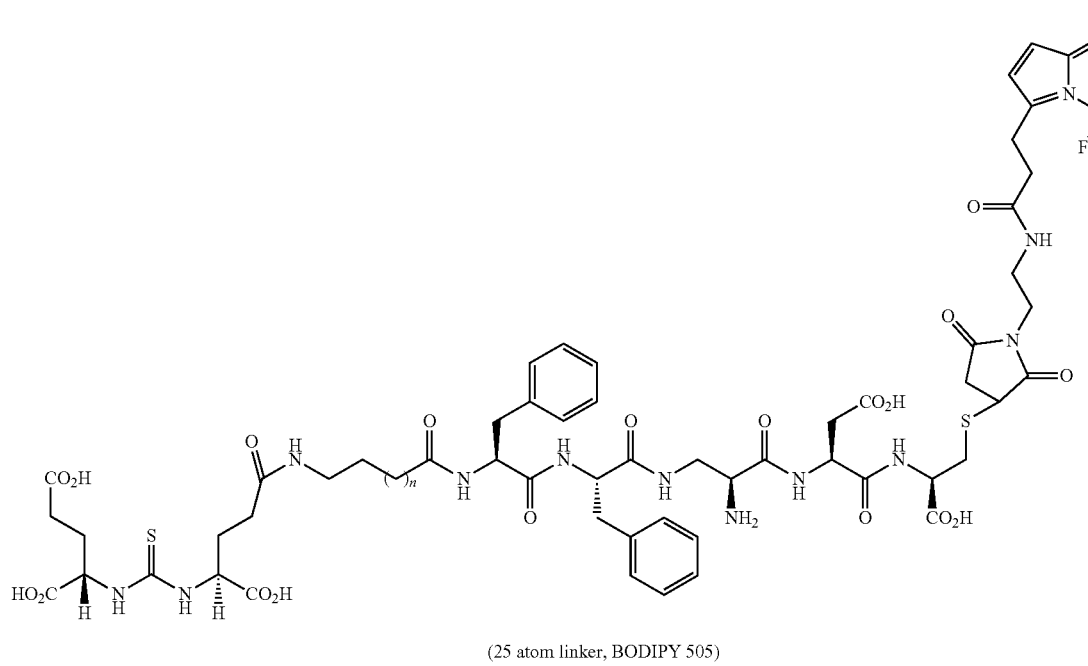

(25 atom linker, BODIPY 505)

The following compounds where n is an integer from 0 to about 12 may also be prepared according to the processes described herein.

Progress of the reaction is monitored by analytical HPLC (10 mM NH$_4$OAc, pH=7.0; 1% B to 50% B in 10 min 80% B wash 15 min run) and reaction is completed within 10

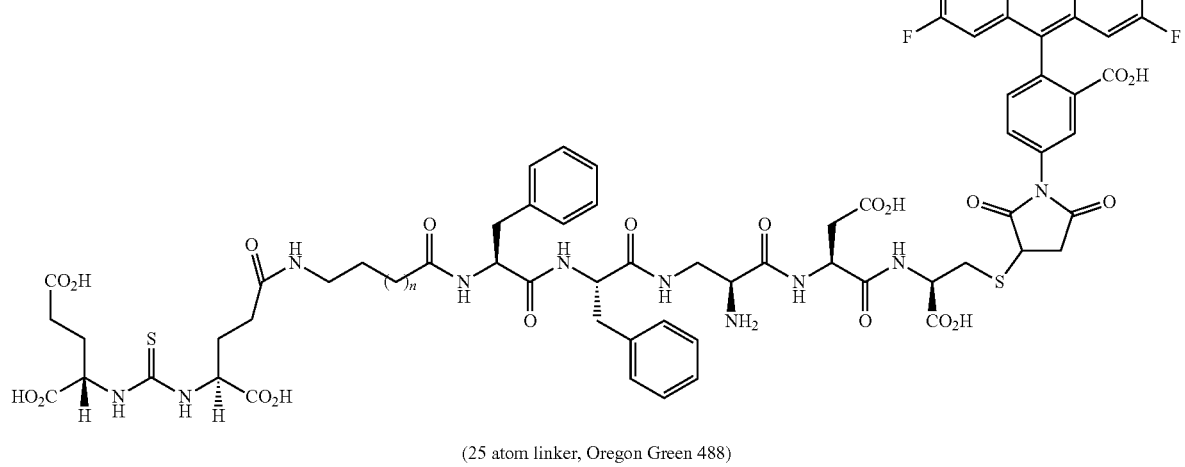

(25 atom linker, Oregon Green 488)

Synthesis of the Linker. In each of the foregoing Examples, the linker is synthesized using standard Fmoc SPPS starting from Fmoc-Cys(Trt)-Wang resin (Novabiochem; Catalog #04-12-2050).

Synthesis of AlexaFluor 647 conjugate, BODIPY conjugate and Oregon Green 488 conjugate. HPLC grade Milli-Q water and satd NaHCO$_3$ is purged with argon for 10 min.

mM. THF is evaporated and reaction mixture is diluted with 5.0 mL of 1 mM phosphate buffer (pH=7.2).

Compounds are purified using reverse phase preparative HPLC (Waters, xTerra C$_{18}$ 5 μm; 18×150 mm) A=1 mM Phosphate buffer pH=7.2, B=ACN; λ=647 or 488 nm; Solvent gradient: 1% B to 50% B in 25 min, 80% B wash 40 min run; and analyzed using reverse phase analytical HPLC (Waters, X-Bridge $C_{18}$ 5 μm; 3.0×50 mm); A=10 mM $NH_4OAc$, B=ACN; λ=588 or 488 nm, 1% B to 50% B in 10 min, 80% B wash 15 min run.
Example 5
General synthesis of PSMA disulfide linker intermediates for releasable linker conjugates, where B is a PSMA binding ligand as described herein.
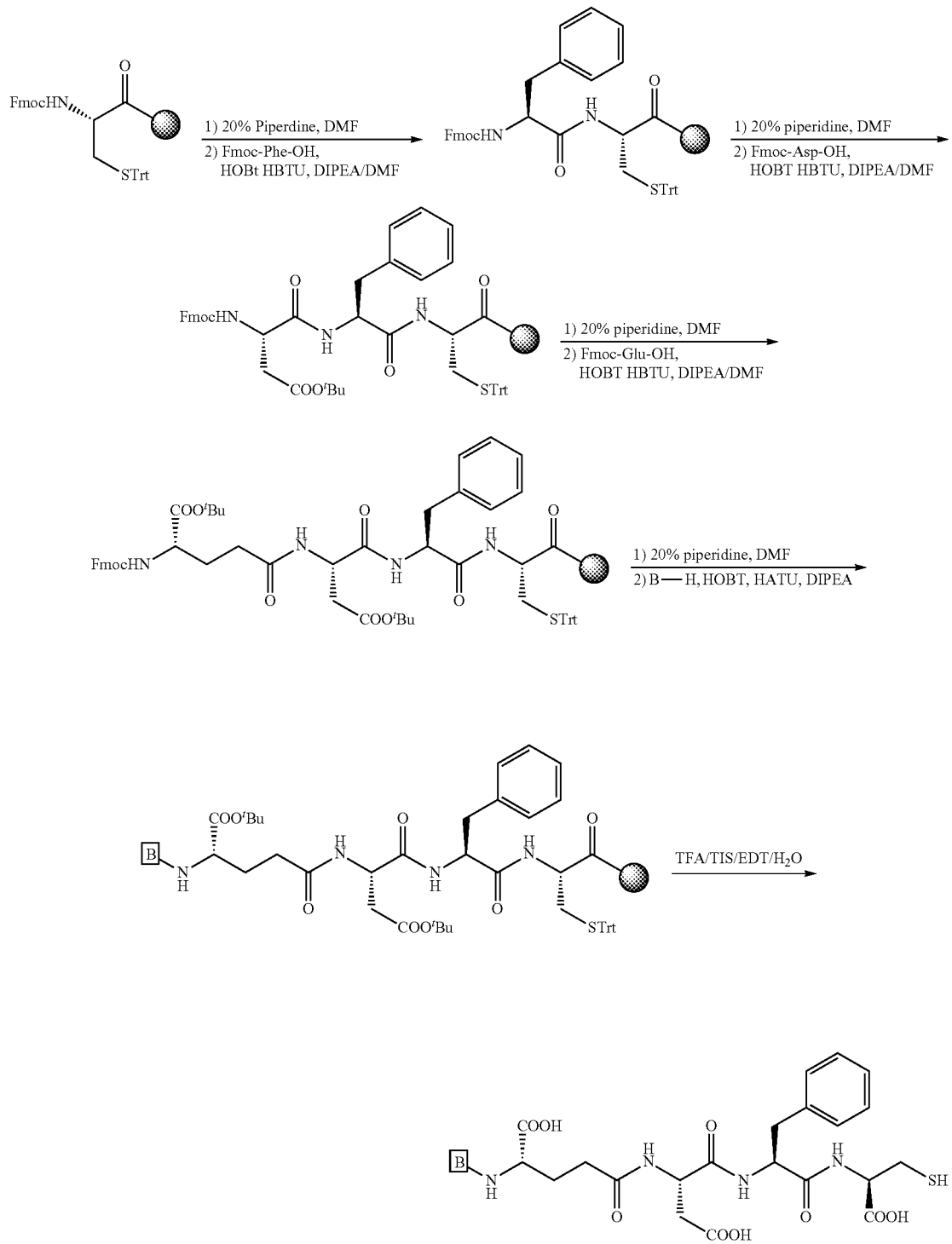

Intermediates are synthesized using standard Fmoc SPPS starting from Fmoc-Cys(Trt)-Wang resin (Novabiochem; Catalog #04-12-2050), purified using reverse phase preparative HPLC (Waters, xTerra C$_{18}$ 10 μm; 19×250 mm) A=0.1 TFA, B=ACN; λ=257 nm; Solvent gradient: 1% B to 50% B in 30 min, 80% B wash 40 min run, (68%); and analyzed using reverse phase analytical HPLC (Waters, X-Bridge C$_{18}$ 5 μm; 3.0×15 mm); A=0.1 TFA, B=ACN; λ=257 nm, 1% B to 50% B in 10 min, 80% B wash 15 min run.

Example

General synthesis of PSMA disulfide linker intermediate for releasable agent conjugate, where B is a PSMA binding ligand as described herein.

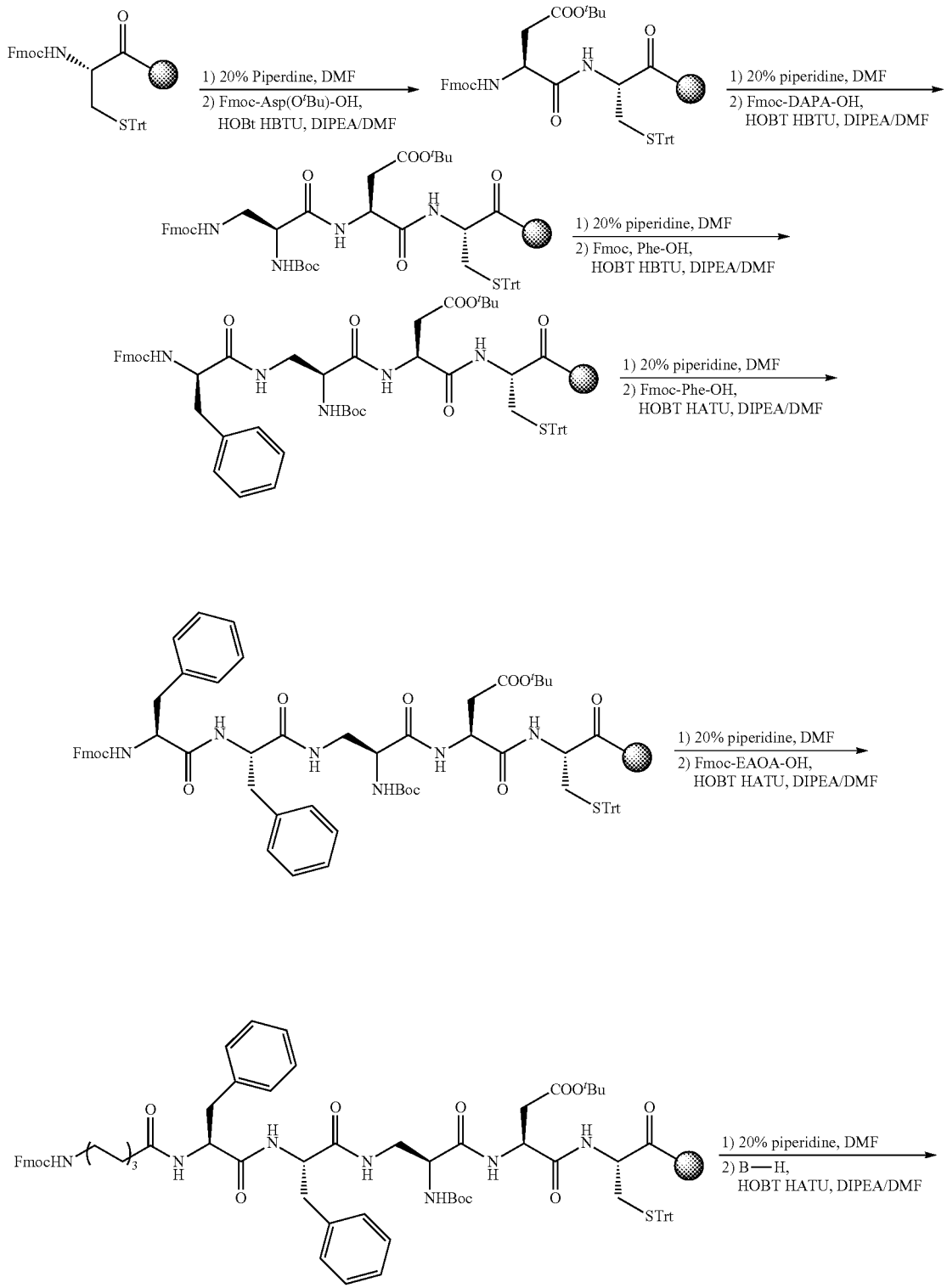

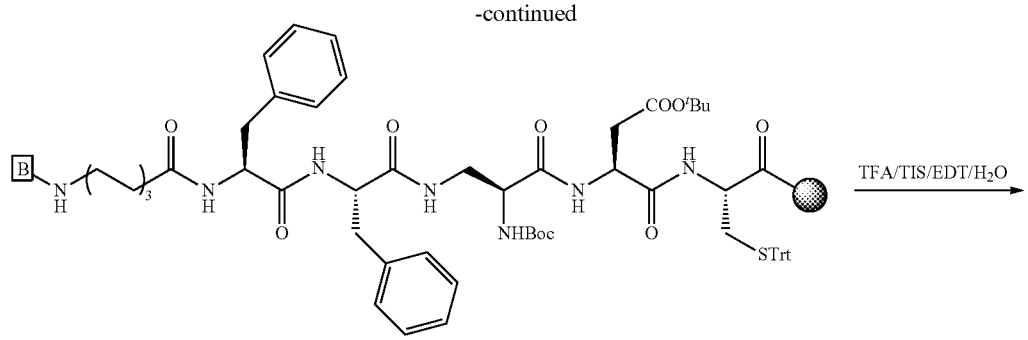

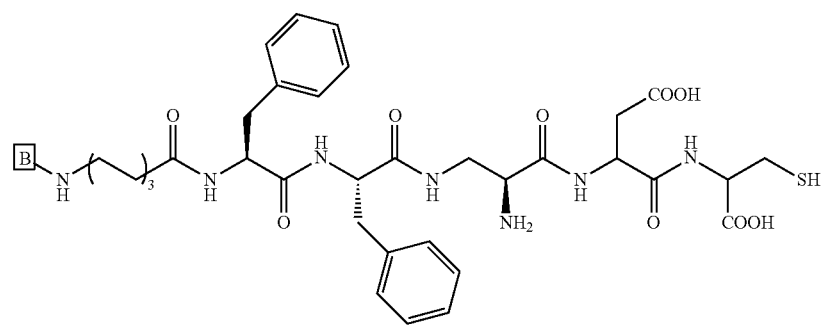

was synthesized using standard Fmoc-SPPS starting from Fmoc-Cys(Trt)-Wang resin (Novabiochem; Catalog #04-12-2050); purified using reverse phase preparative HPLC (Waters, xTerra $C_{18}$ 10 μm; 19×250 mm) A=0.1 TFA, B=ACN; λ=257 nm; Solvent gradient: 5% B to 80% B in 25 min, 80% B wash 30 min run, (61%); and analyzed using reverse phase analytical HPLC (Waters, X-Bridge $C_{18}$ 5 μm; 3.0×15 mm);

A=0.1 TFA, B=ACN; λ=257 nm, 5% B to 80% B in 10 min, 80% B wash 15 min run.

Example

General synthesis for preparing disulfide-linked conjugates, illustrated for tubulysin B conjugate and 20-atom linker, where B is a PSMA binding ligand as described herein.

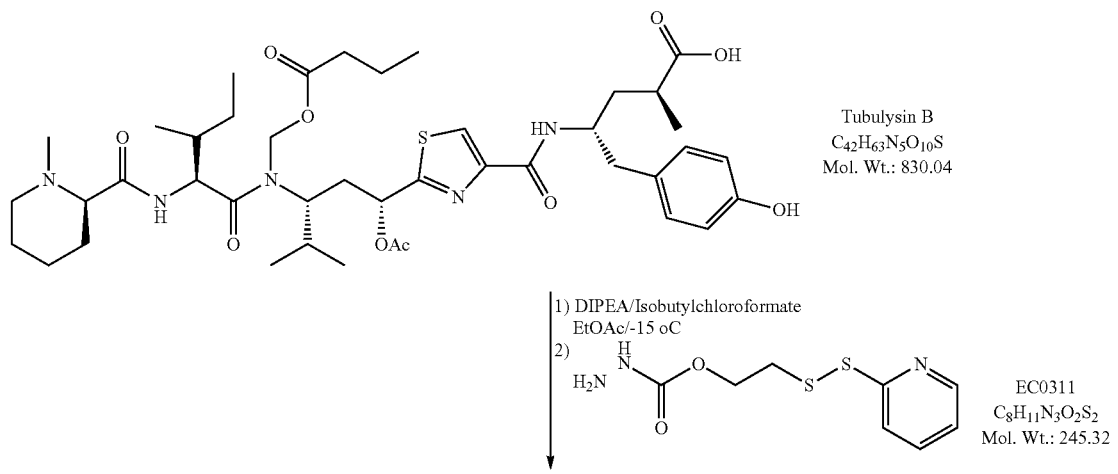

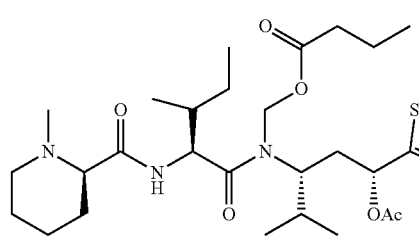
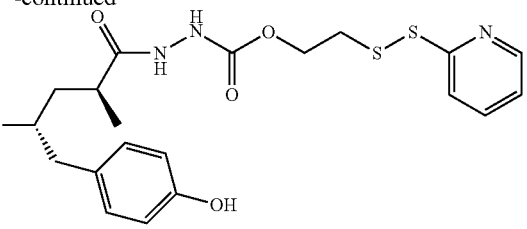

-continued

EC0312
C₅₀H₇₂N₈O₁₁S₃
Mol. Wt.:
1057.35

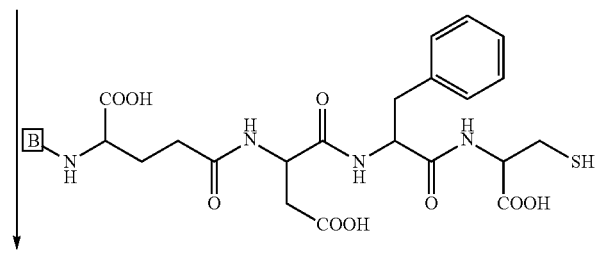

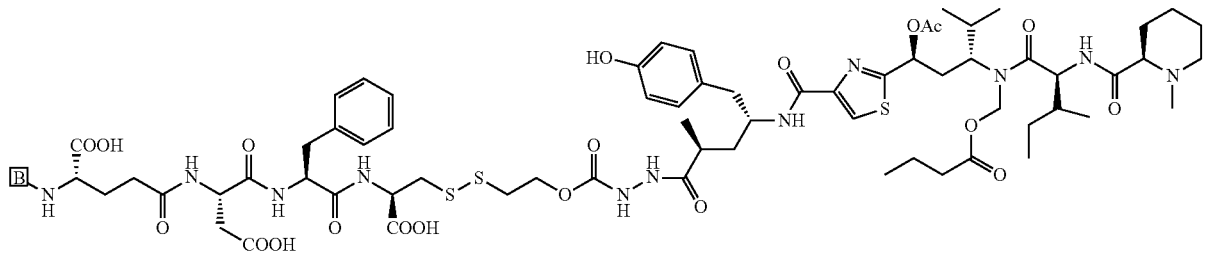

Tubulysin B (30 mg, 0.036 mmol) is dissolved in ethylacetate (600 μL) under argon at −15° C. Isobutyl chloroformate (4.7 μL, 0.054 mmol) and diisopropylethylamine (13.2 μL, 0.076 mmol) are added to the reaction mixture; reaction was stirred at −15° C. for 45 min under argon. EC0311 (13.4 mg, 0.054 mmol) dissolved in ethylacetate (500 μL) is added. Reaction mixture is stirred at −15° C. for another 15 min and then at room temperature for 45 min. Solvent is evaporated and residue is purified using short column (2%-8% methanol in CH₂Cl₂) to get EC0312 (34.4 mg, 90.5%). EC0312 is characterized using NMR (Varian 300 MHz, in CDCl₃), and LC-MS=1058.3 (M+H)⁺.

HPLC grade Milli-Q water and satd NaHCO₃ is purged with argon for 10 Intermediate binding ligand thiol is dissolved in 1.0 mL of argon purged water while bubbling argon through the solution. The pH of the solution is increased to 6.8 using argon purged NaHCO₃ and EC0312 dissolved in THF (2.0 mL) is added to the reaction mixture. Progress of the reaction is monitored by analytical HPLC (10 mM NH₄OAc, pH=7.0; λ=254; 1% B to 50% B in 10 min 80% B wash 15 min run) and reaction is completed within 10 min. THF is evaporated and reaction mixture is diluted with 5.0 mL of 2 mM phosphate buffer. Final compounds are purified using reverse phase preparative HPLC (Waters, xTerra C₁₈ 10 μm; 19×250 mm) A=2 mM Phosphate buffer, B=ACN; λ=254 nm; 5% B to 80% B in 25 min 80% B wash 40 min run; and analyzed using reverse phase analytical HPLC (Waters, X-Bridge C₁₈ 5 μm; 3.0×15 mm); A=10 mM NH₄OAc, B=ACN; λ=254 nm, 1% B to 50% B in 10 min, 80% B wash 15 min run.

The following additional examples may be prepared according to the procedures described herein.

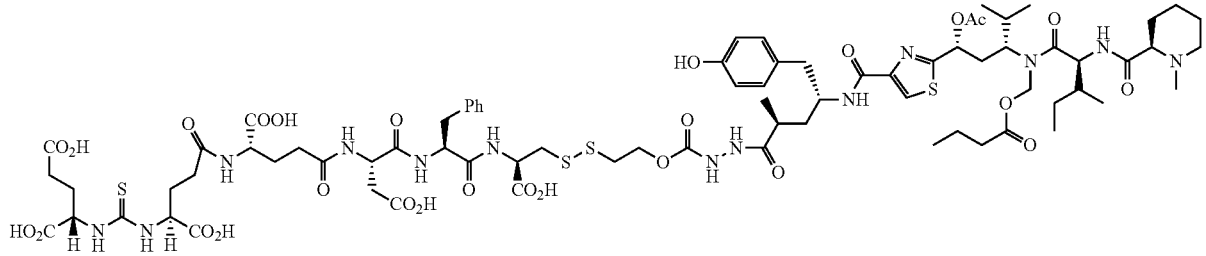

(20 atom linker, Tubulysin)

-continued
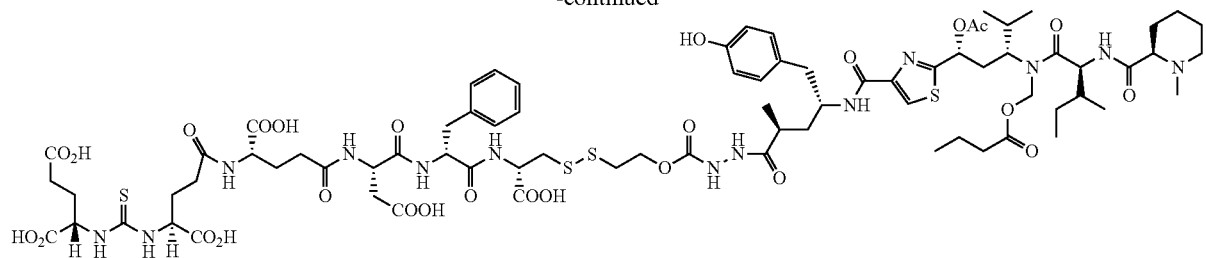
(20 atom linker, Tubulysin)
Example 15
General synthesis for preparing disulfide-linked conjugates, illustrated for tubulysin B conjugate with 31-atom linker, where B is a PSMA binding ligand as described herein.

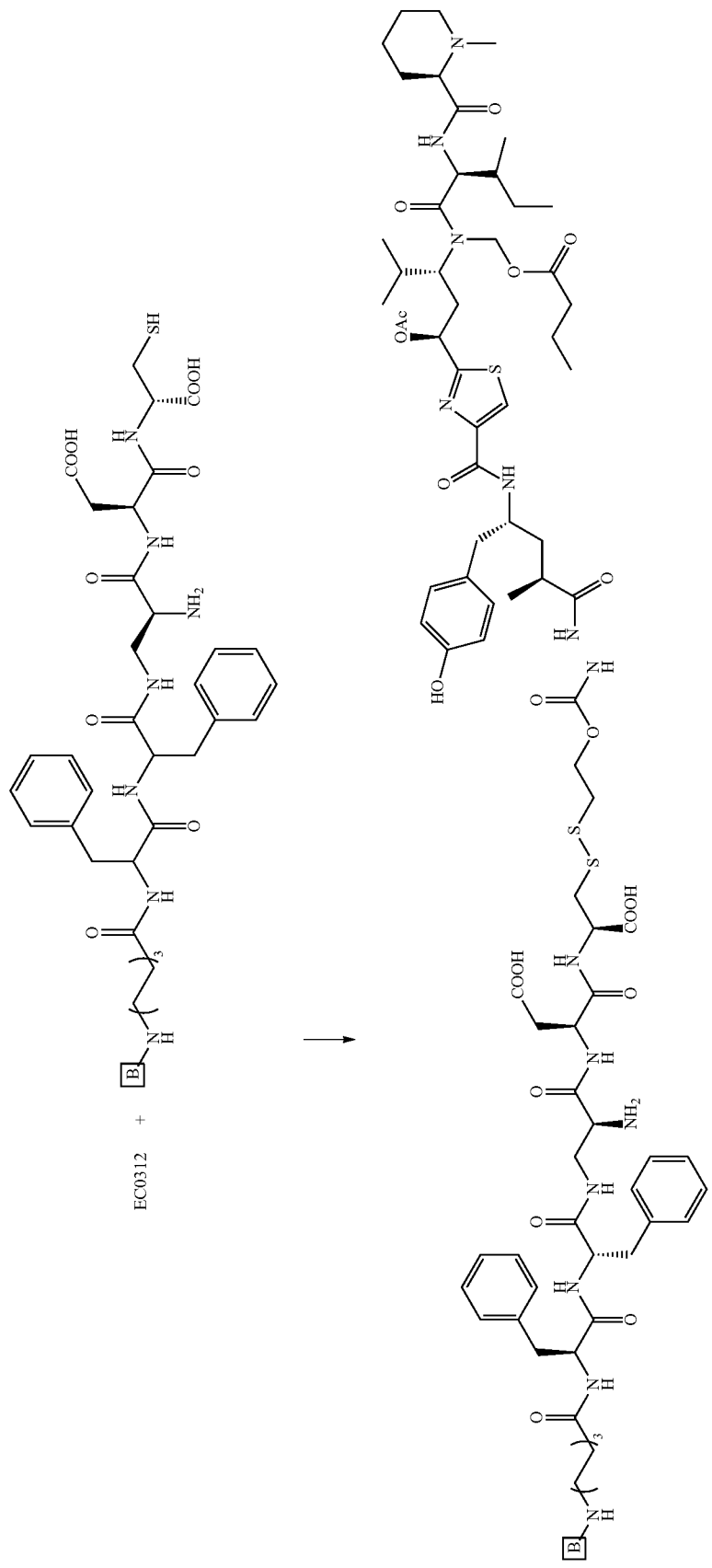

HPLC grade Milli-Q water and satd $NaHCO_3$ are purged with argon for 10 min. Intermediate binding ligand thiol is dissolved in 1.0 mL of argon purged water while bubbling argon. The pH of the solution is increased to 6.8 using argon purged $NaHCO_3$ and EC0312 dissolved in THF (2.0 mL) is added to the reaction mixture. Progress of the reaction is monitored by analytical HPLC (10 mM $NH_4OAc$, pH=7.0; $\lambda$=254; 1% B to 50% B in 10 min 80% B wash 15 min run) and reaction was completed within 10 min. THF is evaporated and reaction mixture is diluted with 5.0 mL of 2 mM phosphate buffer. SK77 (61%) was purified using reverse phase preparative HPLC (Waters, xTerra $C_{18}$ 10 μm; 19×250 mm) A=2 mM phosphate buffer, B=ACN; $\lambda$=254 nm; 5% B to 80% B in 25 min 80% B wash 40 min run; and analyzed using reverse phase analytical HPLC (Waters, X-Bridge $C_{18}$ 5 μm; 3.0×15 mm); A=10 mM $NH_4OAc$, B=ACN; $\lambda$=254 nm, 1% B to 50% B in 10 min, 80% B wash 15 min run.

The following additional examples may be prepared according to the procedures described herein.

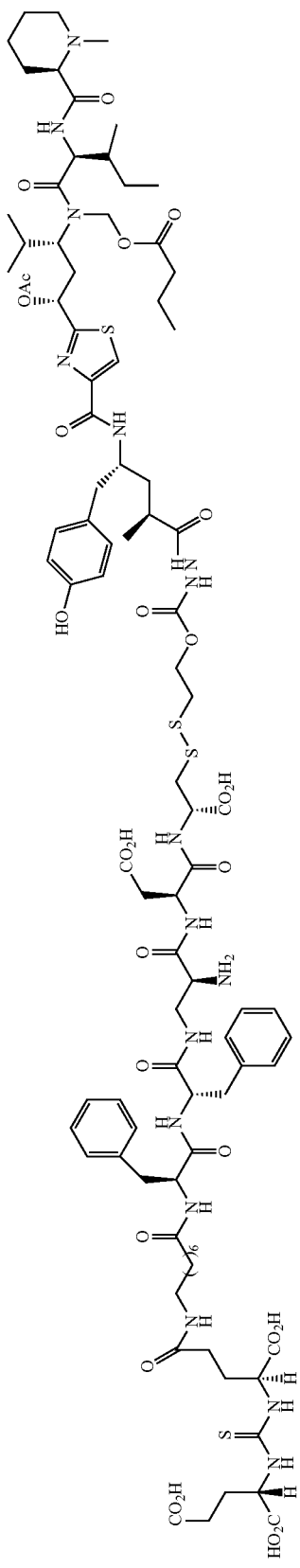
(31 atom linker, Tubulysin)
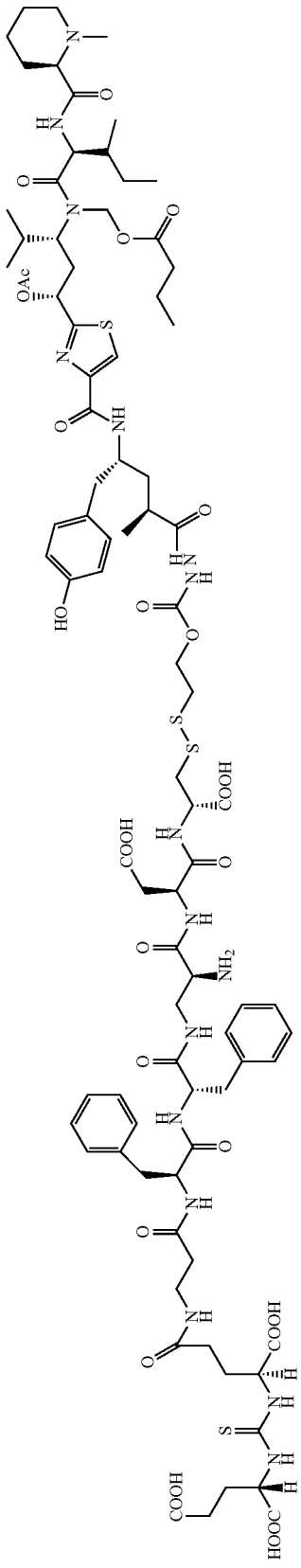
(26 atom linker, Tubulysin)

-continued
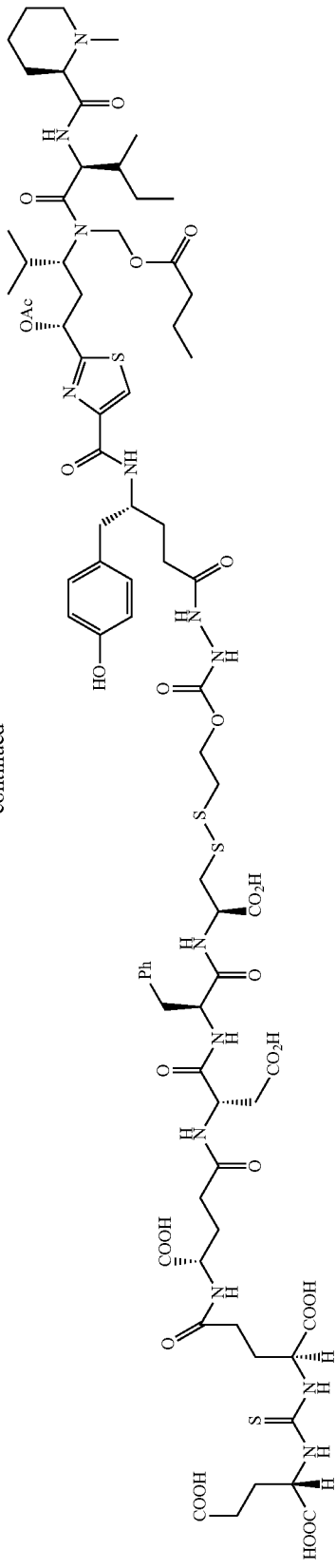
(20 atom linker, Tubulysin)
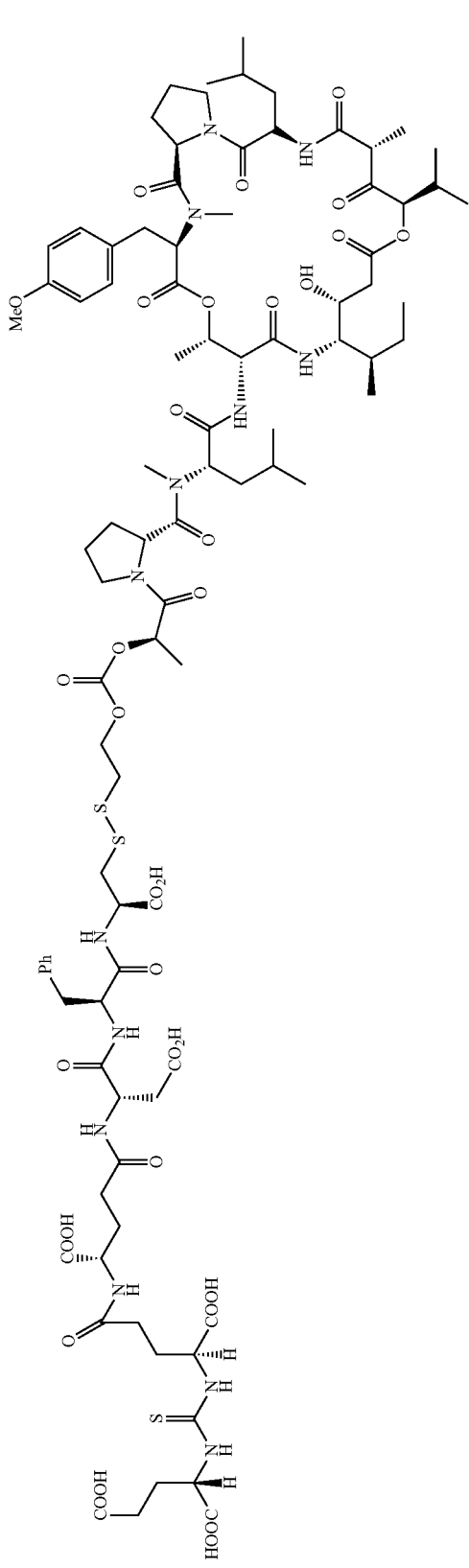
(20 atom linker, Didemnin B)

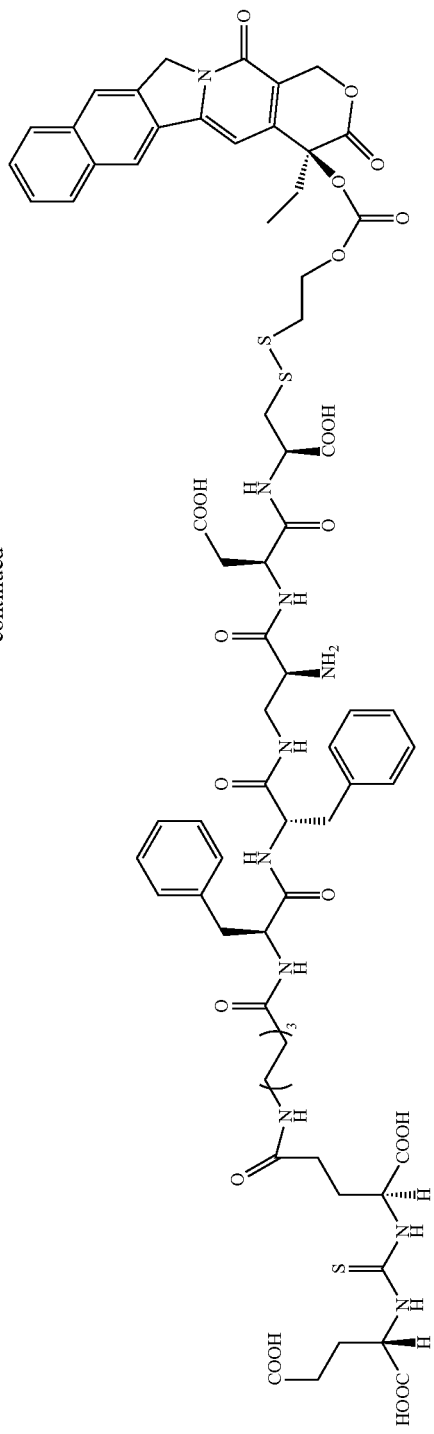
(30 atom linker, Camptothecin)
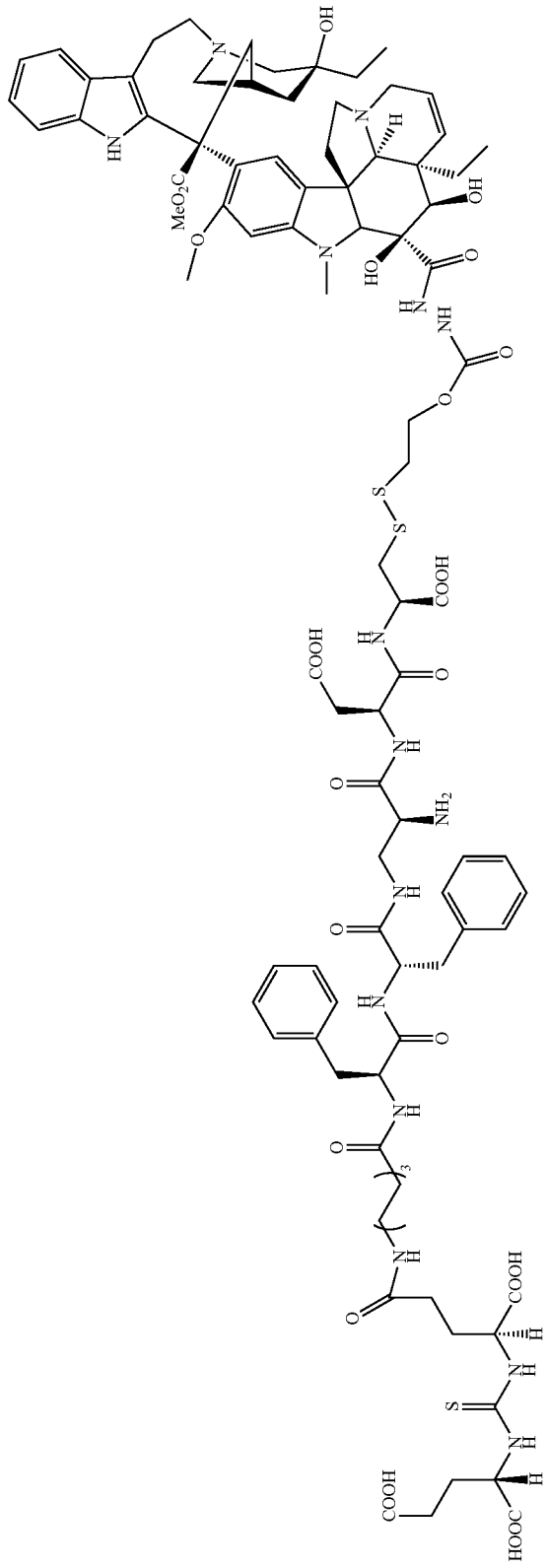
(30 atom linker, Desacetylvinblastinhydrazide)

-continued
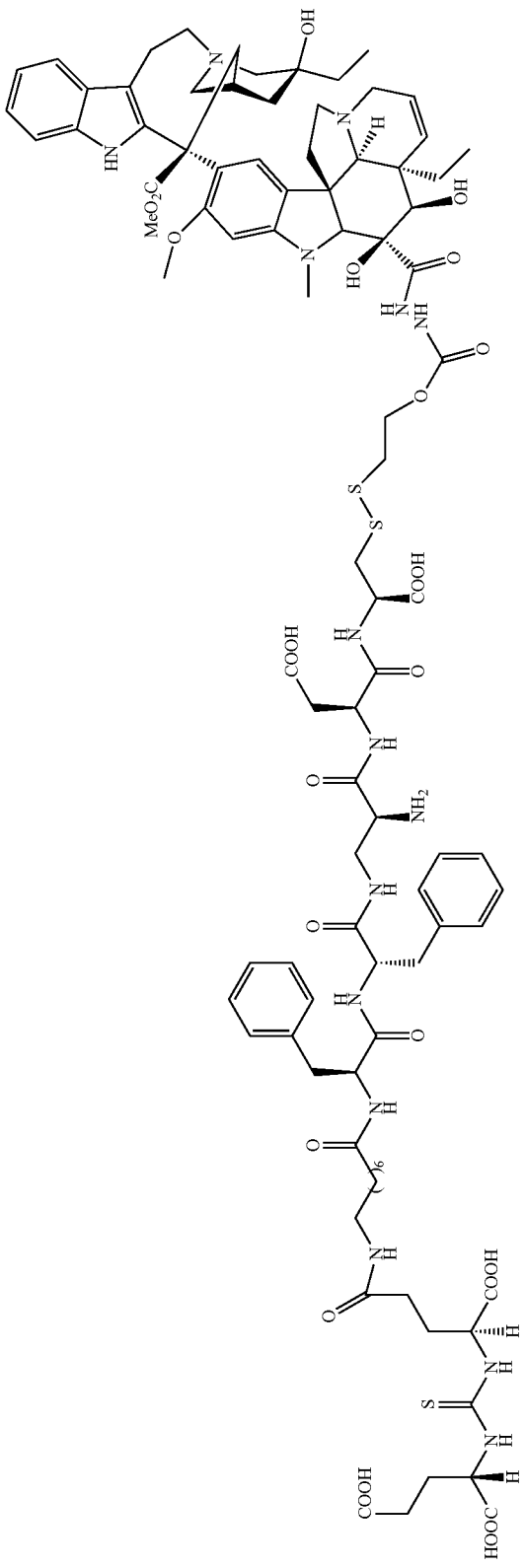
(31 atom linker, Desacetylvinblastinhydrazide)
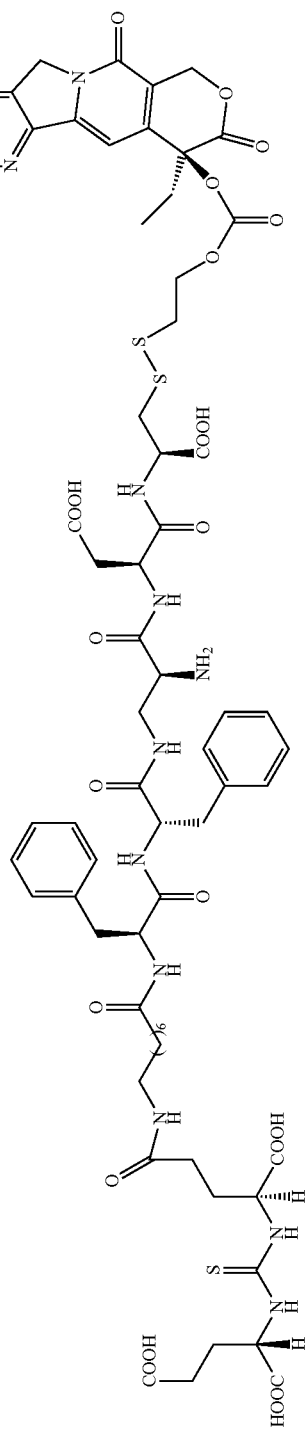
(31 atom linker, Camptothecin)

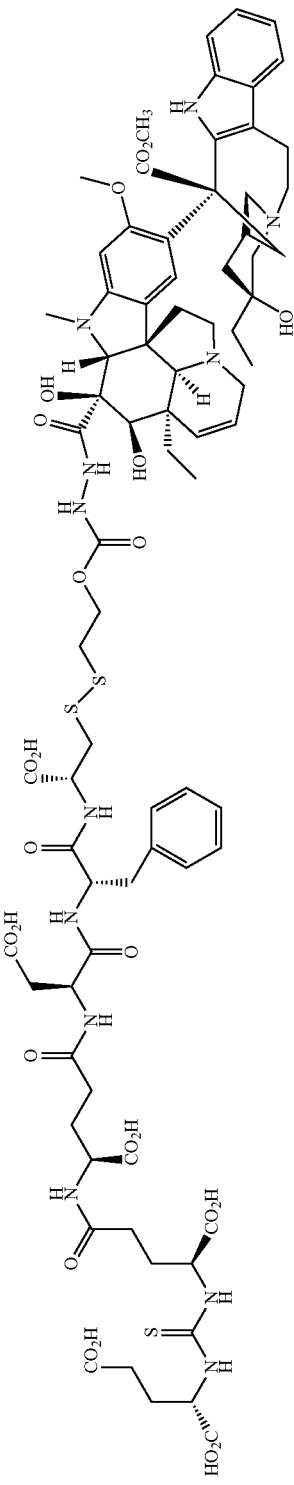
(20 atom linker, Desacetylvinblastinhydrazide)
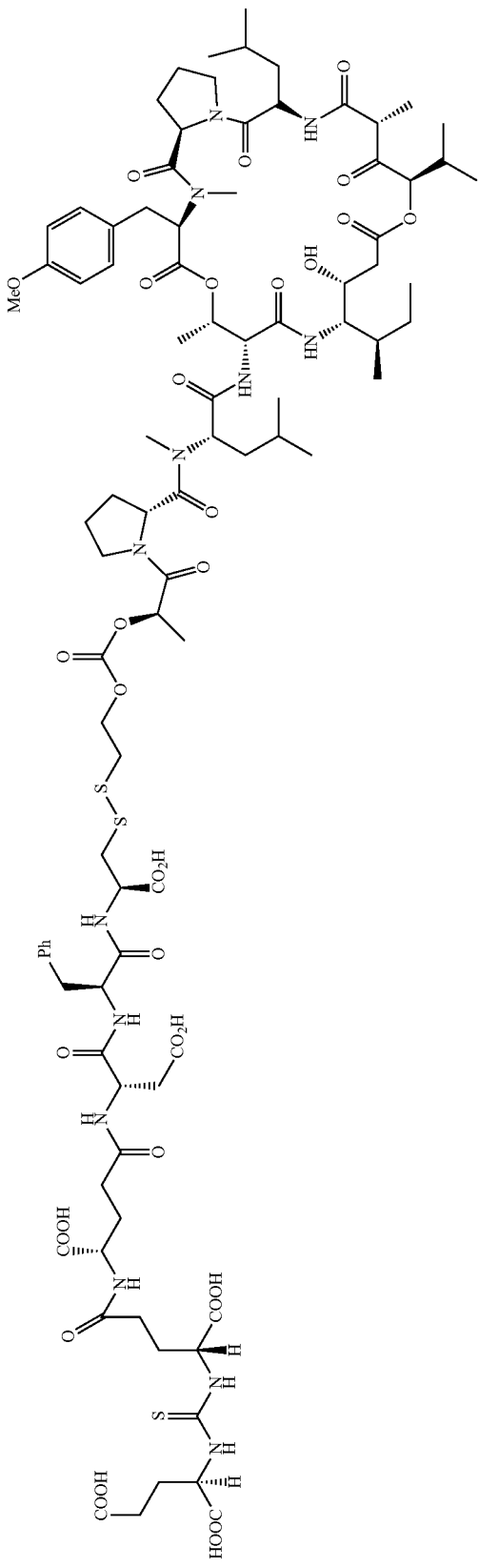
(20 atom linker, Didemnin B)

The following additional examples are described herein.

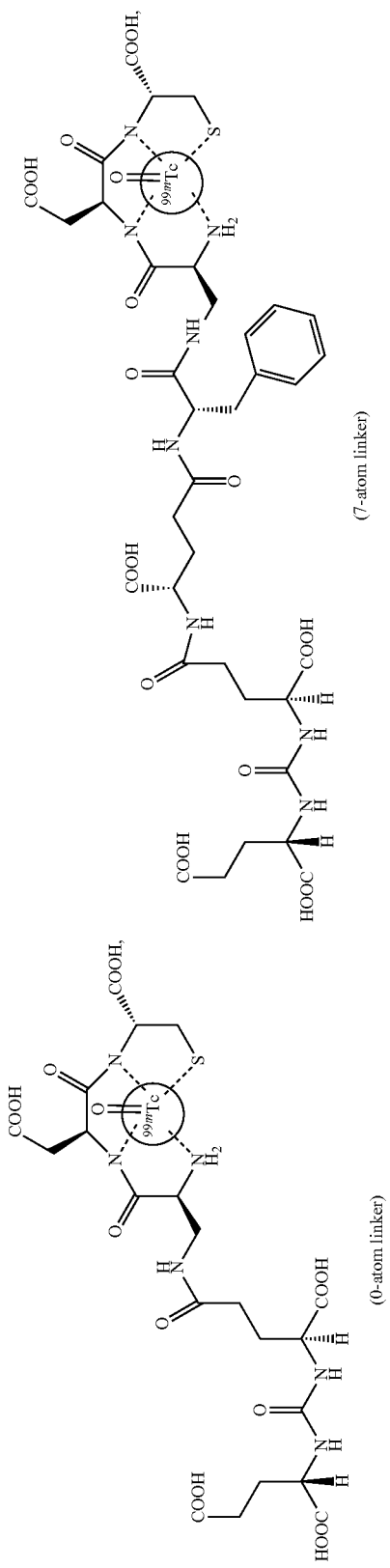
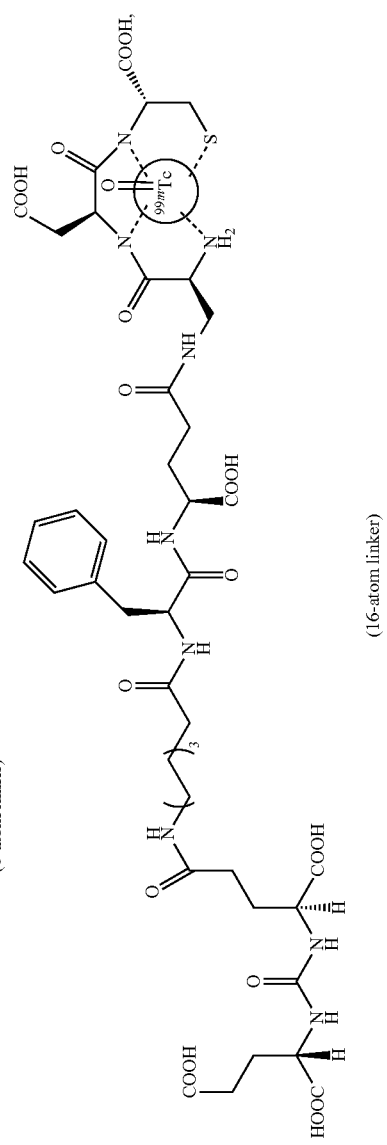

-continued
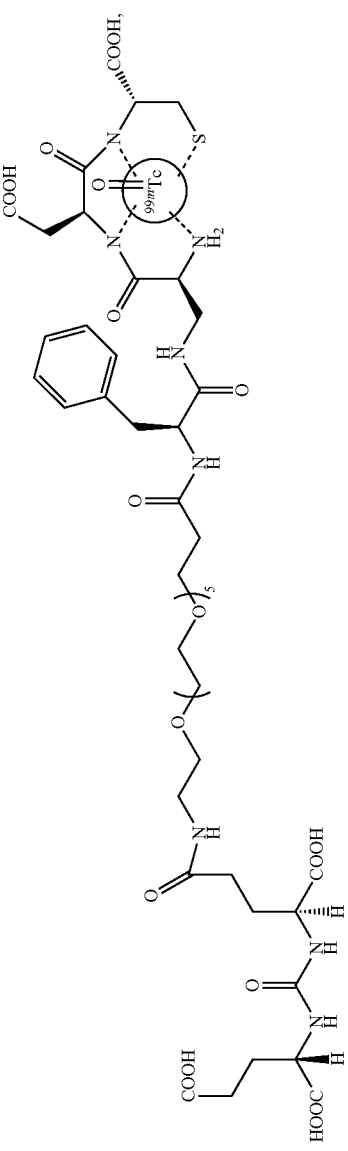
(24-atom linker)
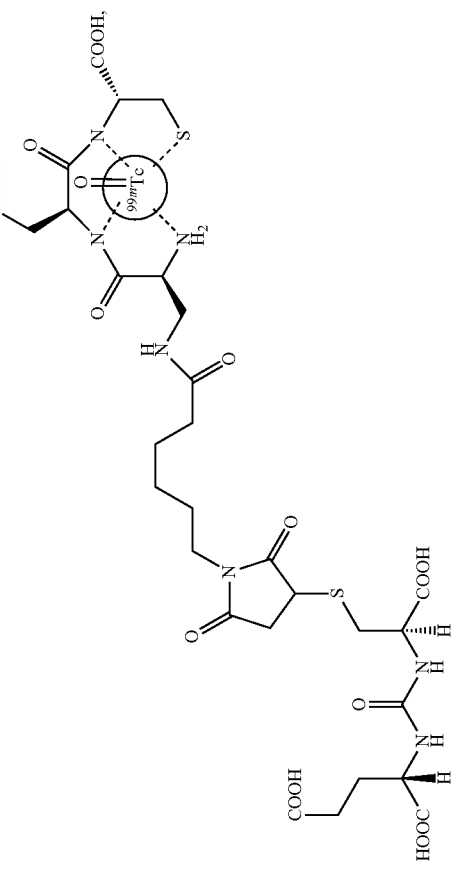
(9-atom linker)

-continued
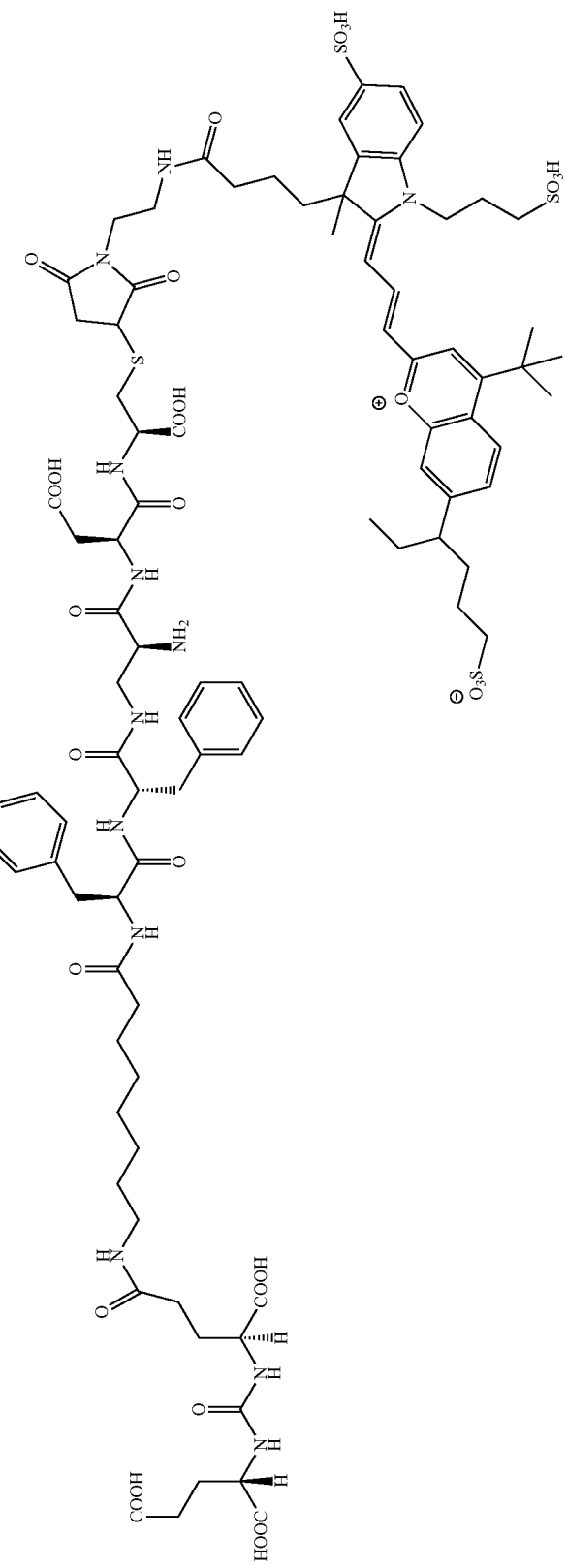
(31 atom linker, Dylight 680)
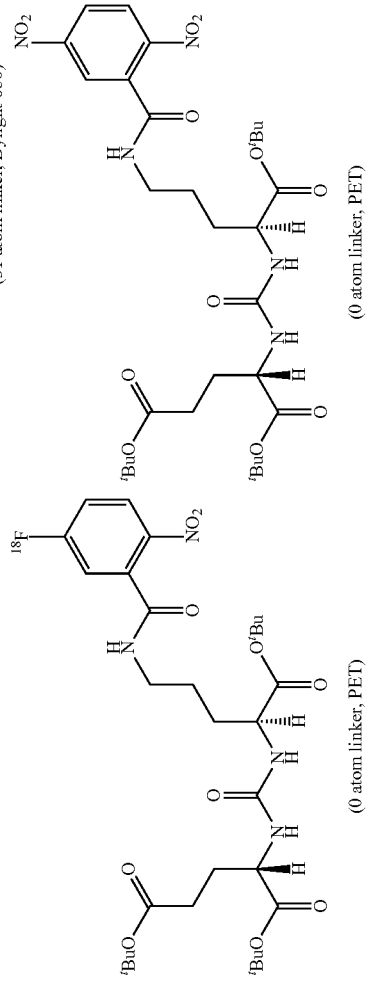
(0 atom linker, PET)
(0 atom linker, PET)

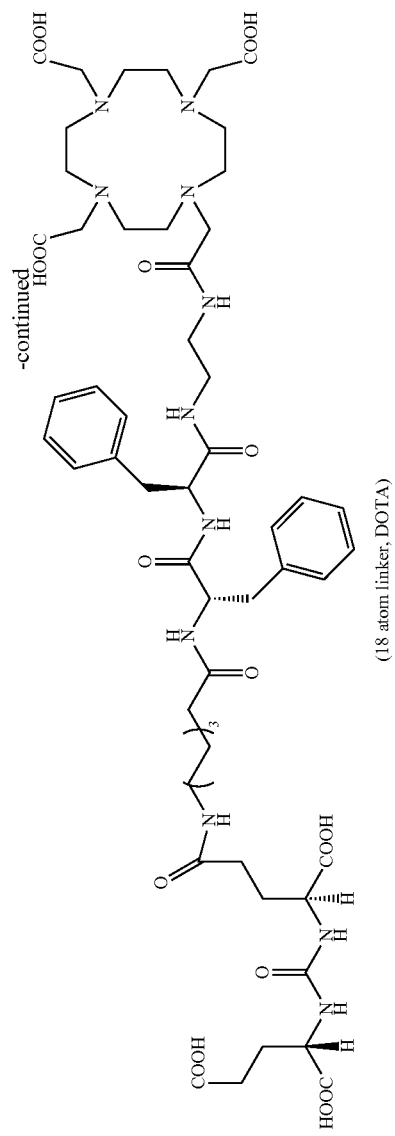
(18 atom linker, DOTA)
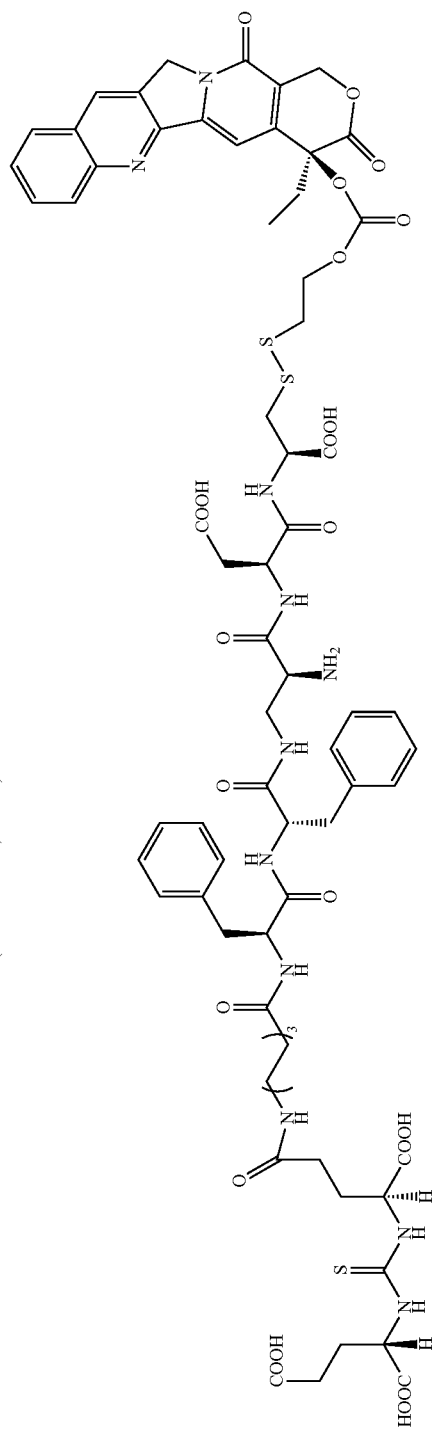
(30 atom linker, Camptothecin)

-continued
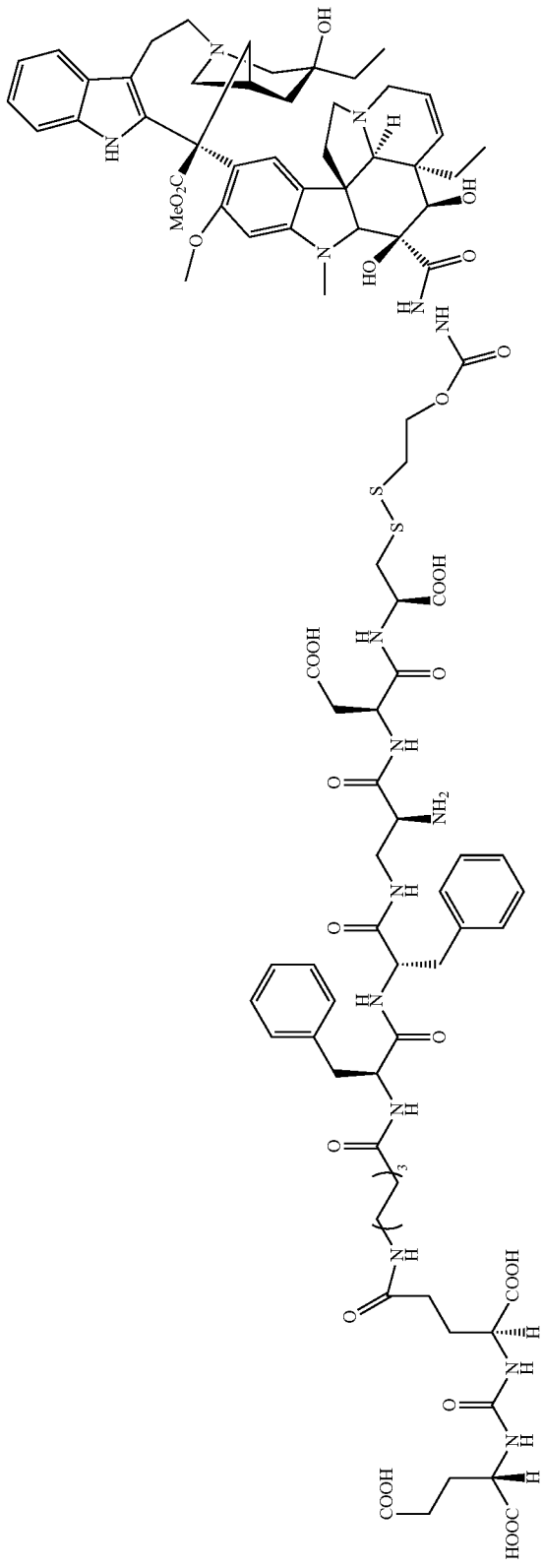
(30 atom linker; Desacetylvinblastinhydrazide)
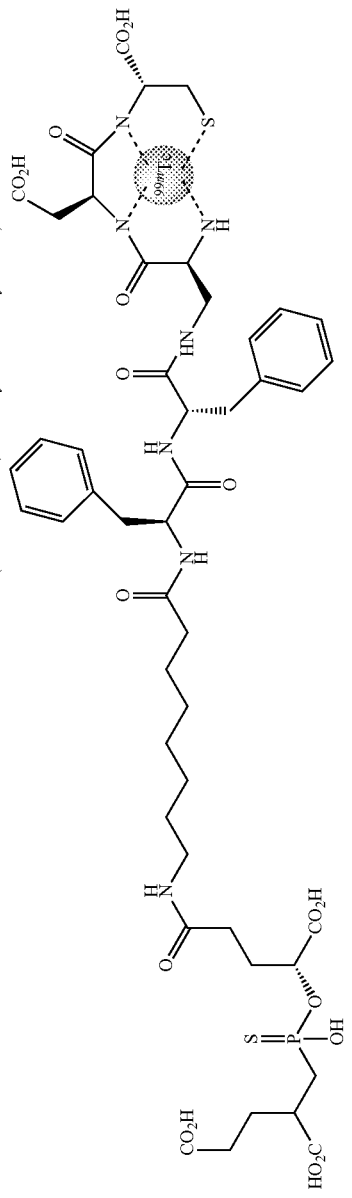
(15 atom linker)

The foregoing exemplary embodiments are intended to be illustrative of the invention, and should not be interpreted or construed as limiting in any way the invention as described herein.

METHOD EXAMPLES

Example

In Vitro Binding Studies Using LNCaP Cells. This assay is described in PCT International Publication No. WO 2009/026177, the disclosure of which is incorporated herein by reference. Briefly, 22RV1 cells or LNCaP cells (human prostate cancer cell lines over-expressing PSMA) are seeded in two 24-well (e.g. 120,000 cells/well) falcon plates and allowed to grow to adherent monolayers for 48 hours in RPMI with glutamine (2 mM)(Gibco RPMI medium 1640, catalog #22400) plus 10% FBS (Fetal Bovine Serum), 1% sodium pyruvate (100 mM) and 1% PS (penicillin streptomycin) in a 5%-CO2 atmosphere at 37° C. Cells of one 24-well plate are incubated with increasing concentrations of SK28-99mTc from 0 nM-450 nM (triplicates for each concentration) in a 5%-CO2 atmosphere at 37° C. for 1 hour. Cells of the second 24-well plate are incubated with 50 uM PMPA in a 5%-CO2 atmosphere at 37° C. for 30 minutes, then incubated with increasing concentrations of SK28-99mTc from 0 nM-450 nM (triplicates for each concentration) in a 5%-CO2 atmosphere at 37° C. for 1 hour (competition study). Cells are rinsed three times with 1.0 mL of RPMI. Cells are lysed with tris-buffer, transferred to individual gamma scintigraphy vials, and radioactivity is counted. The plot of cell bound radioactivity verses concentration of radiolabeled compound is used to calculate the Kd value. The competition study is used to determine the binding specificity of the test compound to PSMA.

Compounds described herein bind with high affinity and specificity to the 22RV1 cells and LNCaP cells. For example, $^{99m}$Tc chelating conjugate compound VC6 exhibits a Kd of 162 nM in 22RV1 cells, and 164 nM in LNCaP cells. In each case, the binding affinity of VC6 is significantly lower in the presence of PMPA, indicating that the binding is specific to PSMA.

Example

In Vivo Growth of Human LNCaP Tumor Cells in Nude Mice. This assay is described in PCT International Publication No. WO 2009/026177. Briefly, LNCaP cells are maintained in RPMI 1640 (Gibco RPMI medium 1640, catalog #22400) with glutamine (2 mM), 10% FBS (Fetal Bovine Serum), 1% sodium pyruvate (100 mM) and 1% PS (penicillin streptomycin) in a 5%-CO2 atmosphere at 37° C. Four to five week-old athymic male nude mice (nu/nu) are obtained from the NCI Charles River. Matrigel and high concentrated (HC) matrigel are purchased from BD Biosciences. Nude mice are inoculated with either 2.5×106 or 5.0×10 6 in vitro propagated LNCaP cells in 50% matrigel (100 uL RPMI medium+100 uL of matrigel) or 50% high concentrated matrigel (100 uL RPMI medium+100 uL of HC matrigel) to determine optimal conditions. Cells are subcutaneously injected into each axial and each flank of the nude mice to determine the optimal site. The volume of each tumor is measured in perpendicular directions twice a week using a caliper and body weight is measured once a week.

The volume of each tumor is calculated as 0.5×L×W2, where L=measurement of longest axis in millimeters and W=measurement of axis perpendicular to L in millimeters. Approximately $5.0 \times 10^6$ LNCaP cells in 50% HC matrigel on the axial generally give 600 mm$^3$ tumors within 3-4 weeks.

Compounds described herein are useful for imaging and diagnosing tumors expressing or overexpressing PSMA, where the compound includes an imaging or diagnosing agent. Compounds described herein are useful for treating tumors expressing or overexpressing PSMA, where the compound includes a cytotoxic agent.

Example

In Vivo Growth of Human 22RV1 Tumor Cells in Nude Mice. 22RV1 cells are maintained in RPMI 1640 (ATCC RPMI medium 1640, catalog #302001) with Geneticin® Selective Antibiotic (Gibco catalog #10131-035), 10% FBS (Fetal Bovine Serum), MEM Non-Essential Amino Acids Solution 10 mM (100×), (Gibco catalog #11140-050) and 1% PS (penicillin streptomycin) in a 5%-CO$_2$ atmosphere at 37° C. Four to five week-old athymic male nude mice (nu/nu) are obtained from the NCI Charles River and maintained in a sterile environment. Mice are housed in polycarbonate shoebox cages with wire top lids and maintained on a normal diet. Mice are allowed to acclimate for one week prior to inoculation of 22RV1 cells. Matrigel and high concentrated (HC) matrigel are purchased from BD Biosciences. Nude mice are inoculated with either $5.0 \times 10^6$ in vitro propagated 22RV1 cells in 50% matrigel (100 uL RPMI medium+100 uL of matrigel) or 50% high concentrated matrigel (100 uL RPMI medium+100 uL of HC matrigel) to determine optimal conditions, including number of cells, vehicle, etc. Cells are subcutaneously injected into each axial and each flank of the nude mice to determine the optimal site. The volume of each tumor is measured in perpendicular directions twice a week using a caliper and body weight was measured once a week, as described herein.

Example

Comparison of LNCaP, KB and A549 Cell Tumor Growth in Mice. This assay is described in PCT International Publication No. WO 2009/026177. Briefly, LNCaP, KB, and A549 cells are maintained in RPMI 1640 (Gibco RPMI medium 1640, catalog #22400) with glutamine (2 mM), 10% FBS (Fetal Bovine Serum), 1% sodium pyruvate (100 mM) and 1% PS (penicillin streptomycin) in a 5%-CO2 atmosphere at 37° C. Four-five weeks old male nude mice (nu/nu) are obtained from the NCI Charles River.

For tumor cell inoculation, $5.0 \times 10^6$ LNCaP cells in 50% high concentrated matrigel, $1.0 \times 10^6$ KB cells in RPMI medium, or $1.0 \times 10^6$ A549 cells in RPMI medium are subcutaneously injected into the right axial (some animals are injected in both) of the nude mice. The volume of each tumor is measured in two perpendicular directions twice a week using a caliper, (and body weight was measured once a week. The volume of the tumors are calculated as 0.5×L× W2, where L=measurement of longest axis in millimeters and W=measurement of axis perpendicular to L in millimeters.

Example

In Vivo Imaging of Tumors in Mouse. This assay is described in PCT International Publication No. WO 2009/026177. Briefly, when tumors reach a volume of between 500-600 mm$^3$, conjugates described herein, such as $^{99}$mTc-labeled compounds, are administered through intravenous injection or intraperitoneal injection (subcutaneously). Four hours later, animals are euthanized and blood is taken by cardio punch and transferred to individual gamma scintigraphy vials per each animal. The imaging experiments are carried out using either a Kodak or gamma scintigraphic camera imager.

Example

In Vivo Imaging of Tumors in Mouse. This assay is described in PCT International Publication No. WO 2009/026177. Briefly, to further establish the specificity of conjugates for prostate cancer cells, test compounds are injected intraperitoneally (i.p.) or intravenously (i.v.) into athymic nude mice bearing LNCaP or 22RV1 tumors on their shoulders. After 4 h to allow for clearance of unbound conjugate, the distribution of the retained conjugate is imaged by gamma scintigraphy. It is appreciated herein that kidney uptake may be peculiar to the mouse, since immunohistochemical and RT-PCR analyses suggest that PSMA expression is high in murine kidneys but minimal in human kidneys. In vivo specificity of the PSMA-targeted imaging agent is further tested by prior administration of excess PMPA to block all PSMA sites before conjugate administration. To further document specificity, imaging compounds are also administered to PSMA negative mouse xenograft models, such as A549 (a human lung cancer cell line) and KB (a human nasopharyngeal cancer cell line) models, and again whole body images are taken.

Example

Biodistribution Studies. This assay is described in PCT International Publication No. WO 2009/026177. Briefly, after imaging, all animals are dissected approximately 6-7 h after administering test compound and organs (blood, tumor, heart, liver, kidney, spleen, skin, muscle, etc) are transferred to individual gamma scintigraphy vials for each animal and radioactivity is counted. Blood samples are collected (using cardio punch) immediately after sacrificing the animal and before imaging the animal. The plot of tumor to tissue cpm/g ratio verses tissue is used to determine bio-distribution of the imaging agent.

Example

Efficacy study compared to control group and competition group. This assay is described in PCT International Publication No. WO 2009/026177. Briefly, animals are treated with (a) the conjugate administered in 5 doses on alternate days (M, W, F, M, W) at e.g. 1 µmol/kg, and compared to (b) vehicle treated animals, and to (c) animals treated with the conjugate and a competing PSMA binding ligand, such as PMPA.

Example

General Method for Metastatic Prostate Cancer Imaging. Male athymic nu/nu mice (4-5 weeks of age) are anesthetized using 2-3% isfluorane in oxygen prior to injection of $1 \times 10^6$ 22 RV1 cells suspended in 100 µL cell culture medium into the left ventricle of the heart. Once the mouse is fully anesthetized, the animal is placed on its back securing both arms down with tape. The chest is then wiped with 70% ethanol, allowing for the external visualization of the external anatomy of the chest. The injection is made at the second intercostal rib space just along side of the sternum using a 25 gauge needle. The needle is inserted slowly into the heart (6 mm) and cell suspension is injected into the left ventricle of the heart slowly over a period of 30 seconds to 1-minute. After the completion of injection, the needle is quickly withdrawn to prevent cells leaking from the heart.

The development of metastasis is imaged and diagnosed from fourth week onward in vivo by tail vein injection of compounds described herein, where the compound includes an imaging or diagnosing agent (e.g. 10 nmoles/mouse) and imaged after 4 h using a Kodak Imaging Station (In-Vivo FX, Eastman Kodak Company) in combination with CCD camera and Kodak molecular imaging software. The mice are euthanized and cut open for whole body imaging by exposing the internal organs, optionally with shielding or removal of kidneys.

Compounds described herein bind with high affinity and specificity to the various metatheses. For example, dye conjugate compounds VC8, VC9, and VC10 detect the metastatic disease that has spread to various organs, including lungs, face, and liver.

What is claimed is:
1. A conjugate, or a pharmaceutically acceptable salt thereof, comprising a ligand of PSMA (B), a linker (L), and a drug (D), wherein the ligand includes one or more of a carbon-sulfur double bond, a phosphorus-sulfur double bond, a phosphorus-sulfur single bond, a thioester, or a combination thereof, and wherein the linker is covalently bound to the drug and the linker is covalently bound to the ligand, and wherein the linker comprises a chain of at least seven atoms, and wherein the linker does not include a releasable linker.

2. A kit comprising a sterile vial, a composition comprising the conjugate of claim 1 as a lyophilized solid, and instructions describing use of the composition for treating a patient with an inflammatory disease, wherein the vial is an amber glass vial with a rubber stopper and an aluminum tear-off seal, and the vial is stored inside a cardboard box.

3. The conjugate of claim 1, or a pharmaceutically acceptable salt thereof, wherein B is a compound having a formula

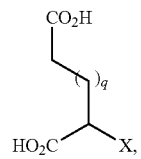

wherein X is RYP(S)(OH)CH$_2$—, RYP(S)(OH)N(R$_1$)—, RP(S)(OH)CH$_2$—, RP(S)(OH)N(R$_1$)—, RP(S)(OH)O—, RYC(S)N(R$_1$)—, RN(OH)C(S)Y, RC(S)NHY, RYP(S)(SH)CH$_2$—, RYP(S)(SH)N(R$_1$)—, RP(S)(SH)CH$_2$—, RP(S)(SH)N(R$_1$)—, RP(S)(SH)S—, RN(SH)C(S)Y—, RC(S)N(OH)Y, RS(O)Y, RSO$_2$Y, RS(O)(NH)Y, or RS-alkyl; wherein Y is independently selected in each instance from —CR$_1$R$_2$—, —NR$_3$—, —S—, and —O—, wherein R is hydrogen, alkyl, aryl, or arylalkyl, each of which may be optionally substituted; and q is 0 to 5; and
wherein R$_1$, R$_2$, and R$_3$ are each independently selected from hydrogen, C$_1$-C$_9$ straight or branched chain alkyl, C$_2$-C$_9$ straight or branched chain alkenyl, C$_3$-C$_8$ cycloalkyl, C$_5$-C$_7$ cycloalkenyl, and aryl.

4. The conjugate of claim 3, or a pharmaceutically acceptable salt thereof, wherein B is a compound of the formula

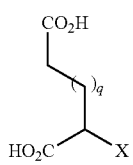

wherein X is RYP(S)(OH)CH$_2$—, RYP(S)(OH)N(R$_1$)—, RP(S)(OH)CH$_2$—, RP(S)(OH)N(R$_1$)—, RYC(S)N(R$_1$)—, RYP(S)(SH)CH$_2$—, RYP(S)(SH)N(R$_1$)—, RP(S)(SH)CH$_2$—, or RP(S)(SH)N(R$_1$)—;

wherein Y is independently selected in each instance from —CR$_1$R$_2$—, —NR$_3$—, —S—, and —O—;

wherein R is hydrogen, alkyl, aryl, or arylalkyl, each of which may be optionally substituted; and q is 0 to 5.

5. The conjugate of claim 3, or a pharmaceutically acceptable salt thereof, wherein q is 1.

6. The conjugate of claim 3, or a pharmaceutically acceptable salt thereof, wherein Y is independently selected in each instance from —CR$_1$R$_2$—, and —NR$_3$—.

7. The conjugate of claim 1, or a pharmaceutically acceptable salt thereof, wherein the linker comprises a chain of at least 14 atoms.

8. The conjugate of claim 1, or a pharmaceutically acceptable salt thereof, wherein the linker comprises a peptide.

9. The conjugate of claim 1, or a pharmaceutically acceptable salt thereof, wherein the linker comprises one or more phenylalanine residues, each of which is independently optionally substituted.

10. The conjugate of claim 1, or a pharmaceutically acceptable salt thereof, wherein the linker comprises phenylalanyl-phenylalanyl, each of which is independently optionally substituted.

11. The conjugate of claim 1, or a pharmaceutically acceptable salt thereof, wherein the ligand is a compound selected from the group consisting of

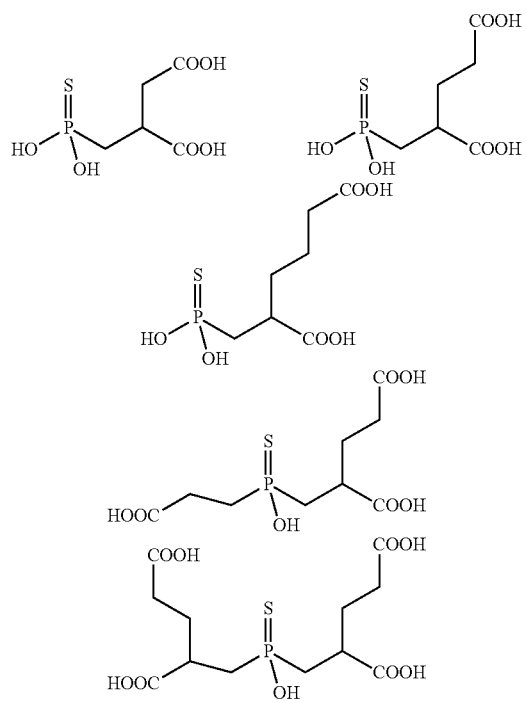

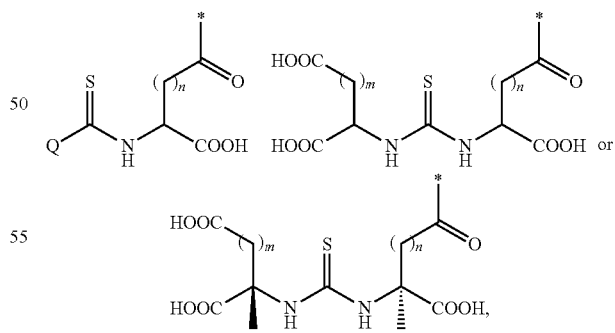

12. The conjugate of claim 1, or a pharmaceutically acceptable salt thereof, wherein the ligand is a fragment having a formula

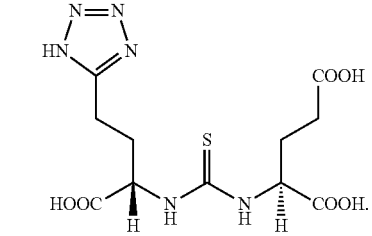

wherein Q is a an amino dicarboxylic acid selected from the group consisting of aspartic acid, glutamic acid, and an analog thereof, n and m are each selected from an integer between 1 and 6, and (*) represents a point of attachment for the linker L.

13. The conjugate of claim 1, or a pharmaceutically acceptable salt thereof, wherein the drug is selected from the group consisting of vinca alkaloids, taxanes, tubulysins, mitomycins, and camptothecins.

14. The conjugate of claim 1, or a pharmaceutically acceptable salt thereof, wherein the drug is an imaging agent selected from the group consisting of Oregon Greens, AlexaFluors, fluoresceins, BODIPY fluorescent agents, rhodamines, and DyLight fluorescent agents.

15. The conjugate of claim 1, or a pharmaceutically acceptable salt thereof, wherein the drug is a compound having a formula

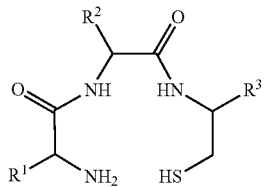

wherein each of $R^1$, $R^2$, and $R^3$ is independently hydrogen or selected from the group consisting of optionally substituted alkyl, heteroalkyl, cycloalkyl, heterocyclyl, alkenyl, alkynyl, aryl, heteroaryl, arylalkyl, and heteroarylalkyl, and wherein one of $R^1$, $R^2$, and $R^3$ comprises a heteroatom selected from the group consisting of nitrogen, oxygen, and sulfur, and is the point of attachment for the linker L.

16. The conjugate of claim 1, or a pharmaceutically acceptable salt thereof, wherein the drug is a PET imaging agent.

17. A pharmaceutical composition comprising a therapeutically effective amount of the conjugate or the pharmaceutically acceptable salt thereof of claim 1, and a component selected from the group consisting of carriers, diluents, and excipients, and combinations thereof.

18. A method for treating a disease involving a pathogenic cell population expressing PSMA, the method comprising administering to a patient in need of relief from the disease a therapeutically effective amount of the conjugate or the pharmaceutically acceptable salt thereof of claim 1, optionally with a component selected from the group consisting of carriers, diluents, and excipients, and combinations thereof.

19. The conjugate of claim 3, or a pharmaceutically acceptable salt thereof, wherein q is 1 and Y is independently selected in each instance from —$CR_1R_2$—, and —$NR_3$—.

20. The conjugate of claim 1, or a pharmaceutically acceptable salt thereof, wherein the linker comprises an amino acid selected from the group consisting of Glu, Asp, Phe, Cys, beta-amino Ala, Gly, amino valeric acid, and amino caproic acid.

21. The conjugate of claim 1, or a pharmaceutically acceptable salt thereof, wherein the linker comprises at least one spacer linker.

22. The conjugate of claim 1, or a pharmaceutically acceptable salt thereof, wherein the linker comprises at least one spacer linker that is an amino acid.

23. The conjugate of claim 1, or a pharmaceutically acceptable salt thereof, wherein the linker does not include a bond that can be broken under physiological conditions.

24. The conjugate of claim 1, or a pharmaceutically acceptable salt thereof, wherein the linker does not include a pH-labile bond.

25. The conjugate of claim 1, or a pharmaceutically acceptable salt thereof, wherein the linker does not include an acid-labile bond.

26. The conjugate of claim 1, or a pharmaceutically acceptable salt thereof, wherein the linker does not include an oxidatively-labile bond.

* * * * *